(12) United States Patent (10) Patent No.: US 11,884,633 B2
Hamamoto et al. (45) Date of Patent: Jan. 30, 2024

(54) ARYLAZOLE COMPOUND AND PEST CONTROL AGENT

(71) Applicant: Nippon Soda Co., Ltd., Tokyo (JP)

(72) Inventors: Isami Hamamoto, Odawara (JP); Hikaru Aoyama, Odawara (JP); Keita Sakanishi, Odawara (JP); Takao Iwasa, Odawara (JP); Tomomi Kobayashi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 17/488,083

(22) Filed: Sep. 28, 2021

(65) Prior Publication Data

US 2022/0017472 A1 Jan. 20, 2022

Related U.S. Application Data

(62) Division of application No. 16/061,783, filed as application No. PCT/JP2016/087358 on Dec. 15, 2016, now Pat. No. 11,180,456.

(30) Foreign Application Priority Data

Dec. 16, 2015 (JP) .................................. 2015-245712
Mar. 24, 2016 (JP) .................................. 2016-060605
Oct. 7, 2016 (JP) .................................. 2016-198677

(51) Int. Cl.
*C07D 231/12* (2006.01)
*C07D 403/12* (2006.01)
(Continued)

(52) U.S. Cl.
CPC ........... *C07D 231/12* (2013.01); *A01N 43/50* (2013.01); *A01N 43/56* (2013.01); *A01N 43/647* (2013.01); *A01N 43/653* (2013.01); *A01N 55/00* (2013.01); *A61K 31/415* (2013.01); *A61K 31/4164* (2013.01); *A61K 31/4178* (2013.01); *A61K 31/4192* (2013.01); *A61K 31/4196* (2013.01); *A61K 31/4439* (2013.01); *A61K 31/695* (2013.01); *C07D 231/14* (2013.01); *C07D 231/16* (2013.01); *C07D 231/18* (2013.01); *C07D 231/38* (2013.01); *C07D 233/64* (2013.01); *C07D 233/68* (2013.01); *C07D 233/84* (2013.01); *C07D 233/88* (2013.01);
(Continued)

(58) Field of Classification Search
None
See application file for complete search history.

(56) References Cited

U.S. PATENT DOCUMENTS 5,556,873 A 9/1996 Huang et al.
2004/0248853 A1 12/2004 Dyckman et al.
(Continued)

FOREIGN PATENT DOCUMENTS

EP 0 396 427 A1 11/1990
EP 0 400 835 A1 12/1990
(Continued)

OTHER PUBLICATIONS

European Search Report dated May 17, 2022 in EP 22158655.5.
(Continued)

*Primary Examiner* — Erin E Hirt
(74) *Attorney, Agent, or Firm* — Foley & Lardner LLP

(57) ABSTRACT

A compound represented by Formula (I), or a salt or N-oxide compound thereof is provided.

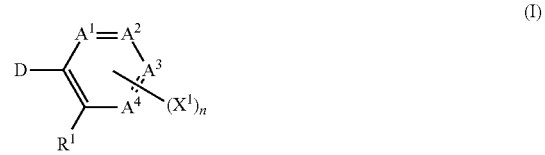

In Formula (I), $A^1$ to $A^4$ each independently represents a carbon atom or nitrogen atom, $X^1$ represents a C1-6 alkyl group or the like, n represents the number of $X^1$ groups, $R^1$ represents a C1-6 alkylthio group or the like, and D is a group represented by Formula (D-1) or (D-2), and

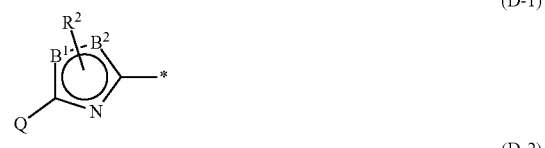

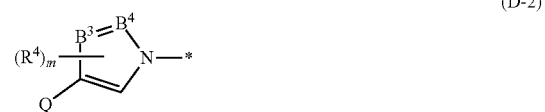

in Formula (D-1) and (D-2), * represents a binding position, Q represents a C1-6 alkyl group or the like, $B^1$ and $B^2$ each independently represents a nitrogen atom or the like, $R^2$ represents a C1-6 alkyl group or the like that is bound to one of the nitrogen atoms in Formula (D-1), $B^3$ and $B^4$ each independently represents a nitrogen atom or carbon atom, $R^4$ represents a C1-6 alkyl group or the like, and m represents the number of $R^4$ groups.

7 Claims, No Drawings

(51) Int. Cl.
A01N 43/50 (2006.01)
A01N 43/56 (2006.01)
A01N 43/653 (2006.01)
C07D 231/38 (2006.01)
C07D 233/64 (2006.01)
C07D 233/68 (2006.01)
C07D 233/84 (2006.01)
C07D 233/88 (2006.01)
C07D 233/90 (2006.01)
C07D 401/04 (2006.01)
C07D 401/12 (2006.01)
C07D 403/06 (2006.01)
C07D 403/10 (2006.01)
C07D 405/06 (2006.01)
C07D 405/04 (2006.01)
C07D 249/06 (2006.01)
C07D 231/14 (2006.01)
A01N 55/00 (2006.01)
A61K 31/695 (2006.01)
A61K 31/4192 (2006.01)
A61K 31/4439 (2006.01)
A61K 31/415 (2006.01)
A61K 31/4178 (2006.01)
A61K 31/4196 (2006.01)
C07F 7/10 (2006.01)
C07D 249/08 (2006.01)
C07D 231/16 (2006.01)
C07D 231/18 (2006.01)
C07D 403/04 (2006.01)
A61K 31/4164 (2006.01)
A01N 43/647 (2006.01)

(52) U.S. Cl.
CPC ......... C07D 233/90 (2013.01); C07D 249/06 (2013.01); C07D 249/08 (2013.01); C07D 401/04 (2013.01); C07D 401/12 (2013.01); C07D 403/04 (2013.01); C07D 403/06 (2013.01); C07D 403/10 (2013.01); C07D 403/12 (2013.01); C07D 405/04 (2013.01); C07D 405/06 (2013.01); C07F 7/10 (2013.01)

(56) References Cited

U.S. PATENT DOCUMENTS

| 2010/0093757 | A1* | 4/2010 | Bennett | A61P 3/10 |
| | | | | 560/186 |
| 2011/0190365 | A1 | 8/2011 | Werner et al. | |
| 2012/0190687 | A1 | 7/2012 | Schwarz et al. | |
| 2017/0223958 | A1 | 8/2017 | Aoyama et al. | |

FOREIGN PATENT DOCUMENTS

| EP | 0 846 686 A1 | 6/1998 |
| EP | 1 022 270 A1 | 7/2000 |
| EP | 3 312 162 A1 | 4/2018 |
| JP | 03-027361 A | 2/1991 |
| JP | 03-027362 A | 2/1991 |
| JP | 2002-504546 A | 2/2002 |
| JP | 2005-512969 A | 5/2005 |
| JP | 2005-522458 A | 7/2005 |
| JP | 2007-529439 A | 10/2007 |
| JP | 2007-284356 A | 11/2007 |
| JP | 2007-308485 A | 11/2007 |
| JP | 2008-543971 A | 12/2008 |
| JP | 2009-536218 A | 10/2009 |
| JP | 2009-538335 A | 11/2009 |
| JP | 2011-529955 A | 12/2011 |
| JP | 2018-502917 A | 2/2018 |
| JP | 6569184 B2 | 8/2019 |
| KR | 10-2006-0022649 A | 3/2006 |
| WO | WO-95/33730 | 12/1995 |
| WO | WO-98/27108 A2 | 6/1998 |
| WO | WO-98/32739 A1 | 7/1998 |
| WO | WO-99/02518 A1 | 1/1999 |
| WO | WO-99/43663 A1 | 9/1999 |
| WO | WO-02/15662 A2 | 2/2002 |
| WO | WO-03/029222 A1 | 4/2003 |
| WO | WO-03037330 A1 * | 5/2003 ........... C07D 401/04 |
| WO | WO-03/072557 A1 | 9/2003 |
| WO | WO-2004/098518 A2 | 11/2004 |
| WO | WO-2005/090314 A1 | 9/2005 |
| WO | WO-2007/002563 A1 | 1/2007 |
| WO | WO-2007/131179 A1 | 11/2007 |
| WO | WO-2007/140183 A1 | 12/2007 |
| WO | WO-2010/015849 A2 | 2/2010 |
| WO | WO-2010/017902 A1 | 2/2010 |
| WO | WO-2010/136145 A1 | 12/2010 |
| WO | WO-2012/073995 A1 | 6/2012 |
| WO | WO-2014/144895 | 10/2015 |
| WO | WO-2015/144826 A1 | 10/2015 |
| WO | WO-2015/144895 A1 | 10/2015 |
| WO | WO-2015/185485 A1 | 12/2015 |
| WO | WO-2016/024587 A1 | 2/2016 |
| WO | WO-2016/113155 A1 | 7/2016 |
| WO | WO-2016/204270 A1 | 12/2016 |

OTHER PUBLICATIONS

Diaz (293 Introduction to ectoparasitic diseases in Mandell, Douglas, and Bennet's Principles and Practice of Infectious Diseases (8th Edition, 2015, vol. 2, p. 3423-3245.E1, first page only). (Year: 2015).

Final Office Action dated Nov. 25, 2019 in U.S. Appl. No. 16/061,783.

Final Office Action dated Dec. 7, 2020 in U.S. Appl. No. 16/061,783.

International Search Report dated Mar. 7, 2017, in PCT/JP2016/087358.

Kuriyama et al., "Ether-Imidazolium Carbenes for Suzuki-Miyaura Cross-Coupling of Heteroaryl Chlorides with Aryl/Heteroarylboron Reagents," Organic Letters, 2013, 15(11):2716-2719.

Mao et al., "Synthesis, Crystal Structure, Insecticidal and Acaricidal Activities of Novel N-Bridged Derivatives of 2-(p-chlorophenyl)pyrrole," Chinese Journal of Organic Chemistry, Dec. 31, 2009, 29(6):929-935.

Non-Final Office Action dated May 29, 2021 in U.S. Appl. No. 16/061,783.

Non-Final Office Action dated Jun. 26, 2019 in U.S. Appl. No. 16/061,783.

Notice of Allowance dated Jul. 1, 2021 in U.S. Appl. No. 16/061,783.

Office Action and Search Report dated Dec. 28, 2020 in CN 201680072673.5, with partial English translation of search report.

Office Action dated Apr. 28, 2020 in JP 2017-556438, with English translation.

Office Action dated Mar. 12, 2021 in TW 109120641, with English translation.

Restriction Requirement dated Mar. 21, 2019 in U.S. Appl. No. 16/061,783.

Schweinfurth et al., "Heterobimetallic Cu-dppf (dppf=1,1'-Bis(diphenylphosphino)ferrocene) Complexes with "Click" Derived Ligands: A Combined Structural, Electrochemical, Spectroelectrochemical, and Theoretical Study," Organometallics, 2013, 32(20):5834-5842.

STN International, 1H-1,2,3-Triazole, 4-(2-bromoethyl)-1-(2-(methylthio)phenyl)-, File Registry [online], Entered STN: Oct. 31, 2010, retrieval date: Feb. 14, 2017, CAS Registry No. 1249171-19-4.

STN International, 1H-1,2,3-Triazole, 4-(2-chloroethyl)-1-(2-(methylthio)phenyl)-, File Registry [online], Entered STN: Oct. 28, 2010, retrieval date: Feb. 14, 2017, CAS Registry No. 1248083-42-2.

STN International, 1H-Imidazole-4,5-dicarbonitrile, 1-(3-(methylsulfonyl)-2-pyridinyl)-, File Registry [online], ED Entered STN: Jun. 4, 2015, retrieval date: Feb. 14, 2017, CAS Registry No. 1772746-44-7.

(56) References Cited

OTHER PUBLICATIONS

STN International, 1H-Pyrazole-4-carboxylic acid, 1-(2-methylsulfunyl)phenyl)-2-penten-1-yl ester, File Registry [online], ED Entered STN: Jul. 19, 2013, retrieval date: Feb. 14, 2017, CAS Registry No. 1445756-97-7.
Texas A&M (https://livestockvetento.tamu.edu/insectspests/botflies/). Cached wayback machine, Jun. 6, 2011.
Notice of Allowance dated Dec. 15, 2021 in KR 10-2021-7023229, with English translation.
Non-Final Office Action dated May 29, 2020 in U.S. Appl. No. 16/061,783.
Office Action dated Dec. 6, 2022 in JP 2022-006700, with English translation.

* cited by examiner

ARYLAZOLE COMPOUND AND PEST CONTROL AGENT

CROSS-REFERENCE TO RELATED APPLICATIONS

This application is a Divisional of U.S. application Ser. No. 16/061,783, which is the U.S. National Stage application of PCT/JP2016/087358, filed Dec. 15, 2016, which claims priority from Japanese Patent Application No. 2015-245712, filed on Dec. 16, 2015, Japanese Patent Application No. 2016-060605, filed on Mar. 24, 2016, and Japanese Patent Application No. 2016-198677, filed on Oct. 7, 2016, the contents of which are incorporated herein by reference.

TECHNICAL FIELD

The present invention relates to an arylazole compound and a pest control agent. More particularly, the present invention relates to an arylazole compound which exhibits excellent insecticidal activity and/or acaricidal activity, is highly safe, and can be industrially favorably synthesized, and a pest control agent containing the same as an active ingredient thereof.

BACKGROUND ART

Various compounds exhibiting insecticidal and acaricidal activity have been suggested. In order to practically use such a compound as an agricultural chemical, the compound is required not only to have sufficiently high efficacy but also to be unlikely to cause drug resistance, to be unlikely to cause phytotoxicity to plants and soil contamination, and to exhibit low toxicity to livestock and fish.

PTL 1 discloses a compound represented by Formula (A). According to PTL 1, the compound has a potent inhibitory activity against the production of nitric oxide and is effective for the prevention and/or treatment of nitric oxide-mediated diseases.

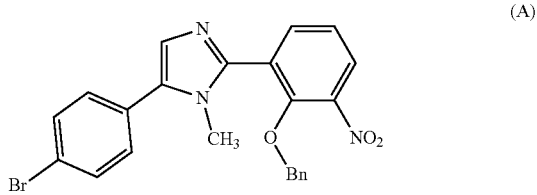 [SMILES: Cn1c(-c2ccc(Br)cc2)cnc1-c1cccc([N+](=O)[O-])c1OCc1ccccc1]

(A)

In addition, PTL 2 discloses a compound represented by Formula (B).

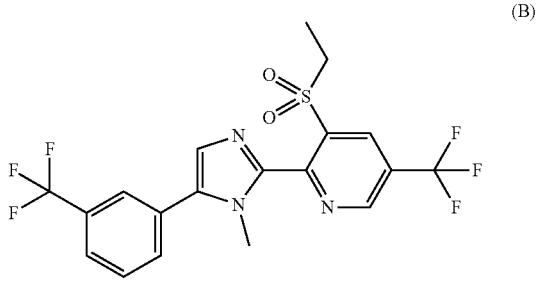 [SMILES: CCS(=O)(=O)c1cc(C(F)(F)F)cnc1-c1ncc(-c2cccc(C(F)(F)F)c2)n1C]

(B)

CITATION LIST

Patent Literature

[PTL 1] WO 98/27108 A2
[PTL 2] WO2015/144895 A1

SUMMARY OF INVENTION

Technical Problem

An object of the present invention is to provide an arylazole compound which has excellent pesticidal activity, in particular, insecticidal activity and/or acaricidal activity, is highly safe and can be industrially favorably synthesized, and to provide a pest control agent containing the arylazole compound as an active ingredient. Another object of the present invention is to provide an ectoparasite control agent containing the arylazole compound as an active ingredient.

Solution to Problem

As a result of intensive studies to achieve the above-mentioned objects, the present invention including the following aspects has been completed.

That is, the present invention includes the following aspects.

[1] A compound represented by Formula (I), or a salt or N-oxide compound thereof.

(I)

In Formula (I),
$A^1$ to $A^4$ each independently represents a carbon atom or a nitrogen atom, provided that two or more of $A^1$ to $A^4$ are not nitrogen atoms at the same time.

$X^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, an unsubstituted or substituted C1-6 alkylaminocarbonyl group, a mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C3-8 cycloalkyl group, an unsubstituted or substituted C6-10 aryl group, an unsubstituted or substituted 3- to 6-membered heterocyclyl group, an unsubstituted or substituted amino group, a halogeno group, a cyano group, or a nitro group.

n represents the number of chemically acceptable $X^1$ and is any integer of 0 to 4. When n is 2 or more, $X^1$ may be the same as or different from each other, and also two $X^1$ may be bound together to form a ring.

$R^1$ represents an unsubstituted or substituted C1-6 alkylthio group, an unsubstituted or substituted C1-6 alkylsulfinyl group, an unsubstituted or substituted C1-6 alkylsulfonyl group, or a C1-6 alkylsulfoxyimino group, or a group represented by —S(=O) (=N—R$^a$)—R$^b$, wherein, R$^a$ represents a hydrogen atom, a cyano group, a C1-6 alkyl group, or an unsubstituted or substituted C1-6 alkylcarbonyl group, and R$^b$ represents a C1-6 alkyl group.

D is a group represented by Formula (D-1) or Formula (D-2).

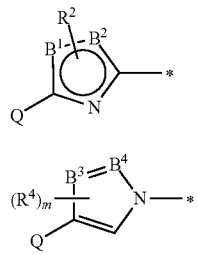

In Formulas (D-1) and (D-2), * represents a binding position.

Q represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C1-6 alkoxycarbonyl group, an unsubstituted or substituted aminocarbonyl group, an unsubstituted or substituted 3- to 6-membered heterocyclyloxycarbonyl group, an unsubstituted or substituted 3- to 6-membered heterocyclyl group, an unsubstituted or substituted allene group, a cyano group, a group represented by —CR$^c$=NO—R$^d$, or a group represented by —N=CR$^e$R$^f$, wherein, R$^c$ represents a hydrogen atom, or an unsubstituted or substituted C1-6 alkyl group, R$^d$ represents an unsubstituted or substituted C1-6 alkyl group, or an unsubstituted or substituted phenyl group, and R$^e$ and R$^f$ represent a hydrogen atom, an unsubstituted or substituted C1-6 alkyl group, a substituted amino group, or a halogeno group.

In Formula (D-1),

B$^1$ and B$^2$ each independently represents a nitrogen atom or CR$^3$. When B$^1$ and B$^2$ are both CR$^3$, the two R$^3$'s may be the same or different.

R$^2$ is a substituent bound to one of the nitrogen atoms of Formula (D-1). R$^2$ represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, or an unsubstituted or substituted C1-6 alkylsulfonyl group.

R$^3$ represents a hydrogen atom, an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, a halogeno group, a cyano group, or a nitro group.

In Formula (D-2),

B$^3$ and B$^4$ each independently represents a nitrogen atom or carbon atom, provided that B$^3$ and B$^4$ are not carbon atoms at the same time.

R$^4$ represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted amino group, a halogeno group, a cyano group, or a nitro group.

m represents the number of chemically acceptable R$^4$ and is any integer of 0 to 2. When m is 2 or more, R$^4$ may be the same as or different from each other.

[2] The compound according to [1], which is represented by Formula (II), or a salt or N-oxide compound thereof.

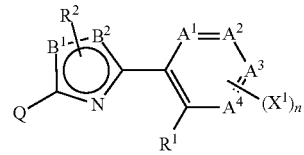

In Formula (II), A$^1$ to A$^4$, X$^1$, n, and R$^1$ have the same meanings as those in Formula (I). In Formula (II), B$^1$, B$^2$, R$^2$, and Q have the same meanings as those in Formula (D-1).

[3] The compound according to [1], which is represented by Formula (III), or a salt or N-oxide compound thereof.

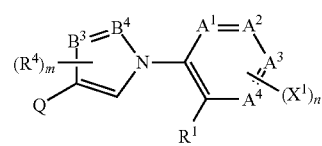

In Formula (III), A$^1$ to A$^4$, X$^1$, n, and R$^1$ have the same meanings as those in Formula (I). In Formula (III), B$^3$, B$^4$, R$^4$, m, and Q have the same meanings as those in Formula (D-2).

[4] A pest control agent including at least one selected from the group consisting of the compound according to any one of [1] to [3], and a salt or N-oxide compound thereof, as an active ingredient.

[5] An insecticide or acaricide including at least one selected from the group consisting of the compound according to any one of [1] to [3], and a salt or N-oxide compound thereof, as an active ingredient.

[6] An ectoparasite control agent including at least one selected from the group consisting of the compound according to any one of [1] to [3], and a salt or N-oxide compound thereof, as an active ingredient.

[7] An endoparasite control agent or an endoparasite-expelling agent including at least one selected from the group consisting of the compound according to any one of [1] to [3], and a salt or N-oxide compound thereof, as an active ingredient.

Advantageous Effects of Invention

With, the arylazole compound of the present invention, pests which are problematic in terms of protecting agricultural crop hygiene can be controlled. Especially, agricultural pests and mites can be particularly effectively controlled. Additionally, using the arylazole compounds, ectoparasites and endoparasites which harm humans and livestock can also be effectively controlled as well.

DESCRIPTION OF EMBODIMENTS

[Arylazole Compound]

The arylazole compound according to the present invention is a compound represented by Formula (I) (hereinafter, also referred as Compound (I)), or a salt or N-oxide compound of Compound (I).

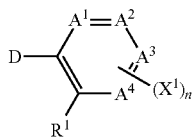
(I)

In the present invention, the term "unsubstituted" refers to a group consisting of only a mother nucleus. A name-only group which serves as a mother nucleus without the term "substituted" means an "unsubstituted" group unless specifically indicated otherwise.

The term "substituted" means that a hydrogen atom of a group which serves as a mother nucleus is being substituted with a group having a structure that is the same as or different from the mother nucleus. Thus, the "substituent" means another group bound to the group serving as a mother nucleus. There may be one substituent, or there may be two or more substituents. Two or more substituents may be the same or different.

The term "C1 to 6" or the like means that the number of carbon atoms in the group serving as a mother nucleus is 1 to 6, or the like. The number of carbon atoms does not include the number of carbon atoms present in the substituent. For example, a butyl group having an ethoxy group as a substituent is classified as a C2 alkoxy C4 alkyl group.

There are no particular limitations on the "substituent" provided that they are chemically acceptable and with which the effects of the present invention can be achieved. Examples of groups that can be a "substituent" include the following groups.

C1-6 alkyl groups such as a methyl group, an ethyl group, an n-propyl group, an i-propyl group, an n-butyl group, an s-butyl group, an i-butyl group, a t-butyl group, an n-pentyl group, and an n-hexyl group;

C2-6 alkenyl groups such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-8 cycloalkyl groups such as a cyclopropyl group, a cyclobutyl group, a cyclopentyl group, a cyclohexyl group, and a cubanyl group;

C6-10 aryl groups such as a phenyl group and a naphthyl group;

C6-10 aryl C1-6 alkyl groups such as a benzyl group and a phenethyl group;

3- to 6-membered heterocyclyl groups;

3- to 6-membered heterocyclyl C1-6 alkyl groups;

a hydroxyl group;

C1-6 alkoxy groups such as a methoxy group, an ethoxy group, an n-propoxy group, an i-propoxy group, an n-butoxy group, an s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group and a propargyloxy group;

C6-10 aryloxy groups such as a phenoxy group and a naphthoxy group;

C6-10 aryl C1-6 alkoxy groups such as a benzyloxy group and a phenethyloxy group;

5- to 6-membered heteroaryloxy groups such as a thiazolyloxy group and a pyridyloxy group;

5- to 6-membered heteroaryl C1-6 alkyloxy groups such as a thiazolylmethyloxy group and a pyridylmethyloxy group;

a formyl group;

C1-6 alkylcarbonyl groups such as an acetyl group and a propionyl group;

a formyloxy group;

C1-6 alkylcarbonyloxy groups such as an acetyloxy group and a propionyloxy group;

C6-10 arylcarbonyl groups such as a benzoyl group;

C1-6 alkoxycarbonyl groups such as a methoxycarbonyl group, an ethoxycarbonyl group, an n-propoxycarbonyl group, an i-propoxycarbonyl group, an n-butoxycarbonyl group, and a t-butoxycarbonyl group;

C1-6 alkoxycarbonyloxy group such as a methoxycarbonyloxy group, an ethoxycarbonyloxy group, an n-propoxycarbonyloxy group, an i-propoxycarbonyloxy group, an n-butoxycarbonyloxy group, and a t-butoxycarbonyloxy group;

a carboxyl group;

a halogeno group such as a fluoro group, a chloro group, a bromo group, and an iodo group;

C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group;

C2 to 6 haloalkenyl groups such as a 2-chloro-1-propenyl group and a 2-fluoro-1-butenyl group;

C2-6 haloalkynyl group such as a 4,4-dichloro-1-butynyl group, a 4-fluoro-1-pentynyl group, a 5-bromo-2-pentynyl group;

C1-6 haloalkoxy groups such as a trifluoromethoxy group, a 2-chloro-n-propoxy group, and a 2,3-dichlorobutoxy group;

C2-6 haloalkenyloxy groups such as a 2-chloropropenyloxy group and a 3-bromobutenyloxy group;

C1-6 haloalkylcarbonyl groups such as a chloroacetyl group, a trifluoroacetyl group, and a trichloroacetyl group;

an amino group;

C1-6 alkyl-substituted amino groups such as a methylamino group, a dimethylamino group, and a diethylamino group;

C6-10 arylamino groups such as an anilino group and a naphthylamino group;

C6-10 aryl C1-6 alkylamino groups such as a benzylamino group, and a phenethylamino group;

a formylamino group;

C1-6 alkylcarbonylamino groups such as an acetylamino group, a propanoylamino group, a butyrylamino group, an i-propylcarbonylamino group or the like;

C1-6 alkoxycarbonylamino groups such as a methoxycarbonylamino group, an ethoxycarbonylamino group, an n-propoxycarbonylamino group, and i-propoxycarbonylamino group; unsubstituted or substituted aminocarbonyl groups such as an aminocarbonyl group, a dimethylaminocarbonyl group, a phenylaminocarbonyl group, an N-phenyl-N-methylaminocarbonyl group, and an N-butyl-N-methylaminocarbonyl group;

imino C1-6 alkyl groups such as an iminomethyl group, (1-imino)ethyl group, and (1-imino)-n-propyl group;

an unsubstituted or substituted N-hydroxyimino C1-6 alkyl group such as an N-hydroxy-iminomethyl group, a (1-(N-hydroxy)-imino) ethyl group, a (1-(N-hydroxy)-imino) propyl group, an N-methoxy-iminomethyl group, and a (1-(N-methoxy)-imino) ethyl group;

an aminocarbonyloxy group;

C1-6 alkyl-substituted aminocarbonyloxy groups such as an ethylaminocarbonyloxy group and a dimethylaminocarbonyloxy group;

a mercapto group;

C1-6 alkylthio groups such as a methylthio group, an ethylthio group, an n-propylthio group, an i-propylthio group, an n-butylthio group, a i-butylthio group, an s-butylthio group, and a t-butylthio group;

C1-6 haloalkylthio groups such as a trifluoromethylthio group and a 2,2,2-trifluoroethylthio group;

C6-10 arylthio groups such as a phenylthio group and a naphthylthio group;

5- to 6-membered heteroarylthio groups such as a thiazolylthio group and a pyridylthio group;

C1-6 alkylsulfinyl groups such as a methylsulfinyl group, an ethylsulfinyl group, and a t-butylsulfinyl group;

C1-6 haloalkylsulfinyl groups such as a trifluoromethylsulfinyl group and a 2,2,2-trifluoroethylsulfinyl group;

C6-10 arylsulfinyl groups such as a phenylsulfinyl group;

5- to 6-membered heteroarylsulfinyl groups such as a thiazolylsulfinyl group and a pyridylsulfinyl group;

C1-6 alkylsulfonyl groups such as a methylsulfonyl group, an ethylsulfonyl group, a t-butylsulfonyl group or the like;

C1-6 haloalkylsulfonyl groups such as a trifluoromethylsulfonyl group and a 2,2,2-trifluoroethylsulfonyl group;

C6-10 arylsulfonyl group such as a phenylsulfonyl group;

5- to 6-membered heteroarylsulfonyl groups such as a thiazolylsulfonyl group and a pyridylsulfonyl group;

C1-6 alkylsulfonyloxy groups such as a methylsulfonyloxy group, an ethylsulfonyloxy group, and a t-butylsulfonyloxy group;

C1-6 haloalkylsulfonyloxy groups such as a trifluoromethylsulfonyloxy group and a 2,2,2-trifluoroethylsulfonyloxy group;

tri-C1-6 alkyl-substituted silyl groups such as a trimethylsilyl group, a triethylsilyl group, and a t-butyldimethylsilyl group;

tri-C6-10 aryl-substituted silyl groups such as triphenylsilyl group; and a cyano group; a nitro group;

further, these "substituents" may have a group having a different structure which has replaced a hydrogen atom of the substituent. Examples of the "substituent" in such a case include C1-6 alkyl groups, C1-6 haloalkyl groups, C1-6 alkoxy groups, C1-6 haloalkoxy groups, a halogeno group, a cyano group, and a nitro group.

The above "3- to 6-membered heterocyclyl groups" include 1 to 4 hetero atoms selected from the group consisting of a nitrogen atom, an oxygen atom and a sulfur atom as the constituent atoms of the ring. The heterocyclyl group may be either monocyclic or polycyclic. Insofar as at least one ring is a hetero ring in the polycyclic heterocyclyl group, the remaining ring(s) may be any of a saturated alicyclic ring, an unsaturated alicyclic ring or an aromatic ring. The "3- to 6-membered heterocyclyl groups" include a 3- to 6-membered saturated heterocyclyl groups, a 5- to 6-membered heteroaryl groups, and a 5- to 6-membered partially unsaturated heterocyclyl groups.

Examples of the 3- to 6-membered saturated heterocyclyl groups include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl groups include a pyridyl group, a pyrazinyl group, a pyrimidinyl group, a pyridazinyl group, and a triazinyl group.

In Formula (I), $A^1$ to $A^4$ each independently represents a carbon atom or a nitrogen atom. There cannot be two or more nitrogen atoms in $A^1$ to $A^4$.

That is, the compound represented by Formula (I) is a compound represented by Formula (a) to Formula (e).

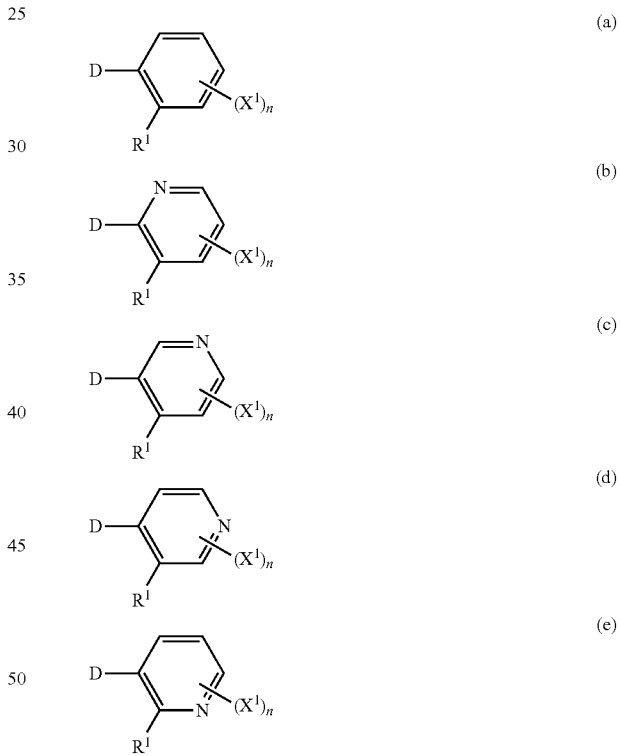

In Formulas (a) to (e), $X^1$, $R^1$, n and D have the same meanings as those in Formula (I).

In Formula (I), $X^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, an unsubstituted or substituted C1-6 alkylaminocarbonyl group, a mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C3-8 cycloalkyl group, an unsubstituted or substituted C6-10 aryl group, an unsubstituted or substituted 3- to 6-membered heterocyclyl group, an unsubstituted or substituted amino group, a halogeno group, a cyano group, or a nitro group.

The "C1-6 alkyl group" as $X^1$ may be linear and may be branched provided that the group has 3 or more carbon atoms. Examples of an alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, and an i-hexyl group.

Specific examples of the "C1-6 alkyl group having a substituent" include C1-6 haloalkyl groups such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 1-chloroethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, 2,2,2-trifluoro-1-trifluoromethylethyl group, a 1,1,1,3,3,3-hexafluoropropan-2-yl group, a perfluoropropan-2-yl group, a perfluorohexyl group, a perchlorohexyl group, and a 2,4,6-trichlorohexyl group;

hydroxy C1-6 alkyl groups such as a hydroxymethyl group and a hydroxyethyl group;

C1-6 alkoxy C1-6 alkyl groups such as a methoxymethyl group, an ethoxymethyl group, a methoxyethyl group, an ethoxyethyl group, a methoxy-n-propyl group, an n-propoxymethyl group, an i-propoxyethyl group, an s-butoxymethyl group, and a t-butoxyethyl group;

C6-10 aryl C1-6 alkyl groups such as a benzyl group and a phenethyl group;

C3-8 cycloalkyl C1-6 alkyl groups such as a cyclopropylmethyl group, a 2-cyclopropylethyl group, a cyclopentylmethyl group, a 2-cyclohexylethyl group, and a 2-cyclooctylethyl group, and the like.

Examples of the "C2-6 alkenyl group" as $X^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Specific examples of the "C2-6 alkenyl group having a substituent" include C2-6 haloalkenyl groups such as a 2-chloro-1-propenyl group and a 2-fluoro-1-butenyl group; C1-6 alkoxy C2-6 alkenyl groups such as 2-n-butoxy-vinyl group and 1-ethoxy-vinyl group;

Examples of the "C2-6 alkynyl group" as $X^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Specific examples of the "C2-6 alkynyl group having a substituent" include C2-6 haloalkynyl groups such as a 4,4-dichloro-1-butynyl group, a 4-fluoro-1-pentynyl group, a 5-bromo-2-pentynyl group.

Examples of the "C1-6 alkoxy group" as $X^1$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group, and an i-hexyloxy group.

Specific examples of the "C1-6 alkoxy group having a substituent" include C1-6 haloalkoxy groups such as a trifluoromethoxy group, a difluoromethoxy group, a 1-fluoroethoxy group, a 1,1-difluoroethoxy group, a 2,2,2-trifluoroethoxy group, a pentafluoroethoxy group, a 2,2,3,4,4,4-hexafluoro-butoxy group, a chloromethoxy group, a dichloromethoxy group, and a trichloromethoxy group;

C1-6 alkoxy C1-6 alkoxy groups such as a methoxymethoxy group and a methoxyethoxy group;

C6-10 aryl C1-6 alkoxy groups such as a benzyloxy group and a phenethyloxy group; and C3-8 cycloalkyl C1-6 alkoxy group such as a cyclopropylmethyloxy group.

Examples of the "C1-6 alkylcarbonyl group" as $X^1$ include an acetyl group, and a propionyl group.

Specific examples of the "C1-6 alkylcarbonyl group having a substituent" include C1-6 haloalkylcarbonyl groups such as a chloroacetyl group, a trifluoroacetyl group and a trichloroacetyl group.

Examples of the "C1-6 alkoxycarbonyl group" as $X^1$ include a methoxycarbonyl group, an ethoxycarbonyl group, an n-propoxycarbonyl group, an i-propoxycarbonyl group, and a t-butoxycarbonyl group.

Specific examples of the "C1-6 alkoxycarbonyl group having a substituent" include C1-6 haloalkoxycarbonyl groups such as a fluoromethoxycarbonyl group, a chloromethoxycarbonyl group, a bromomethoxycarbonyl group, a difluoromethoxycarbonyl group, a dichloromethoxycarbonyl group, a dibromomethoxycarbonyl group, a trifluoromethoxycarbonyl group, a trichloromethoxycarbonyl group, a tribromomethoxycarbonyl group, and a 2,2,2-trifluoroethoxycarbonyl group; C3-8 cycloalkyl C1-6 alkoxycarbonyl groups such as a cyclopropylmethoxycarbonyl group, a cyclobutylmethoxycarbonyl group, a cyclopentylmethoxycarbonyl group, a cyclohexylmethoxycarbonyl group, and a 2-cyclopropylethoxycarbonyl group.

Examples of the "C1-6 alkylaminocarbonyl group" as $X^1$ include a methylaminocarbonyl group, an ethylaminocarbonyl group, a butylaminocarbonyl group, a dimethylaminocarbonyl group, a diethylaminocarbonyl group, and an N-butyl-N-methylaminocarbonyl group.

Examples of the "C1-6 alkylthio group" as $X^1$ include a methylthio group, an ethylthio group, an n-propylthio group, an n-butylthio group, an n-pentylthio group, an n-hexylthio group, an i-propylthio group, and an i-butylthio group.

Specific examples of the "C1-6 alkylthio group having a substituent" include a C1-6 haloalkylthio groups such as a trifluoromethylthio group and a 2,2,2-trifluoroethylthio group.

Examples of the "C1-6 alkylsulfinyl group" as $X^1$ include a methylsulfinyl group, an ethylsulfinyl group, and a t-butylsulfinyl group.

Specific examples of the "C1-6 alkylsulfinyl group having a substituent" include a C1-6 haloalkylsulfinyl group such as a trifluoromethylsulfinyl group and a 2,2,2-trifluoroethylsulfinyl group.

Examples of the "C1-6 alkylsulfonyl group" as $X^1$ include a methylsulfonyl group, an ethylsulfonyl group, and a t-butylsulfonyl group.

Specific examples of the "C1-6 alkylsulfonyl group having a substituent" include C1-6 haloalkylsulfonyl groups such as a trifluoromethylsulfonyl group and a 2,2,2-trifluoroethylsulfonyl group.

Examples of the preferable substituent in the "C1-6 alkyl group", the "C2-6 alkenyl group", the "C2-6 alkynyl group", the "C1-6 alkoxy group", the "C1-6 alkylcarbonyl group", the "C1-6 alkoxycarbonyl group", the "C1-6 alkylaminocarbonyl group", the "C1-6 alkylthio group", the "C1-6 alkylsulfinyl group", and the "C1-6 alkylsulfonyl group" as $X^1$ include a C1-6 alkoxy group, a halogeno group, a cyano group, a hydroxyl group, a C3-8 cycloalkyl group, a C6-10 aryl group, and a 3- to 6-membered heterocyclyl group.

Examples of the "C3-8 cycloalkyl group" as $X^1$ include a cyclopropyl group, a cyclobutyl group, a cyclopentyl group, a cyclohexyl group, and a cycloheptyl group.

The "C6-10 aryl group" as $X^1$ may be either a monocyclic ring or a polycyclic ring. Insofar as at least one ring is an aromatic ring in the polycyclic aryl group, the remaining ring(s) may be any of a saturated alicyclic ring, an unsaturated alicyclic ring and an aromatic ring.

Examples of the "C6-10 aryl group" include a phenyl group, a naphthyl group, an azulenyl group, an indenyl group, an indanyl group, and a tetralinyl group.

The "3- to 6-membered heterocyclyl group" as $X^1$ contains 1 to 4 hetero atoms selected from the group consisting of a nitrogen atom, an oxygen atom and a sulfur atom as constituent atoms of the ring. The heterocyclyl group may be either monocyclic or polycyclic. Insofar as at least one ring is a heterocyclic ring in the polycyclic heterocyclyl group, the remaining ring(s) may be any of a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, and a 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group (specifically, a [1,3]dioxolanyl group), and a dioxanyl group (specifically, a [1,3]dioxanyl group or a [1,4]dioxanyl group); preferable example thereof is a 5- to 6-membered saturated heterocyclyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group (specifically, a [1,2,3]triazolyl group or a [1,2,4]triazolyl group), an oxadiazolyl group (specifically, a [1,2,4]oxadiazolyl group, or a [1,3,4] oxadiazolyl group), a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

The partially unsaturated 5-membered heterocyclyl group includes a pyrrolinyl group, an imidazolinyl group (dihydroimidazolyl group), a pyrazolinyl group, an oxazolinyl group, an isoxazolinyl group, and a thiazolinyl group.

Examples of the partially unsaturated 6-membered heterocyclyl group include a thiopyranyl group, 2H-pyridin-1-yl group, and 4H-pyridin-1-yl group.

Examples of the substituent in the "C3-8 cycloalkyl group", "C6-10 aryl group" and "3- to 6-membered heterocyclyl group" as $X^1$ include a C1-6 alkyl group, a C1-6 haloalkyl group, a hydroxyl group, a C1-6 alkoxy group, a halogeno group, a cyano group, a nitro group, and an amino group.

Examples of the "amino group having a substituent" as $X^1$ include C1-6 alkyl-substituted amino groups such as a methylamino group, an ethylamino group, an n-butylamino group, a dimethylamino group, a diethylamino group, and a dibutylamino group.

Examples of the "halogeno group" as $X^1$ include a fluoro group, a chloro group, a bromo group, and an iodo group.

As $X^1$, a C1-6 alkyl group, a C1-6 haloalkyl group, a C1-6 alkoxy group, a C1-6 haloalkoxy group, a C1-6 alkylthio group, a C1-6 alkylsulfonyl group, a halogeno group, a cyano group, or an unsubstituted or substituted 3- to 6-membered heterocyclyl group is preferable, and a C1-6 haloalkyl group or an unsubstituted or substituted 3- to 6-membered heterocyclyl group is more preferable, and a C1-6 haloalkyl group or an unsubstituted or substituted 5- to 6-membered heteroaryl group is even more preferable.

In Formula (I), n represents the number of chemically acceptable $X^1$ and is an integer of 0 to 4. When n is 2 or more, $X^1$ may be the same as or different from each other. In a case where $A^1$ to $A^4$ are all carbon atoms, that is, in the case of Formula (a), n is an integer of 0 to 4. In a case where any one of $A^1$ to $A^4$ is a nitrogen atom, that is, in the case of Formulas (b) to (e), n is an integer of 0 to 3.

n is preferably 0 to 2, more preferably 0 or 1.

When n is 2 or more, two $X^1$ may be taken together to form a ring.

In Formula (I), $R^1$ represents an unsubstituted or substituted C1-6 alkylthio group, an unsubstituted or substituted C1-6 alkylsulfinyl group, or an unsubstituted or substituted C1-6 alkylsulfonyl group, a C1-6 alkylsulfoxyimino group or a group represented by $-S(=O)(=N-R^a)-R^b$. Here, $R^a$ represents a hydrogen atom, a cyano group, a C1-6 alkyl group, or an unsubstituted or substituted C1-6 alkylcarbonyl group, and $R^b$ represents a C1-6 alkyl group.

Examples of the "C1-6 alkylthio group", the "C1-6 alkylsulfinyl group", and the "C1-6 alkylsulfonyl group" and groups in which a substituent is included in these groups as $R^1$ include the same groups as those that are exemplified as $X^1$.

Examples of the "C1-6 alkylsulfoxyimino group" include an S,S-dimethylsulfoxyimino group.

Examples of the "C1-6 alkyl group" and the "C1-6 alkylcarbonyl group" as $R^a$ and $R^b$ in the group represented by Formula $-S(=O)(=N-R^a)-R^b$ include the same groups as those that are exemplified as $X^1$. The C1-6 alkylcarbonyl group having a substituent as $R^a$ is preferably a C1-6 haloalkylcarbonyl group.

$R^1$ is preferably a C1-6 alkylthio group, a C1-6 alkylsulfinyl group, a C1-6 alkylsulfonyl group, and particularly preferably a C1-6 alkylsulfonyl group.

In Formula (I), D represents a ring represented by Formula (D-1) or Formula (D-2).

(D-1)

(D-2)

In Formula (D-1) and Formula (D-2), * represents a binding position.

In Formulas (D-1) and (D-2), Q represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C1-6 alkoxycarbonyl group, an unsubstituted or substituted aminocarbonyl group, an unsubstituted or substituted 3- to 6-membered heterocyclyloxycarbonyl group, an unsubstituted or substituted 3- to 6-membered heterocyclyl group, an unsubstituted or substituted allene group, a cyano group, a group represented by —CR$^c$=NO—R$^d$, or a group represented by —N=CR$^e$R$^f$. Here, R$^c$ represents a hydrogen atom, or an unsubstituted or substituted C1-6 alkyl group, R$^d$ represents an unsubstituted or substituted C1-6 alkyl group, or an unsubstituted or substituted phenyl group, R$^e$ and R$^f$ represent a hydrogen atom, an unsubstituted or substituted C1-6 alkyl group, an amino group having a substituent, or a halogeno group.

Examples of the "C1-6 alkyl group", the "C2-6 alkenyl group", the "C2-6 alkynyl group", the "C3-8 cycloalkyl group", the "C1-6 alkylthio group", the "C1-6 alkylsulfinyl group, the "C1-6 alkylsulfonyl group", the "C1-6 alkoxycarbonyl group" and the "3- to 6-membered heterocyclyl group" as Q include the same groups as those that are exemplified as X$^1$.

The "C1-6 alkyl group" as Q is preferably a "C3-6 alkyl group". Examples of the preferable substituent in the "C 3-6 alkyl group" include a C1-6 alkoxy group, a halogeno group, a cyano group, a hydroxyl group, a C1-6 alkylcarbonyloxy group, a C3-8 cycloalkyl group, a C6-10 aryl group, and a 3- to 6-membered heterocyclyl group.

In a case where the "C1-6 alkyl group" is a C1-2 alkyl group, examples of the preferable substituent include an unsubstituted or substituted C1-6 alkoxy group or an unsubstituted or substituted 5- to 6-membered heteroaryloxy group. The substituent of the C1-6 alkoxy group is preferably a halogeno group, and the substituent of the 5- to 6-membered heteroaryloxy group is preferably a halogeno group or a C1-6 haloalkyl group.

Examples of the preferable substituent in the "C2-6 alkenyl group" and "C2-6 alkynyl group" as Q include an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted C1-6 alkoxy group, a formyl group, an unsubstituted or substituted alkylthio group, an unsubstituted or substituted C1-6 alkylcarbonyloxy group, an unsubstituted or substituted C6-12 aryl group, an unsubstituted or substituted 3 to 6-membered heterocyclyl group, a phenylsulfonyl group, a halogeno group, a tri C1-6 alkyl-substituted silyl group, and a cyano group.

Examples of the "unsubstituted or substituted C1-6 alkyl group", the "unsubstituted or substituted C2-6 alkenyl group", the "unsubstituted or substituted C2-6 alkynyl group", the "unsubstituted or substituted C3-8 cycloalkyl group", the "unsubstituted or substituted C1-6 alkoxy group", the "unsubstituted or substituted alkylthio group", the "unsubstituted or substituted C1-6 alkylcarbonyloxy group", "unsubstituted or substituted C6-12 aryl group", and the "unsubstituted or substituted 3- to 6-membered heterocyclyl group" which are the substituents on the "C2-6 alkenyl group" and "C2-6 alkynyl group" as Q include the same groups as those that are exemplified as R$^5$ to R$^8$ in Formulas (IV) and (V).

Examples of the substituent in the "C3-8 cycloalkyl group", the "C1-6 alkylthio group", the "C1-6 alkylsulfinyl group", the "C1-6 alkylsulfonyl group" and the "3- to 6-membered heterocyclyl group" as Q include the same groups as those that are exemplified as the above X$^1$.

Examples of the substituent of the "aminocarbonyl group" as Q include a C1-6 alkyl group, a C1-6 haloalkyl group, a C1-6 alkylcarbonyl group, and a C6-12 aryl group.

In the case of the disubstituted aminocarbonyl group, two substituents may be taken together to form a ring.

Examples of the "allene group" as Q include 1,2-propadiene. Examples of the preferable substituent in the "allene group" as Q include a C1-6 haloalkyl group, and a halogeno group.

Examples of the "3- to 6-membered heterocyclyloxycarbonyl group" as Q include 1H-benzo[d][1,2,3]triazol-1-yloxycarbonyl.

Examples of the preferable substituents in the "3- to 6-membered heterocyclyloxycarbonyl group" as Q include the same groups as those that are exemplified for the 3- to 6-membered heterocyclyl group.

Examples of the "C1-6 alkyl group" as R$^c$ and R$^d$ in the group represented by Formula: —CR$^c$=NO—R$^d$ and groups in which a substituent is included in these groups include the same groups as those that are exemplified in the above X$^1$.

Examples of the preferable substituent in the "phenyl group" as R$^d$ include a C1-6 alkyl group, a C1-6 haloalkyl group, a hydroxyl group, a C1-6 alkoxy group, a C1-6 haloalkoxy group, a halogeno group, a cyano group, and a nitro group.

Examples of the "C1-6 alkyl group" and the "amino group" as R$^e$ and R$^f$ in the group represented by Formula: —N=CR$^e$R$^f$, and groups in which a substituent is included in these groups include the same groups as those that are exemplified as X$^1$.

Examples of the "halogeno group" as R$^e$ and R$^f$ in the group represented by Formula: —N=CR$^e$R$^f$ include the same as those that are exemplified as X$^1$ Q is preferably a group represented by Formula (IV), a group represented by Formula (V) or a cyano group.

In Formula (IV) and Formula (V), * represents a binding position.

In Formulas (IV) and (V), R$^5$ to R$^8$ each independently represents a hydrogen atom, an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted C1-6 alkoxy group, a formyl group, an unsubstituted or substituted alkylthio group, an unsubstituted or substituted C1-6 alkyl carbonyloxy group, an unsubstituted or substituted C6-12 aryl group, an unsubstituted or substituted 3- to 6-membered heterocyclyl group, an unsubstituted or substituted phenylsulfonyl group, a halogeno group, a tri C1-6 alkyl substituted silyl group or a cyano group.

Examples of the "C1-6 alkyl group", the "C2-6 alkenyl group", the "C2-6 alkynyl group", the "C3-8 cycloalkyl group", the "C1-6 alkoxy group", the "C1-6 alkylthio", the "C6-12 aryl group", the "3- to 6-membered heterocyclyl group", and the "halogeno group" as R⁵ to R⁸ are the same as those that are exemplified as X¹.

Examples of the preferable substituents in the "C1-6 alkyl group", the "C2-6 alkenyl group", the "C2-6 alkynyl group", the "C3-8 cycloalkyl group", the "C1-6 alkoxy group", the "C1-6 alkylthio" as R⁵ to R⁸ include a C1-6 alkoxy group, a C1-6 haloalkoxy group, a C3-8 cycloalkyl group, a C1-6 alkylcarbonyloxy group, a halogeno group, a cyano group, a hydroxyl group, a C6-10 aryl group, and a 3- to 6-membered heterocyclyl group.

Examples of the preferable substituent in the "C6-12 aryl group" and the "3- to 6-membered heterocyclyl group" as R⁵ to R⁸ include a halogeno group, a C1-6 alkyl group, a C1-6 haloalkyl group, a C1-6 alkoxy group, and a C1-6 haloalkoxy groups.

Examples of the "C1-6 alkylcarbonyloxy group" as R⁵ to R⁸ include an acetyloxy group and a propionyloxy group.

Examples of the substituent in the "C1-6 alkylcarbonyloxy group" as R⁵ to R⁸ include a halogeno group such as a fluoro group, a chloro group, a bromo group, and an iodo group; C1-6 alkoxy groups such as a methoxy group, an ethoxy group, an n-propoxy group, an i-propoxy group, an n-butoxy group, an s-butoxy group, an i-butoxy group, and a t-butoxy group; C1-6 haloalkoxy groups such as a 2-chloro-n-propoxy group, a 2,3-dichlorobutoxy group, and a trifluoromethoxy group; C6-10 aryl group such as a phenyl group and a naphthyl group; and a cyano group.

Examples of the tri-C1-6 alkyl-substituted silyl group as R⁵ to R⁸ include a trimethylsilyl group, and a triethylsilyl group.

As R⁵ to R⁸, a hydrogen atom, an unsubstituted or substituted C1-6 alkyl group (preferably C1-6 haloalkyl group), an unsubstituted or substituted C2-6 alkenyl group (preferably C2-6 haloalkenyl group), an unsubstituted or substituted C2-6 alkynyl group (preferably C2-6 haloalkynyl group), a C1-6 alkoxy group, a C1-6 alkylcarbonyloxy group, a halogeno group, or a cyano group is preferable, and a hydrogen atom, a C1-6 haloalkyl group, or a halogeno group is more preferable.

Particularly, R⁵ is preferably a hydrogen atom, a C1-6 haloalkyl group or a halogeno group, R⁶ is preferably a C1-6 haloalkyl group or a halogeno group, and R⁷ is preferably a hydrogen atom, and R⁸ is preferably a haloalkyl group.

In Formula (D-1), B¹ and B² each independently represents a nitrogen atom or CR³. When B¹ and B² are both CR³, the two R³'s may be the same or different.

In Formula (D-1), R² is a substituent bound to any one nitrogen atom of the nitrogen atom of the azole ring of Formula (D-1). R² is not a substituent on the nitrogen atom of Q.

R² represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, or an unsubstituted or substituted C1-6 alkylsulfonyl group.

Examples of the "C1-6 alkyl group", the "C2-6 alkenyl group", the "C2-6 alkynyl group", the "C3-8 cycloalkyl group", the "C1-6 alkoxy group", the "C1-6 alkylcarbonyl group", the "C1-6 alkoxycarbonyl group", the "C1-6 alkylsulfonyl group", and the groups having a substituent in these groups as R² include the same as those that are exemplified as X¹.

As R², a C1-6 alkyl group is preferable, and a methyl group is particularly preferable.

In Formula (D-1), R³ represents a hydrogen atom, an unsubstituted or substituted C1-6 alkyl group, an unsubstituted or substituted a C2-6 alkenyl group, an unsubstituted or substituted C2-6 alkynyl group, an unsubstituted or substituted C3-8 cycloalkyl group, a halogeno group, a cyano group, or a nitro group.

Examples of the "C1-6 alkyl group", the "C2-6 alkenyl group", the "C2-6 alkynyl group", and the "C3-8 cycloalkyl group" as R³ and the group having a substituent on these groups include the same as those that are exemplified as X¹.

Examples of the "halogeno group" as R³ include the same as those that are exemplified as X¹.

R³ is preferably a hydrogen atom, a C1-6 alkyl group or a halogeno group, and particularly preferably a hydrogen atom.

In Formula (D-2), B³ and B⁴ each independently represents a nitrogen atom or a carbon atom. However, B³ and B⁴ are not carbon atoms at the same time.

In Formula (D-2), R⁴ represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted amino group, a halogeno group, a cyano group, or a nitro group.

Examples of the "C1-6 alkyl group", the "C2-6 alkenyl group", the "C2-6 alkynyl group", the "C3-8 cycloalkyl group", the "amino group", and the groups having a substituent in these groups as R⁴ include the same as those that are exemplified as X¹.

Examples of the "halogeno group" as R⁴ include the same as those that are exemplified as X¹.

In Formula (D-2), m represents the number of chemically acceptable R⁴ and is an integer of 0 to 2. When m is 2 or more, R⁴ may be the same as or different from each other.

m is preferably 1.

In Formula (I), D is represented by Formula (D-1) or Formula (D-2), which means that Formula (I) is represented by Formula (II) or Formula (III).

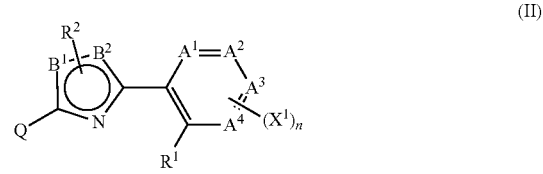

(II)

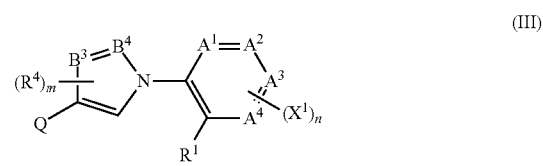

(III)

In Formula (II), A¹ to A⁴, X¹, n and R¹ have the same meanings as those in Formula (I), and B¹, B², R² and Q have the same meanings as those in Formula (D-1).

That is, Formula (II) is represented by Formulas (f) to (h).

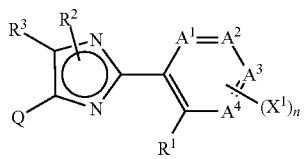
(f)

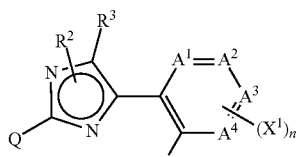
(g)

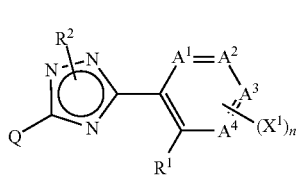
(h)

In Formulas (f) to (h), $A^1$ to $A^4$, $X^1$, n and $R^1$ have the same meanings as those in Formula (I), and $R^2$, $R^3$ and Q have the same meanings as those in Formula (D-1).

In addition, Formula (II) is more specifically represented by Formulas (i) to (q).

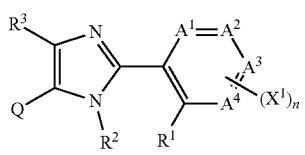
(i)

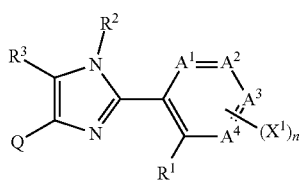
(j)

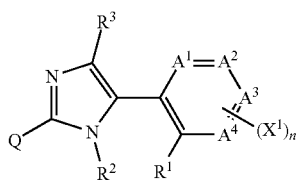
(k)

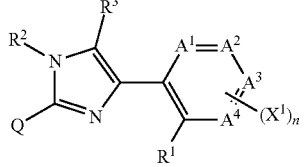
(m)

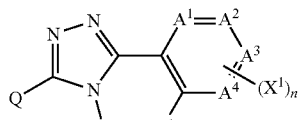
(n)

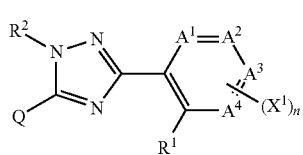
(o)

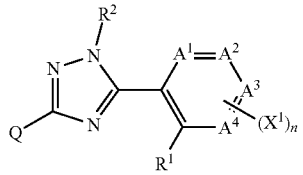
(p)

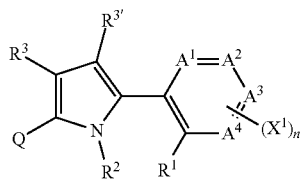
(q)

In Formulas (i) to (q), $A^1$ to $A^4$, $X^1$, n and $R^1$ have the same meanings as those in Formula (I), and $R^2$, $R^3$ and Q have the same meanings as those in Formula (D-1). In Formula (q), $R^{3'}$ has the same meaning as $R^3$.

The compound of the present invention represented by Formula (II) is preferably a compound of Formula (i), Formula (j), Formula (k), Formula (m), Formula (n) or Formula (p) and more preferably a compound of Formula (i) and Formula (j).

In Formula (III), $A^1$ to $A^4$, $X^1$, n and $R^1$ have the same meanings as those in Formula (I), and $B^3$, $R^4$, $R^4$, m and Q have the same as those in Formula (D-2).

That is, Formula (III) is represented by Formulas (r) to (t).

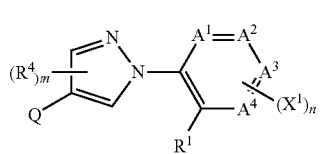
(r)

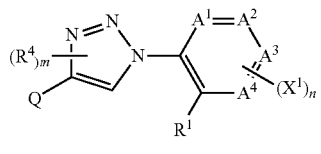
(s)

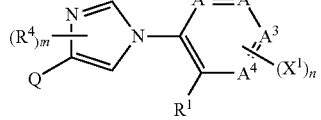
(t)

In Formulas (r) to (t), $A^1$ to $A^4$, $X^1$, n and $R^1$ have the same meanings as those in Formula (I), $R^4$, m and Q are the same as those in Formula (D-2).

The compound of the present invention represented by Formula (III) is preferably represented by Formula (r).

The compound of the present invention is particularly preferably represented by Formulas (i) or (r).

There is no particular limitation on the salt of Compound (I) as long as the compound is agriculturally and horticulturally acceptable salt. Examples of the salt of Compound (I) include salts of inorganic acids such as hydrochloric acid and sulfuric acid; salts of organic acids such as acetic acid and lactic acid; salts of alkali metals such as lithium, sodium, and potassium; salts of alkaline earth metals such as calcium and magnesium; salts of transition metals such as iron and copper; and salts of organic bases such as ammonia, triethylamine, tributylamine, pyridine, and hydrazine.

There is no particular limitation on the production method of Compound (I) or the salt thereof. Further, the salt of Compound (I) may be obtained by Compound (I) by any known conventional method. For example, the salt of Compound (I) or Compound (I) of the present invention may be obtained by any known conventional production method described in Examples or the like.

[Production Intermediate]

The compounds represented by Formulas (VI) and (VII) are useful as intermediates for the preparation of the compounds of the present invention.

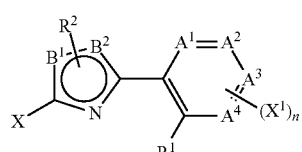

(VI)

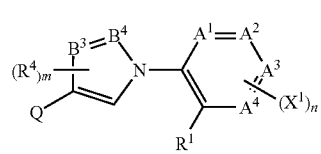

(VII)

In Formulas (VI) and (VII), $A^1$ to $A^4$, $X^1$, n, $R^1$, $R^2$, $R^4$, m and $B^1$ to $B^4$ are the same as those in Formulas (II) and (III), and X represents a halogeno group.

The arylazole compound of the present invention is excellent in the control effect of pests such as various agricultural pests and mites affecting the growth of plants.

In addition, the arylazole compound of the present invention is highly safe exhibiting no phytotoxicity to crops and low toxicity to fish and warm-blooded animals, and thus can be effectively utilized as an active ingredient of insecticide or acaricide.

Furthermore, in recent years, many insect pests such as diamondback moth, white-backed plant hopper, leafhopper, aphids have developed resistances to various existing agricultural chemicals, causing problems of insufficient efficacy of these chemical agent, and thus chemical agent effective against chemically resistant insect pests have been desired. The arylazole compound of the present invention has an excellent controlling effect not only on chemically sensitive insect pests but also on chemically resistant insect pests, and even further on acaricide-resistant mites.

The arylazole compound of the present invention is excellent in the control effect of ectoparasites and endoparasites which are harmful to humans and animals. In addition, the arylazole compound is highly safe exhibiting low toxicity to fish and warm-blooded animals, and thus can effectively utilized as an active ingredient of a controlling agent for ectoparasites and endoparasites.

The arylazole compound according to the present invention shows efficacy in all developmental stages of organisms to be controlled, and exhibits excellent control effects against eggs, nymphs, larvae, pupae, and adults of mites and insects.

[Pest Control Agent, Insecticide, or Acaricide]

The pest control agent, insecticide, or acaricide according to the present invention contains at least one selected from the group consisting of the arylazole compounds according to the present invention, as an active ingredient thereof. There are no particular limitations on the amount of the arylazole compound contained in the pest control agent, insecticide, or acaricide according to the present invention provided that the pest control effects are exhibited.

It is preferable that the pest control agent, insecticide, or acaricide according to the present invention be applied to cereals; vegetables; root vegetables; potatoes; fruit-bearing trees, trees of tea, coffee, or cacao; feed crops; lawn grasses; or plants such as cotton.

In the application to plants, the pest control agent, insecticide, or acaricide according to the present invention may be applied to any of leaf, stem, stalk, flower, bud, fruit, seed, sprout, root, tuber, tuberous root, shoot, or slip.

There are no particular limitations on the species of the plant to be applied with the pest control agent, insecticide, or acaricide of the present invention. The plant species may be any of original species, varieties, improved varieties, cultivars, mutants, hybrid bodies, gene recombinants (GMO), and the like.

The pest control agent according to the present invention may be used to control various agricultural pests and mites by conducting seed treatment, foliage application, soil application, or submerged application.

Typical examples of agricultural pests and mites to be controlled with the pest control agent according to the present invention are as shown below.

(1) Butterflies and moths of the order Lepidoptera
   (a) moths of the family Arctiidae, such as *Hyphantria cunea*, and *Lemyra imparilis*;
   (b) moths of the family Bucculatricidae, such as *Bucculatrix pyrivorella*;
   (c) moths of the family Carposinidae, such as *Carposina sasakii*;
   (d) moths of the family Crambidae, such as *Diaphania indica*, and *Diaphania nitidalis*, of *Diaphania* spp.; *Ostrinia furnacalis*, *Ostrinia nubilalis*, and *Ostrinia scapulalis*, of *Ostrinia* spp.; and others such as *Chilo suppressalis*, *Cnaphalocrocis medinalis*, *Conogethes punctiferalis*, *Diatraea grandiosella*, *Glyphodes pyloalis*, *Hellula undalis*, and *Parapediasia teterrella*;
   (e) moths of the family Gelechiidae, such as *Helcystogramma triannulella*, *Pectinophora gossypiella*, *Phthorimaea operculella*, and *Sitotroga cerealella*;
   (f) moths of the family Geometridae, such as *Ascotis selenaria*;
   (g) moths of the family Gracillariidae, such as *Caloptilia theivora*, *Phyllocnistis citrella*, and *Phyllonorycter ringoniella*;
   (h) butterflies of the family Hesperiidae, such as *Parnara guttata*;
   (i) butterflies of the family Lasiocampidae, such as *Malacosoma neustria*;

(j) moths of the family Lymantriidae, such as *Lymantria dispar*, and *Lymantria monacha*, of *Lymantria* spp.; and others such as *Euproctis pseudoconspersa*, and *Orgyia thyellina*;

(k) moths of the family Lyonetiidae, such as *Lyonetia clerkella*, and *Lyonetia prunifoliella malinella*, of *Lyonetia* spp.;

(l) moths of the family Noctuidae, such as *Spodoptera depravata*, *Spodoptera eridania*, *Spodoptera exigua*, *Spodoptera frugiperda*, *Spodoptera littoralis*, and *Spodoptera litura*, of *Spodoptera* spp.; *Autographa gamma*, and *Autographa nigrisigna*, of *Autographa* spp.; *Agrotis ipsilon*, and *Agrotis segetum*, of *Agrotis* spp.; *Helicoverpa armigera*, *Helicoverpa assulta*, and *Helicoverpa zea*, of *Helicoverpa* spp.; *Heliothis armigera*, and *Heliothis virescens*, of *Heliothis* spp.; and others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens*, and *Trichoplusia ni*;

(m) moths of the family Nolidae, such as *Earias insulana*;

(n) butterflies of the family Pieridae, such as *Pieris brassicae*, and *Pieris rapae crucivora*, of *Pieris* spp.;

(o) moths of the family Plutellidae, such as *Acrolepiopsis sapporensis*, and *Acrolepiopsis suzukiella*, of *Acrolepiopsis* spp.; and others such as *Plutella xylostella*;

(p) moths of the family Pyralidae, such as *Cadra cautella*, *Elasmopalpus lignosellus*, *Etiella zinckenella*, and *Galleria mellonella*;

(q) moths of the family Sphingidae, such as *Manduca quinquemaculata*, and *Manduca sexta*, of *Manduca* spp.;

(r) moths of the family Stathmopodidae, such as *Stathmopoda masinissa*;

(s) moths of the family Tineidae, such as *Tinea translucens*;

(t) moths of the family Tortricidae, such as *Adoxophyes honmai*, and *Adoxophyes orana*, of *Adoxophyes* spp.; *Archips breviplicanus*, and *Archips fuscocupreanus* of *Archips* spp.; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana*, and *Sparganothis pilleriana*; and (u) moths of the family Yponomeutidae, such as *Argyresthia conjugella*.

(2) Pests of the order Thysanoptera (a) pests of the family Phlaeothripidae, such as *Ponticulothrips diospyrosi*; and (b) pests of the family Thripidae, such as *Frankliniella intonsa*, and *Frankliniella occidentalis*, of *Frankliniella* spp.; *Thrips palmi*, and *Thrips tabaci*, of *Thrips* spp.; and others such as *Heliothrips haemorrhoidalis*, and *Scirtothrips dorsalis*.

(3) Pests of the order Hemiptera (A) The suborder Archaeorrhyncha (a) pests of the family Delphacidae, such as *Laodelphax striatella*, *Nilaparvata lugens*, *Perkinsiella saccharicida*, and *Sogatella furcifera*.

(B) The suborder Clypeorrhyncha (a) pests of the family Cicadellidae, such as *Empoasca fabae*, *Empoasca nipponica*, *Empoasca onukii*, and *Empoasca sakaii*, of *Empoasca* spp.; and others such as *Arboridia apicalis*, *Balclutha saltuella*, *Epiacanthus stramineus*, *Macrosteles striifrons*, and *Nephotettix cinctinceps*.

(C) The suborder Heteroptera (a) pests of the family Alydidae, such as *Riptortus clavatus*;

(b) pests of the family Coreidae, such as *Cletus punctiger*, and *Leptocorisa chinensis*;

(c) pests of the family Lygaeidae, such as *Blissus leucopterus*, *Cavelerius saccharivorus*, and *Togo hemipterus*;

(d) pests of the family Miridae, such as *Halticus insularis*, *Lygus lineolaris*, *Psuedatomoscelis seriatus*, *Stenodema sibiricum*, *Stenotus rubrovittatus*, and *Trigonotylus caelestialium*;

(e) pests of the family Pentatomidae, such as *Nezara antennata*, and *Nezara viridula*, of *Nezara* spp.; *Eysarcoris aeneus*, *Eysarcoris lewisi*, and *Eysarcoris ventralis*, of *Eysarcoris* spp., and others such as *Dolycoris baccarum*, *Eurydema rugosum*, *Glaucias subpunctatus*, *Halyomorpha halys*, *Piezodorus hybneri*, *Plautia crossota*, and *Scotinophora lurida*;

(f) pests of the family Pyrrhocoridae, such as *Dysdercus cingulatus*;

(g) pests of the family Rhopalidae, such as *Rhopalus msculatus*;

(h) pests of the family Scutelleridae, such as *Eurygaster integriceps*); and (i) pests of the family Tingidae, such as *Stephanitis nashi*.

(D) The suborder Sternorrhyncha (a) pests of the family Adelgidae, such as *Adelges laricis*;

(b) pests of the family Aleyrodidae, such as *Bemisia argentifolii*, and *Bemisia tabaci*, of *Bemisia* spp.; and others such as *Aleurocanthus spiniferus*, *Dialeurodes citri*, and *Trialeurodes vaporariorum*;

(c) pests of the family Aphididae, such as *Aphis craccivora*, *Aphis fabae*, *Aphis forbesi*, *Aphis gossypii*, *Aphis pomi*, *Aphis sambuci*, and *Aphis spiraecola*, of *Aphis* spp.; *Rhopalosiphum maidis*, and *Rhopalosiphum padi*, of *Rhopalosiphum* spp.; *Dysaphis plantaginea*, and *Dysaphis radicola*, of *Dysaphis* spp.; *Macrosiphum avenae*, and *Macrosiphum euphorbiae*, of *Macrosiphum* spp.; *Myzus cerasi*, *Myzus persicae*, and *Myzus varians*, of *Myzus* spp.; and others such as *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodon humuli*, *Schizaphis graminum*, *Sitobion avenae*, and *Toxoptera aurantii*;

(d) pests of the family Coccidae, such as *Ceroplastes ceriferus*, and *Ceroplastes rubens*, of *Ceroplastes* spp.;

(e) pests of the family Diaspididae, such as *Pseudaulacaspis pentagona*, and *Pseudaulacaspis prunicola*, of *Pseudaulacaspis* spp.; *Unaspis euonymi*, and *Unaspis yanonensis*, of *Unaspis* spp.; and others such as *Aonidiella aurantii*, *Comstockaspis perniciosa*, *Fiorinia theae*, and *Pseudaonidia paeoniae*;

(f) pests of the family Margarodidae, such as *Drosicha corpulenta*, and *Icerya purchasi*;

(g) pests of the family Phylloxeridae, such as *Viteus vitifolii*;

(h) pests of the family Pseudococcidae, such as *Planococcus citri*, and *Planococcus kuraunhiae*, of *Planococcus* spp.; and others such as *Phenacoccus solani*, and *Pseudococcus comstocki*; and (i) pests of the family Psyllidae, such as *Psylla mali*, and *Psylla pyrisuga*, of *Psylla* spp.; and other such as *Diaphorina citri*.

(4) Pests of the suborder *Polyphaga*

(a) pests of the family Anobiidae, such as *Lasioderma serricorne*;

(b) pests of the family Attelabidae, such as *Byctiscus betulae*, and *Rhynchites heros*;

(c) pests of the family Bostrichidae, such as *Lyctus brunneus*;

(d) pests of the family Brentidae, such as *Cylas formicarius*;

(e) pests of the family Buprestidae, such as *Agrilus sinuatus*;

(f) pests of the family Cerambycidae, such as *Anoplophora malasiaca*, *Monochamus alternatus*, *Psacothea hilaris*, and *Xylotrechus pyrrhoderus*;

(g) pests of the family Chrysomelidae, such as *Bruchus pisorum*, and *Bruchus rufimanus*, of *Bruchus* spp.; *Diabrotica barberi*, *Diabrotica undecimpunctata*, and *Diabrotica virgifera*, of *Diabrotica* spp.; *Phyllotreta nemorum*, and *Phyllotreta striolata*, of *Phyllotreta* spp.; and others such as *Aulacophora femoralis*, *Callosobruchus chinensis*, *Cassida nebulosa*, *Chaetocnema concinna*, *Leptinotarsa decemlineata*, *Oulema oryzae*, and *Psylliodes angusticollis*;

(h) pests of the family Coccinellidae, such as *Epilachna varivestis*, and *Epilachna vigintioctopunctata*, of *Epilachna* spp.;

(i) pests of the family Curculionidae, such as *Anthonomus grandis*, and *Anthonomus pomorum*, of *Anthonomus* spp.; *Sitophilus granarius*, and *Sitophilus zeamais*, of *Sitophilus* spp.; and others such as *Echinocnemus squameus*, *Euscepes postfasciatus*, *Hylobius abietis*, *Hypera postica*, *Lissohoptrus oryzophilus*, *Otiorhynchus sulcatus*, *Sitona lineatus*, and *Sphenophorus venatus*;

(j) pests of the family Elateridae, such as *Melanotus fortnumi*, and *Melanotus tamsuyensis*, of *Melanotus* spp.;

(k) pests of the family Nitidulidae, such as *Epuraea domina*;

(l) pests of the family Scarabaeidae, such as *Anomala cuprea*, and *Anomala rufocuprea*, of *Anomala* spp.; and others such as *Cetonia aurata*, *Gametis jucunda*, *Heptophylla picea*, *Melolontha melolontha*, and *Popillia japonica*;

(m) pests of the family Scolytidae, such as *Ips typographus*;

(n) pests of the family Staphylinidae, such as *Paederus fuscipes*;

(o) pests of the family Tenebrionidae, such as *Tenebrio molitor*, and *Tribolium castaneum*; and (p) pests of the family Trogossitidae, such as *Tenebroides mauritanicus*.

(5) Pests of the order Diptera (A) The suborder Brachycera (a) pests of the family Agromyzidae, such as *Liriomyza bryoniae*, *Liriomyza chinensis*, *Liriomyza sativae*, and *Liriomyza trifolii*, of *Liriomyza* spp.; and others such as *Chromatomyia horticola*, and *Agromyza oryzae*;

(b) pests of the family Anthomyiidae, such as *Delia platura*, and *Delia radicum*, of *Delia* spp.; and others such as *Pegomya cunicularia*;

(c) pests of the family Drosophilidae, such as *Drosophila melanogaster*, and *Drosophila suzukii*, of *Drosophila* spp.;

(d) pests of the family Ephydridae, such as *Hydrellia griseola*;

(e) pests of the family Psilidae, such as *Psila rosae*; and (f) pests of the family Tephritidae, such as *Bactrocera cucurbitae*, and *Bactrocera dorsalis*, of *Bactrocera* spp.; *Rhagoletis cerasi*, and *Rhagoletis pomonella*, of *Rhagoletis* spp.; and others such as *Ceratitis capitata*, and *Dacus oleae*.

(B) The suborder Nematocera (a) pests of the family Cecidomyiidae, such as *Asphondylia yushimai*, *Contarinia sorghicola*, *Mayetiola destructor*, and *Sitodiplosis mosellana*.

(6) Pest of the order Orthoptera (a) pests of the family Acrididae, such as *Schistocerca americana*, and *Schistocerca gregaria*, of *Schistocerca* spp.; and others such as *Chortoicetes terminifera*, *Dociostaurus maroccanus*, *Locusta migratoria*, *Locustana pardalina*, *Nomadacris septemfasciata*, and *Oxya yezoensis*;

(b) pests of the family Gryllidae, such as *Acheta domestica*, and *Teleogryllus emma*;

(c) pests of the family Gryllotalpidae, such as *Gryllotalpa orientalis*; and (d) pests of the family Tettigoniidae, such as *Tachycines asynamorus*.

(7) Mites (Acari)

(A) Acaridida of the order Astigmata (a) mites of the family Acaridae, such as *Rhizoglyphus echinopus*, and *Rhizoglyphus robini*, of *Rhizoglyphus* spp.; *Tyrophagus neiswanderi*, *Tyrophagus perniciosus*, *Tyrophagus putrescentiae*, and *Tyrophagus similis*, of *Tyrophagus* spp.; and others such as *Acarus siro*, *Aleuroglyphus ovatus*, and *Mycetoglyphus fungivorus*;

(B) Actinedida of the order Prostigmata (a) mites of the family Tetranychidae, such as *Bryobia praetiosa*, and *Bryobia rubrioculus*, of *Bryobia* spp.; *Eotetranychus asiaticus*, *Eotetranychus boreus*, *Eotetranychus celtis*, *Eotetranychus geniculatus*, *Eotetranychus kankitus*, *Eotetranychus pruni*, *Eotetranychus shii*, *Eotetranychus smithi*, *Eotetranychus suginamensis*, and *Eotetranychus uncatus*, of *Eotetranychus* spp.; *Oligonychus hondoensis*, *Oligonychus ilicis*, *Oligonychus karamatus*, *Oligonychus mangiferus*, *Oligonychus orthius*, *Oligonychus perseae*, *Oligonychus pustulosus*, *Oligonychus shinkajii*, and *Oligonychus ununguis*, of *Oligonychus* spp.; *Panonychus citri*, *Panonychus mori*, and *Panonychus ulmi*, of *Panonychus* spp.; *Tetranychus cinnabarinus*, *Tetranychus kanzawai*, *Tetranychus ludeni*, *Tetranychus quercivorus*, *Tetranychus phaselus*, *Tetranychus urticae*, and *Tetranychus viennensis*, of *Tetranychus* spp.; *Aponychus corpuzae*, and *Aponychus firmianae*, of *Aponychus* spp.; *Sasanychus akitanus*, and *Sasanychus pusillus*, of *Sasanychus* spp.; *Shizotetranychus celarius*, *Shizotetranychus longus*, *Shizotetranychus miscanthi*, *Shizotetranychus recki*, and *Shizotetranychus schizopus*, of *Shizotetranychus* spp.; and others such as *Tetranychina harti*, *Tuckerella pavoniformis*, and *Yezonychus sapporensis*;

(b) mites of the family Tenuipalpidae, such as *Brevipalpus lewisi*, *Brevipalpus obovatus*, *Brevipalpus phoenicis*, *Brevipalpus russulus*, and *Brevipalpus californicus*, of *Brevipalpus* spp.; *Tenuipalpus pacificus*, and *Tenuipalpus zhizhilashviliae*, of *Tenuipalpus* spp.; and others such as *Dolichotetranychus floridanus*;

(c) mites of the family Eriophyidae, such as *Aceria diospyri*, *Aceria ficus*, *Aceria japonica*, *Aceria kuko*, *Aceria paradianthi*, *Aceria tiyingi*, *Aceria tulipae*, and

*Aceria zoysiea,* of *Aceria* spp.; *Eriophyes chibaensis,* and *Eriophyes emarginatae,* of *Eriophyes* spp.; *Aculops lycopersici,* and *Aculops pelekassi,* of *Aculops* spp.; *Aculus fockeui,* and *Aculus schlechtendali,* of *Aculus* spp.; and others such as *Acaphylla theavagrans, Calacarus carinatus, Colomerus vitis, Calepitrimerus vitis, Epitrimerus pyri, Paraphytoptus kikus, Paracalacarus podocarpi,* and *Phyllocotruta citri;*

(d) mites of the family Transonemidae, such as *Tarsonemus bilobatus,* and *Tarsonemus waitei,* of *Tarsonemus* spp.; and others such as *Phytonemus pallidus,* and *Polyphagotarsonemus latus;* and (e) mites of the family Penthaleidae, such as *Penthaleus erythrocephalus,* and *Penthaleus* major, of *Penthaleus* spp.

The pest control agent, insecticide or acaricide according to the present invention may further contain additional components except for the arylazole compound according to the present invention. Examples of the additional components include conventional carriers available for Formulation. Examples of other additional components include conventional fungicides, insecticides, acaricides, nematicides, pestisides for earth pest, plant regulating agents, synergists, fertilizers, soil improvement agents, and animal feeds. There are cases where synergistic effects are exhibited by containing such additional components.

Specific examples of the insecticides, acaricides, nematicides, pesticides for earth pest, and anthelmintic agents which can be mixed or used with the pest control agent according to the present invention are as shown below.

(1) Acetylcholinesterase inhibitors:

(a) carbamates: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, chloethocarb, metam sodium, and promecarb; and (b) organic phosphorus-based: acephate, azamethiphos, azinphos-ethyl, azinphos-methyl, cadusafos, chloroethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion; bromophos-ethyl, BRP, carbophenothion, cyanofenphos, CYAP, demeton-S methyl sulfone, dialifos, dichlofenthion, dioxabenzofos, etrimfos, fensulfothion, flupyrazofos, fonofos, formothion, phosmethylan, isazophos, iodofenphos, methacrifos, pirimiphos-ethyl, phosphocarb, propaphos, prothoate, and sulprophos.

(2) GABAergic chloride ion channel antagonists: acetoprole, chlordene, endosulfan, ethiprole, fipronil, pyrafluoprole, pyriprole; and camphlechlor, heptachlor, and dienochlor.

(3) Sodium channel modulators: acrinathrin, d-cis-trans allethrin, d-trans allethrin, bifenthrin, bioallethrin, bioallethrin S-cyclopentyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin; allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, and flupyradifurone.

(5) Nicotinic acetylcholine receptor allosteric modulators: spinetoram, and spinosad.

(6) Chloride channel activators: abamectin, emamectin benzoate, lepimectin, milbemectin; ivermectin, selamectin, doramectin, eprinomectin, moxidectin, milbemycin, and milbemycin oxime.

(7) Juvenile hormone-like substances: hydroprene, kinoprene, methoprene, fenoxycarb, pyriproxyfen; diofenolan, epofenonane, and triprene.

(8) Other non-specific inhibitors: methyl bromide, chloropicrin, sulfuryl fluoride, borax, and tartar emetic.

(9) Homoptera selective feeding inhibitors: flonicamid, pymetrozine, and pyrifluquinazon.

(10) Mite growth inhibitors: clofentezine, diflovidazin, hexythiazox, and etoxazole.

(11) Midgut inner membrane disrupting agent derived from microorganisms: *Bacillus thuringiensis* subspecies Isuraerenshi, *Bacillus sphaericus, Bacillus thuringiensis* sub sp. Aizawai, *Bacillus thuringiensis* subspecies Kurstaki, *Bacillus thuringiensis* subspecies Tenebrionis, and Bt crop protein: Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondrial ATP biosynthetic enzyme inhibitors: diafenthiuron, azocyclotin, cyhexatin, fenbutatin oxide, propargite, and tetradifon.

(13) Oxidative phosphorylation uncouplers: chlorfenapyr, sulfluramid, DNOC, binapacryl, dinobuton, and dinocap.

(14) Nicotinic acetylcholine receptor channel blockers: bensultap, cartap hydrochloride, nereistoxin, thiosultap sodium, and thiocyclam.

(15) Chitin synthesis inhibitors: bistrifluron, chlorfluazuron, diflubenzuron, flucycloxuron, flufenoxuron, hexaflumuron, lufenuron, novaluron, and noviflumuron, teflubenzuron, triflumuron, buprofezin, and fluazuron.

(16) Diptera molting disrupting agents: cyromazine.

(17) Molting hormone receptor agonists: chromafenozide, halofenozide, methoxyfenozide, and tebufenozide.

(18) Octopamine receptor agonists: amitraz, demiditraz, and chlordimeform.

(19) Mitochondrial electron transport system complex III inhibitors: acequinocyl, fluacrypyrim, and hydramethylnon.

(20) Mitochondrial electron transport chain complex I inhibitors: fenazaquin, fenpyroximate, pyrimidifen, pyridaben, tebufenpyrad, tolfenpyrad, and rotenone.

(21) Voltage-gated sodium channel blockers: indoxacarb, and metaflumizone.

(22) Acetyl CoA carboxylase inhibitors: spirodiclofen, spiromesifen, and spirotetramat.

(23) Mitochondrial electron transport chain complex IV inhibitors: aluminum phosphide, calcium phosphide, phosphine, zinc phosphide, and cyanide.

(24) Mitochondrial electron transport chain complex II inhibitors: cyenopyrafen, cyflumetofen, and pyflubumide.

(25) Ryanodine receptor modulators: chlorantraniliprole, cyantraniliprole, flubendiamide, cyclaniliprole, and tetraniliprole.

(26) Mixed function oxidase inhibitor compounds: piperonyl butoxide.

(27) Latrophilin receptor agonists: depsipeptide, cyclic depsipeptide, 24-membered cyclic depsipeptide, and emodepside.

(28) Other agents (mechanism unknown): azadirachtin, benzoximate, bifenazate, bromopropylate, chinomethionate, cryolite, dicofol, pyridalyl; benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimin, fluphenazine, gossyplure, japonilure, metoxadiazone, petroleum, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide,
5-[5-(3,5-dichlorophenyl)-5-trifluoromethyl-4,5-dihydroisoxazole-3-yl]-2-(1H-1,2,4-triazol-1-yl) benzonitrile (CAS: 943137-49-3), broflanilide, and other meta-diamides.

(29) Anthelmintic agents:
(a) benzimidazole derivatives: fenbendazole, albendazole, triclabendazole, oxibendazole, mebendazole, oxfendazole, parbendazole, flubendazole, febantel, netobimin, thiophanate; thiabendazole, and cambendazole;
(b) salicylanilide derivatives: closantel, oxyclozanide, rafoxanide, and niclosamide;
(c) substituted phenol derivatives: nitroxinil and nitroscanate;
(d) pyrimidine derivatives: pyrantel and morantel;
(e) imidazothiazole derivatives: levamisole and tetramisole;
(f) tetrahydropyrimidine derivatives: praziquantel and epsiprantel; and
(g) other anthelmintic agents: cyclodiene, ryania, clorsulon, metronidazole, demiditraz; piperazine, diethylcarbamazine, dichlorophene, monepantel, tribendimidine, amidantel; thiacetarsamide, melorsamine and arsenamide.

Specific examples of fungicides which can be mixed with or used in combination with the pest control agent of the present invention are as shown below.

(1) Nucleic acid biosynthesis inhibitors:
(a) RNA polymerase I inhibitors: benalaxyl, benalaxyl-M, furalaxyl, metalaxyl, metalaxyl-M, oxadixyl, clozylacon, and ofurace;
(b) adenosine deaminase inhibitors: bupirimate, dimethirimol, and ethirimol;
(c) DNA/RNA synthesis inhibitors: hymexazol and octhilinone; and
(d) DNA topoisomerase II inhibitors: oxolinic acid.

(2) Mitotic inhibitors and cell division inhibitors:
(a) β-tubulin polymerization inhibitors: benomyl, carbendazim, chlorfenazole, fuberidazole, thiabendazole, thiophanate, thiophanate-methyl, diethofencarb, zoxamide, and ethaboxam;
(b) cell division inhibitors: pencycuron; and
(c) spectrin-like protein delocalization inhibitors: fluopicolide.

(3) Respiration inhibitors:
(a) complex I NADH oxidation-reduction enzyme inhibitors:
diflumetorimu and tolfenpyrad;
(b) complex II succinate dehydrogenase inhibitors: benodanil, flutolanil, mepronil, isofetamide, fluopyram; fenfuram, furmecyclox; carboxin, oxycarboxin, thifluzamide, benzovindiflupyr, bixafen, fluxapyroxad, furametpyr, isopyrazam, penflufen, penthiopyrad, sedaxane, boscalid, and pyraziflumide;
(c) complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb; kresoxim-methyl, trifloxystrobin, dimoxystrobin, fenaminstrobin, metominostrobin, orysastrobin; famoxadone, fluoxastrobin, fenamidone, pyribencarb, and mandestrobin;
(d) complex III ubiquinol reductase Qi inhibitors: cyazofamid and amisulbrom;
(e) oxidative phosphorylation uncoupling agents: binapacryl, meptyldinocap, dinocap, fluazinam, and ferimzone;
(f) oxidative phosphorylation inhibitors (ATP synthase inhibitors): fentin acetate, fentin chloride, and fentin hydroxide;
(g) ATP production inhibitors: silthiofam; and
(h) complex III: Qx (unknown) inhibitor of cytochrome bc1 (ubiquinone reductase): ametoctradin.

(4) Amino acid and protein synthesis inhibitors
(a) methionine biosynthesis inhibitors: andoprim, cyprodinil, mepanipyrim, and pyrimethanil; and
(b) protein synthesis inhibitors: blasticidin-S, kasugamycin, kasugamycin hydrochloride, streptomycin, and oxytetracycline.

(5) Signal transduction inhibitors:
(a) signal transduction inhibitors: quinoxyfen and proquinazid; and
(b) MAP/histidine kinase inhibitors in osmotic signal transduction: fenpiclonil, fludioxonil, chlozolinate, iprodione, procymidone, and vinclozolin.

(6) Lipids and cell membrane synthesis inhibitors:
(a) phospholipid biosynthesis, methyltransferase inhibitors: edifenphos, iprobenfos, pyrazophos, and isoprothiolane;
(b) lipid peroxidation agents: biphenyl, chloroneb, dicloran, quintozene, tecnazene, tolclofos-methyl, and etridiazole;
(c) agents that act on cell membranes: iodocarb, propamocarb, propamocarb hydrochloride, propamocarb fosetylate, and prothiocarb;
(d) microorganisms that disrupt cell membranes of pathogens: *Bacillus subtilis* bacteria, *Bacillus subtilis* QST713 strain, *Bacillus subtilis* FZB24 strain, *Bacillus subtilis* MBI600 strain, and *Bacillus subtilis* strain D747; and
(e) agents that disrupt cell membranes: extract of *Melaleuca alternifolia* (tea tree).

(7) Sterol (in cell membrane) biosynthesis inhibitors:
(a) sterol biosynthesis (C14-demethylation) inhibitors: triforine, pyrifenox, pyrisoxazole, fenarimol, flurprimidol, nuarimol, imazalil, imazalil sulfate, oxpoconazole, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole; prothioconazole, voriconazole, and mefentrifluconazole;
  (b) sterol biosynthesis (Δ14 reductase and sterol Δ8→Δ7-isomerase) inhibitors: aldimorph, dodemorph, dodemorph acetate, fenpropimorph, tridemorph, fenpropidin, piperalin, and spiroxamine;
  (c) sterol biosynthesis (3-keto reductase C4-demethylation) inhibitors: fenhexamid and fenpyrazamine; and
  (d) sterol biosynthesis (squalene epoxidase) inhibitors: pyributicarb, naftifin, and terbinafine.
(8) Cell wall synthesis inhibitors
  (a) trehalase inhibitor: validamycin;
  (b) chitin synthase inhibitors: polyoxin, and polyoxorim; and
  (c) cellulose synthase inhibitors: dimethomorph, flumorph, pyrimorph, benthiavalicarb, iprovalicarb, tolprocarb, valifenalate, and mandipropamid.
(9) Melanin biosynthesis inhibitors
  (a) melanin biosynthesis reductase inhibitors: fthalide, pyroquilon, and tricyclazole;
  (b) melanin biosynthesis anhydrase inhibitors: carpropamid, diclocymet, and fenoxanil; and
  (c) others: tolprocarb.
(10) Host plant resistance inducers:
  (a) agents that act on salicylic acid synthesis pathway: acibenzolar-S-methyl; and
  (b) others: probenazole, tiadinil, isotianil, laminarin, giant knotweed extract.
(11) Agents with unidentified mode of action: cymoxanil, fosetyl aluminum, phosphoric acid (phosphate), tecloftalam, triazoxide, flusulfamide, diclomezine, methasulfocarb, cyflufenamid, metrafenone, piriofenon, dodine, dodine free base, and flutianil.
(12) Agents with multiple modes of action: copper (copper salt), bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon; chinomethionate, and fluoroimide.
(13) Other agents: DBEDC, fluoro folpet, guazatine acetate, bis (8-quinolinolato) copper (II), propamidine, chloropicrin, cyprofuram, *agrobacterium*, bethoxazin, diphenylamine, methyl isothiocyanate (MITC), mildiomycin, capsaicin, cufraneb, cyprosulfamide, dazomet, debacarb, dichlorophene, difenzoquat, difenzoquat methyl sulfonate, flumetover, fosetyl calcium, fosetyl sodium, irumamycin, natamycin, nitrothal-isopropyl, oxamocarb, pyrrolnitrin, tebufloquin, tolnifanide, zarilamid, algophase, amicarthiazol, oxathiapiprolin, metiram zinc, benthiazole, trichlamide, uniconazole, mildiomycin, oxyfenthiin, picarbutrazox, fenpicoxamid, dichlobentiazox, and quinofumelin.

Specific examples of plant regulatory agents which can be mixed with or used in combination with the pest control agent of the present invention are as shown below.

Abscisic acid, kinetin, benzylaminopurine, 1,3-diphenyl urea, forchlorfenuron, thidiazuron, chlorfenuron, dihydrozeatin, gibberellin A, gibberellin A4, gibberellin A7, gibberellin A3,1-methylcyclopropane, N-acetyl aminoethoxyvinylglycine (another name: aviglycine), aminooxyacetic acid, silver nitrate, cobalt chloride, IAA, 4-CPA, cloprop, 2,4-D, MCPB, indole-3-butyric acid, dichlorprop, phenothiol, 1-naphthyl acetamide, ethychlozate, cloxyfonac, maleic hydrazide, 2,3,5-triiodo benzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid; ethephon, chlormequat, mepiquat chloride, benzyl adenine, and 5-aminolevulinic acid.

[Ectoparasite Control Agent]

The ectoparasite control agent of the present invention contains at least one selected from the arylazole compounds of the present invention as an active ingredient. The arylazole compound of the present invention is excellent in controlling the ectoparasites that harm humans and animals.

Examples of ectoparasites include mites, lice, fleas, mosquitos, stable flies, and flesh flies.

Examples of host animals to be treated with the ectoparasite control agent of the present invention include warm-blooded animals such as pet animals such as dogs and cats; pet birds; domestic animals such as a cow, horse, pig, and a sheep; and poultries. Other than these, bees, stag beetles and beetles may also be included.

Ectoparasites parasitate in or on host animals, especially warm-blooded animals. In detail, they parasitize on the back, armpits, lower abdomen, inner thigh, or the like of the host animals and obtain nutrition such as blood and dandruff from the animals.

The ectoparasite control agent of the present invention may be applied by any known veterinary method (local, oral, parenteral or subcutaneous administration). Examples of the method thereof include a method of orally administering to an animal in a form of tablet, capsule, feed or the like; a method of administering to an animal by using immersion liquid or suppository, or by injection (intramuscular, subcutaneous, intravenous, intraperitoneal injection, or the like); a method of locally administering an oily or aqueous liquid formulation by spraying, pour-on, spot-on or the like; and a method of kneading an ectoparasite control agent in a resin, shaping the kneaded product into a suitable shape such as a collar, an ear tag or the like, attaching it to an animal and locally administering it.

Specific examples of ectoparasites which can be controlled by the ectoparasite control agent of the present invention are as shown below.

(1) Mites (Acari)
  mites of the family Demanyssidae, mites of the family Macronyssidae, mites of the family Laelapidae, mites of the family Varroidae, mites of the family Argasidae, mites of the family Ixodidae, mites of the family Psoroptidae, mites of the family Sarcoptidae, mites of the family Knemidokoptidae, mites of the family Demodixidae, mites of the family Trombiculidae, and insect parasitic mites such as stag beetle.

(2) The order Phthiraptera
  lice of the family Haematopinidae, lice of the family Linognathidae, pheasant lice of the family Menoponidae, pheasant lice of Philopteridae, pheasant lice of the family Trichodectidae.

(3) The order Siphonaptera
  fleas of the family Pulicidae, for example, *Ctenocephalides canis* and *Ctenocephalides felis*, of *Ctenocephalides* spp.;
  fleas of the family Tungidae, fleas of the family Ceratophyllidae, fleas of the family Leptopsyllidae.

(4) The order Hemiptera (5) Insect pests of the order Diptera
  mosquitos of the family Culicidae, black flies of the family Simuliidae, biting midges of the family Ceratopogonidae, horseflies of the family Tabanidae, flies of the family Muscidae, tsetse flies of the family Glossinidae, flesh flies of the family Sarcophagidae, flies of the family Hippoboscidae, flies of the family Calliphoridae, and flies of the family Oestridae.

[Endoparasite Control Agent or Endoparasite-Expelling Agent]

An endoparasite control agent or endoparasite-expelling agent according to the present invention contains at least one selected from the arylazole compounds according to the present invention as an active ingredient thereof.

The targeted parasites of the endoparasite control agent or endoparasite-expelling agent according to the present invention are parasitic in host animals (endoparasites), particularly in warm-blooded animals or fish. Examples of the host animals for which the parasite control agent or parasiticide according to the present invention is effective include: warm-blooded animals such as humans, domestic mammals (such as a cow, horse, pig, sheep, and a goat), laboratory animals (such as a mouse, rat, and jird), pets (such as a hamster, guinea pig, dog, cat, horse, squirrel, rabbit, and a ferret), mammals in nature or zoos (such as a monkey, fox, deer, and a buffalo), poultry (such as a turkey, duck, chicken, quail, and a goose), and pet birds (such as a pigeon, parrot, mina, java sparrow, parakeet, Bengalese finch, and a canary); and fish such as salmon, trout, and koi carp. Controlling or expelling the parasites enables to prevent or treat parasitic diseases mediated by parasites.

Examples of the parasite targeted to be controlled or expelled include the followings.

(1) Nematodes of the order Dioctophymatida:
(a) kidney worms of the family Dioctophymatidae, such as *Dioctophyma renale* of *Dioctophyma* spp.; and
(b) kidney worms of the family Soboliphymatidae, such as *Soboliphyme abei* and *Soboliphyme baturini* of *Soboliphyme* spp.

(2) Nematodes of the order Trichocephalida:
(a) trichinae of the family Trichinellidae, such as *Trichinella spiralis* of *Trichinella* spp.; and
(b) whipworms of the family Trichuridae, such as *Capillaria annulata, Capillaria contorta, Capillaria hepatica, Capillaria perforans, Capillaria plica,* and *Capillaria suis,* of *Capillaria* spp.; and *Trichuris vulpis, Trichuris discolor, Trichuris ovis, Trichuris skrjabini,* and *Trichuris suis,* of *Trichuris* spp.

(3) Nematodes of the order Rhabditida:
*Strongyloides stercoralis* of the family Strongyloididae, such as *Strongyloides papillosus, Strongyloides planiceps, Strongyloides ransomi, Strongyloides suis, Strongyloides stercoralis, Strongyloides tumefaciens,* and *Strongyloides ratti,* of *Strongyloides* spp.

(4) Nematodes of the order Strongylida:
ucinarias of the family Ancylostomatidae, such as *Ancylostoma braziliense, Ancylostoma caninum, Ancylostoma duodenale,* and *Ancylostoma tubaeforme,* of *Ancylostoma* spp.; *Uncinaria stenocephala* of *Uncinaria stenocephala*; and *Bunostomum phlebotomum,* and *Bunostomum trigonocephalum,* of *Bunostomum* spp.

(5) Nematodes of the Strongylida Order:
(a) nematodes of the family Angiostrongylidae, such as *Aelurostrongylus abstrusus* of *Aelurostrongylus* spp.; and *Angiostrongylus vasorum,* and *Angiostrongylus cantonesis,* of *Angiostrongylus* spp.;
(b) nematodes of the family Crenosomatidae, such as *Crenosoma aerophila,* and *Crenosoma vulpis,* of *Crenosoma* spp.;

(c) nematodes of the family Filaroididae, such as *Filaroides hirthi,* and *Filaroides osleri,* of *Filaroides* spp.;
(d) metastrongyles of the family Metastrongylidae, such as *Metastrongylus apri, Metastrongylus asymmetricus, Metastrongylus pudendotectus,* and *Metastrongylus salmi,* of *Metastrongylus* spp.; and
(e) gapeworms of the family Syngamidae, such as *Cyathostoma bronchialis* of *Cyathostoma* spp.; and *Syngamus skrjabinomorpha,* and *Syngamus trachea,* of *Syngamus* spp.

(6) Nematodes of the order Strongylida:
(a) nematodes of the family Molineidae, such as *Nematodirus filicollis,* and *Nematodirus spathiger,* of *Nematodirus* spp.;
(b) nematodes of the family Dictyocaulidae, such as *Dictyocaulus filaria,* and *Dictyocaulus viviparus,* of *Dictyocaulus* spp.;
(c) nematodes of the family Haemonchidae, such as *Haemonchus contortus* of *Haemonchus* spp.; and *Mecistocirrus digitatus* of *Mecistocirrus* spp.;
(d) nematodes of the family Haemonchidae, such as *Ostertagia ostertagi* of *Ostertagia* spp.;
(e) nematodes of the family Heligmonellidae, such as *Nippostrongylus braziliensis* of *Nippostrongylus* spp.; and
(f) nematodes of the family Trichostrongylidae, such as *Trichostrongylus axei, Trichostrongylus colubriformis,* and *Trichostrongylus tenuis,* of *Trichostrongylus* spp.; *Hyostrongylus rubidus* of *Hyostrongylus* spp.; and *Obeliscoides cuniculi* of *Obeliscoides* spp.

(7) Nematodes of the order Strongylida:
(a) nematodes of the family Chabertiidae, such as *Chabertia ovina* of *Chabertia* spp.; and *Oesophagostomum brevicaudatum, Oesophagostomum columbianum, Oesophagostomum dentatum, Oesophagostomum georgianum, Oesophagostomum maplestonei, Oesophagostomum quadri spinulatum, Oesophagostomum radiatum, Oesophagostomum venulosum,* and *Oesophagostomum watanabei,* of *Oesophagostomum* spp.;
(b) nematodes of the family Stephanuridae, such as *Stephanurus dentatus* of *Stephanurus* spp.; and
(c) nematodes of the family Strongylidae, such as *Strongylus asini, Strongylus edentatus, Strongylus equinus,* and *Strongylus vulgaris,* of *Strongylus* spp.

(8) Nematodes of the order Oxyurida:
nematodes of the family Oxyuridae, such as *Enterobius anthropopitheci,* and *Enterobius vermicularis,* of *Enterobius* spp.; *Oxyuris equi* of *Oxyuris* spp.; and *Passalurus ambiguus* of *Passalurus* spp.

(9) Nematodes of the order Ascaridida:
(a) nematodes of the Ascaridiidae, such as *Ascaridia galli* of *Ascaridia* spp.;
(b) nematodes of the family Heterakidae, such as *Heterakis beramporia, Heterakis brevispiculum, Heterakis gallinarum, Heterakis pusilla,* and *Heterakis putaustralis,* of *Heterakis* spp.;
(c) nematodes of the family Anisakidae, such as *Anisakis simplex* of *Anisakis* spp.;
(d) nematodes of the family Ascarididae, such as *Ascaris lumbricoides,* and *Ascaris suum,* of *Ascaris* spp.; and *Parascaris equorum* of *Parascaris* spp.; and
(e) nematodes of the family Toxocaridae, such as *Toxocara canis, Toxocara leonina, Toxocarasuum, Toxocara vitulorum,* and *Toxocara cati,* of *Toxocara* spp.

(10) Nematodes of the Spirurida Order
(a) nematodes of the family Onchocercidae, such as *Brugia malayi, Brugia pahangi*, and *Brugia patei*, of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis, Onchocerca gibsoni*, and *Onchocerca gutturosa*, of *Onchocerca* spp.;
(b) nematodes of the family Setariidae, such as *Setaria digitata, Setaria equina, Setaria labiatopapillosa*, and *Setaria marshalli*, of *Setaria* spp.; and *Wuchereria bancrofti* of *Wuchereria* spp.; and
(c) nematodes of the family Filariidae, such as *Parafilaria multipapillosa* of *Parafilaria* spp.; and *Stephanofilaria assamensis, Stephanofilaria dedoesi, Stephanofilaria kaeli, Stephanofilaria okinawaensis*, and *Stephanofilaria stilesi* of *Stephanofilaria* spp.

(11) Nematodes of the order Spirurida:
(a) nematodes of the family Gnathostomatidae, such as *Gnathostoma doloresi*, and *Gnathostoma spinigerum*, of *Gnathostoma* spp.;
(b) nematodes of the family Habronematidae, such as *Habronema majus, Habronema microstoma*, and *Habronema muscae*, of *Habronema* spp.; and *Draschia megastoma* of *Draschia* spp.;
(c) nematodes of the family Physalopteridae, such as *Physaloptera canis, Physaloptera cesticillata, Physaloptera erdocyona, Physaloptera felidis, Physaloptera gemina, Physaloptera papilloradiata, Physaloptera praeputialis, Physaloptera pseudopraerutialis, Physaloptera rara, Physaloptera sibirica*, and *Physaloptera vulpineus*, of *Physaloptera* spp.;
(d) nematodes of the family Gongylonematidae, such as *Gongylonema pulchrum* of *Gongylonema* spp.;
(e) nematodes of the family Spirocercidae, such as *Ascarops strongylina* of *Ascarops* spp.; and
nematodes of the family Thelaziidae, such as *Thelazia callipaeda, Thelazia gulosa, Thelazia lacrymalis, Thelazia rhodesi*, and *Thelazia skrjabini*, of *Thelazia* spp.

[Other Pest Control Agents]

Furthermore, control effects against pests having a stinger or venom that harms humans and animal, pests which mediate various pathogens or disease-causing microbes, or pests which cause discomfort to humans (such as toxic pests, hygienic pests, and obnoxious pests) are excellent.

Specific examples thereof are as shown below.

(1) Pests of the order Hymenoptera bees of the family Argidae, bees of the family Cynipidae, bees of the family Diprionidae, ants of the family Formicidae, bees of the family Mutillidae, and bees of the family Vespidae.

(2) Other pests

Cockroaches (Blattodea), termites (termite), spiders (Araneae), centipedes (cetipede), millipedes (millipede), crustaceans (crustacea), bedbugs (*Cimex lectularius*).

[Agent Formulation]

A few examples of agent formulation for the pest control agent, the insecticide, the acaricide, the ectoparasite control agent, endoparasite control agent or expelling agent according to the present invention are provided below. However, added components and the addition ratio are not intended to be limited to these examples, and can be suitably modified in a wide variation. The term "part" in the agent formulations indicates part by weight.

Agent formulations for horticulture and wetland farming are as shown below.

(Agent Formulation 1: Wettable Powder)

40 parts of the arylazole compound of the present invention, 53 parts of diatomaceous earth, 4 parts of higher alcohol sulfuric acid ester and 3 parts of alkylnaphthalenesulfonate are homogeneously mixed and finely pulverized to obtain a wettable powder with an active ingredient of 40%.

(Agent Formulation 2: Emulsion)

30 parts of the arylazole compound of the present invention, 33 parts of xylene, 30 parts of dimethylformamide, and 7 parts of polyoxyethylene alkyl allyl ether are mixed and dissolved to obtain an emulsion with an active ingredient of 30%.

(Agent Formulation 3: Granular Agent)

5 parts of the arylazole compound according to the present invention, 40 parts of talc, 38 parts of clay, 10 parts of bentonite, and 7 parts of alkyl sodium sulfate are uniformly mixed, finely ground, and then granulated into granules having a diameter of 0.5 to 1.0 mm, to obtain a granular agent with an active ingredient of 5%.

(Agent Formulation 4: Granular Agent)

5 parts of the arylazole compound according to the present invention, 73 parts of clay, 20 parts of bentonite, 1 part of dioctyl sulfosuccinate sodium salt, and 1 part of potassium phosphate are well ground and mixed, and then water is added thereto, and the mixture is kneaded thoroughly, followed by granulation and drying the resultant to obtain a granular agent with an active ingredient of 5%.

(Agent Formulation 5: Suspension Agent)

10 parts of the arylazole compound according to the present invention, 4 parts of polyoxyethylene alkylaryl ether, 2 parts of sodium polycarboxylate, 10 parts of glycerin, 0.2 parts of xanthan gum, and 73.8 parts of water are mixed, and then the mixture is wet-ground until the grain size reaches 3 µm or less to obtain a suspension agent with an active ingredient of 10%.

Agent formulations for the ectoparasite control agent, the endoparasite control agent or the endoparasite-expelling agent are as shown below.

(Agent Formulation 6: Granular Agent)

5 parts of the arylazole compound according to the present invention are dissolved in an organic solvent to obtain a solution, and the solution is sprayed onto 94 parts of kaolin and 1 part of white carbon, and then the solvent is evaporated under reduced pressure. The thus obtained granular agent may be mixed with animal feed.

(Agent Formulation 7: Injection Agent)

0.1 to 1 part of the arylazole compound according to the present invention and 99 to 99.9 parts of peanut oil are homogeneously mixed, and then the mixture is sterilized by filtration using a sterilizing filter.

(Agent Formulation 8: Pour-on Agent)

5 parts of the arylazole compound according to the present invention, 10 parts of myristic acid ester, and 85 parts of isopropanol are homogenously mixed to obtain a pour-on agent.

(Agent Formulation 9 Spot-on Agent)

10 to 15 parts of the arylazole compound according to the present invention, 10 parts of palmitic acid ester, and 75 to 80 parts of isopropanol are homogenously mixed to obtain a spot-on agent.

(Agent Formulation 10: Spray Agent)

1 part of the arylazole compound according to the present invention, 10 parts of propylene glycol, and 89 parts of isopropanol are homogenously mixed to obtain a spray agent.

Next, the present invention will be described in more detail with reference to Examples. However, the present invention is in no way limited by the following Examples.

Additions, omissions, substitutions, and other changes in the configuration are possible without departing from the spirit of the present invention.

Example 1

Synthesis of 5-(2-Chloro-3,3,3-trifluoroprop-1-en-1-yl)-2-(2-(ethylsulfonyl)-4-(trifluoromethyl)phenyl)-1-methyl-1H-imidazole (Compound No. 1-1)

Step 1-1

Synthesis of 2-(2-fluoro-4-(trifluoromethyl)phenyl)-1H-imidazole

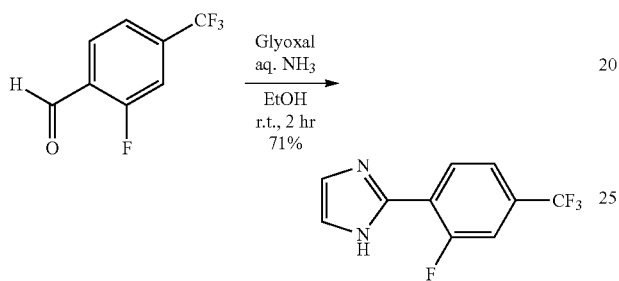

2-Fluoro-4-(trifluoromethyl)benzaldehyde (15 g) was dissolved in ethanol (200 ml) and the solution was cooled to 0° C. 28% aqueous ammonia (95 g) and glyoxal (57 g) were added thereto and the mixture was stirred at room temperature for 2 hours. The reaction solution was concentrated under reduced pressure, and water was added to the obtained residue. Then, the mixture was extracted with 20% methanol/dichloromethane, and the obtained organic layer was dried over anhydrous magnesium sulfate and filtered. The filtrate was concentrated under reduced pressure, and the obtained residue was purified by silica gel column chromatography to obtain 13 g (yield 71%) of the objective compound.

$^1$H-NMR of the obtained target product is shown below.
$^1$H-NMR (400 MHz, CDCl$_3$): δ 9.90 (br s, 1H), 8.44 (t, 1H), 7.54 (d, 1H), 7.45 (d, 1H), 7.29 (s, 1H), 7.22 (s, 1H).

Step 1-2

Synthesis of 2-(2-fluoro-4-(trifluoromethyl)phenyl)-1-methyl-1H-imidazole

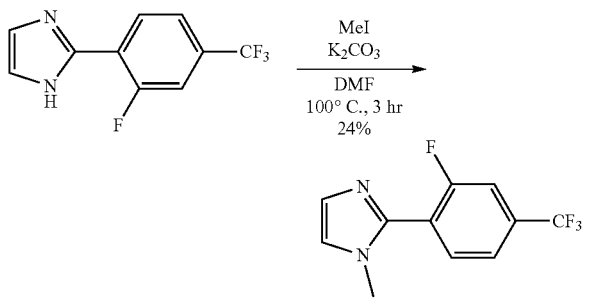

2-(2-Fluoro-4-(trifluoromethyl)phenyl)-1H-imidazole (13 g) was dissolved in N,N-dimethylformamide (250 ml), and the solution was stirred at room temperature. Potassium carbonate (15 g) and methyl iodide (8.6 g) were added thereto, and after purging with nitrogen gas, the mixture was stirred at 100° C. for 3 hours. After the reaction solution was cooled to room temperature, the reaction solution was poured into water and then extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 3.2 g (yield 24%) of the objective compound.

$^1$H-NMR of the obtained target product is shown below.
$^1$H-NMR (400 MHz, CDCl$_3$): δ 7.76 (t, 1H), 7.54 (d, 1H), 7.45 (d, 1H), 7.20 (s, 1H), 7.06 (s, 1H), 3.65 (d, 3H).

Step 1-3

Synthesis of 2-(2-(ethylthio)-4-(trifluoromethyl)phenyl)-1-methyl-1H-imidazole

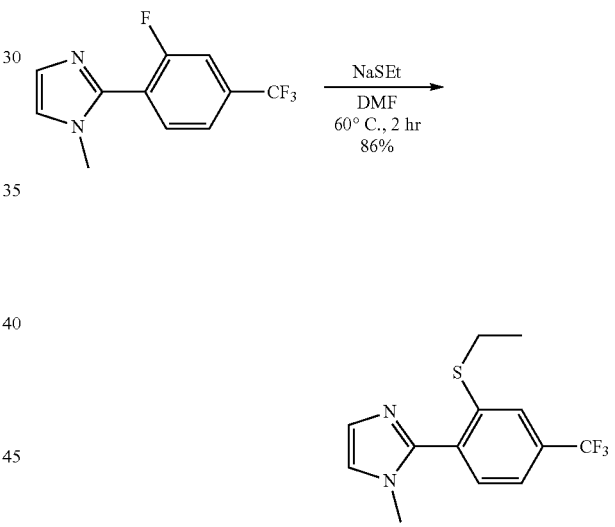

2-(2-Fluoro-4-(trifluoromethyl)phenyl)-1-methyl-1H-imidazole (3.2 g) was dissolved in N,N-dimethylformamide (130 ml) and the solution was stirred at room temperature. Sodium ethyl mercaptan (80%, 2.8 g) was added thereto, and the mixture was stirred at 60° C. for 2 hours. After the reaction solution was cooled to room temperature, the reaction solution was poured into water and then extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 3.2 g (yield 86%) of the objective compound.

$^1$H-NMR of the obtained target product is shown below.
$^1$H-NMR (400 MHz, CDCl$_3$): δ 7.58 (s, 1H), 7.50-7.45 (m, 2H), 7.18 (s, 1H), 7.02 (s, 1H), 3.53 (s, 3H), 2.88 (q 3H), 1.28 (t, 3H).

Step 1-4

Synthesis of 2-(2-(ethylsulfonyl)-4-(trifluoromethyl)phenyl)-1-methyl-1H-imidazole

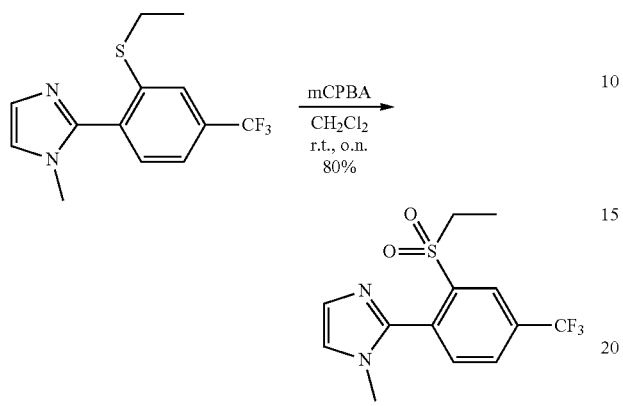

2-(2-(Ethylthio)-4-(trifluoromethyl)phenyl)-1-methyl-1H-imidazole (3.2 g) was dissolved in dichloromethane (110 ml) and the solution was stirred at 0° C. Methachloroperbenzoic acid (70%, 6.1 g) was added thereto, and the mixture was stirred at room temperature overnight. The reaction solution was poured into a mixed solution of saturated sodium hydrogen carbonate aqueous solution and saturated sodium thiosulfate aqueous solution and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 2.8 g (yield 80%) of the objective product.

$^1$H-NMR of the obtained target product is shown below.
$^1$H-NMR (400 MHz, CDCl$_3$): δ 8.44 (d, 1H), 7.99 (dd, 1H), 7.65 (d, 1H), 7.16 (d, 1H), 7.06 (d, 1H), 3.48 (s, 3H), 3.42 (q 3H), 1.24 (t, 3H).

Step 1-5

Synthesis of 5-bromo-2-(2-(ethylsulfonyl)-4-(trifluoromethyl)phenyl)-1-methyl-1H-imidazole

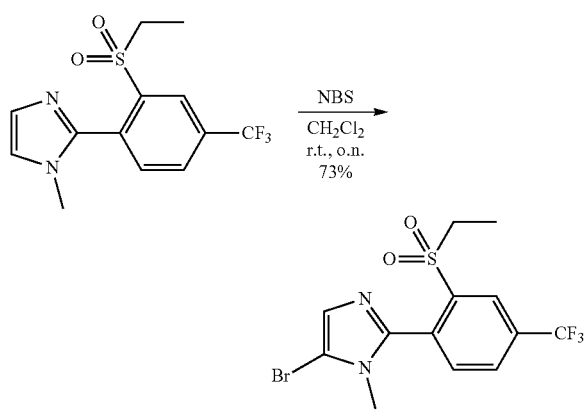

2-(2-(Ethylsulfonyl)-4-(trifluoromethyl)phenyl)-1-methyl-1H-imidazole (0.25 g) was dissolved in dichloromethane (8 ml) and stirred at 0° C. N-bromosuccinimide (0.14 g) was added into the solution, and the solution was further stirred at room temperature overnight. The reaction solution was poured into a saturated aqueous sodium hydrogen carbonate solution and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.23 g (yield: 73%) of the objective compound.

$^1$H-NMR of the obtained target product is shown below.
$^1$H-NMR (400 MHz, CDCl$_3$): δ 8.44 (d, 1H), 8.02 (dd, 1H), 7.63 (d, 1H), 7.14 (s, 1H), 3.42 (q, 2H), 3.41 (s, 3H), 1.24 (t, 3H).

Step 1-6

Synthesis of ethyl 2-(2-(ethyl sulfonyl)-4-(trifluoromethyl)phenyl-1-methyl-1H-imidazole-5-carboxylate

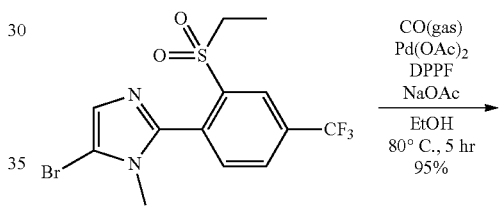

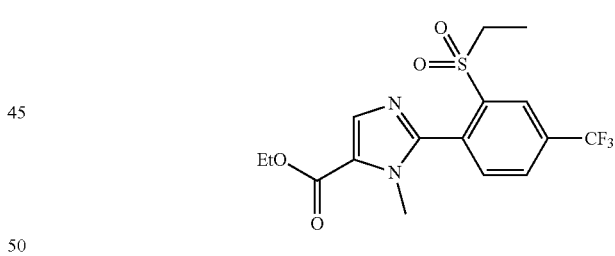

5-Bromo-2-(2-(ethylsulfonyl)-4-(trifluoromethyl)phenyl)-1-methyl-1H-imidazole (0.55 g), palladium acetate (3.1 mg), 1,1'-bis(diphenyl phosphino)ferrocene (16 mg), sodium acetate (0.13 g) and ethanol (6 ml) were added to a metal autoclave reaction vessel, and the reaction atmosphere was replaced with carbon monoxide (0.8 MPa), followed by stirring at 80° C. for 5 hours. The reaction solution was cooled to room temperature, filtered, and the filtrate was concentrated under reduced pressure. The resulting residue was purified by silica gel column chromatography to obtain 0.52 g (yield 95%) of the objective compound.

$^1$H-NMR of the obtained target product is shown below.
$^1$H-NMR (400 MHz, CDCl$_3$): δ 8.44 (d, 1H), 8.02 (dd, 1H), 7.81 (s, 3H), 7.63 (d, 1H), 4.36 (q, 2H), 3.69 (s, 3H), 3.44 (q, 2H), 1.40 (t, 3H), 1.26 (t, 3H).

Step 1-7

Synthesis of (2-(2-(ethylsulfonyl)-4-(trifluoromethyl)phenyl)-1-methyl-1H-imidazol-5-yl)methanol

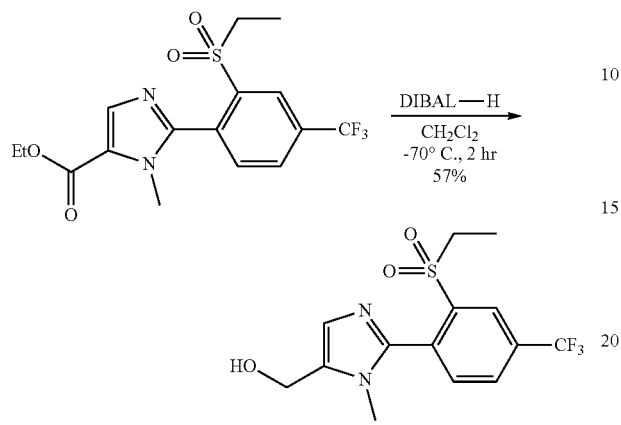

Ethyl 2-(2-(ethylsulfonyl)-4-(trifluoromethyl)phenyl)-1-methyl-1H-imidazole-5-carboxylate (0.98 g) was dissolved in dichloromethane (8 ml) and stirred at −70° C. Diisobutylaluminum hydride (13 ml, 1.0 M solution in n-hexane) was added dropwise into the solution, and the mixture was stirred at −70° C. for 2 hours. The reaction solution was poured into a 10% Rochelle salt aqueous solution, and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.50 g (yield 57%) of the objective compound.

$^1$H-NMR of the obtained target product is shown below.

$^1$H-NMR (400 MHz, CDCl$_3$): δ 8.43 (d, 1H), 8.00 (dd, 1H), 7.65 (d, 1H), 7.10 (s, 1H), 4.72 (d, 2H), 3.48 (s, 3H), 3.45 (q, 2H), 1.67 (t, 1H), 1.24 (t, 3H).

Step 1-8

Synthesis of 2-(2-(ethylsulfonyl)-4-(trifluoromethyl)phenyl)-1-methyl-1H-imidazole-5-carbaldehyde

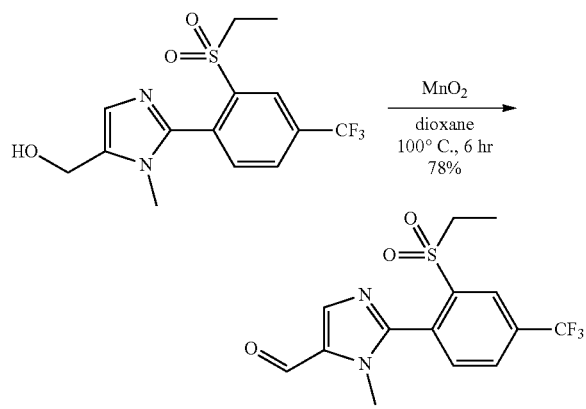

(2-(2-(Ethylsulfonyl)-4-(trifluoromethyl)phenyl)-1methyl-1H-imidazol-5-yl) methanol (0.50 g) was dissolved in 1,4-dioxane (5 ml) and the solution was stirred at room temperature. Manganese dioxide (1.2 g) was added thereto, and the mixture was stirred at 100° C. for 6 hours. The reaction solution was cooled to room temperature, filtered, and the filtrate was concentrated under reduced pressure. The obtained residue was purified by silica gel column chromatography to obtain 0.38 g (yield 78%) of the objective compound.

$^1$H-NMR of the obtained target product is shown below.

$^1$H-NMR (400 MHz, CDCl$_3$): δ 9.85 (s, 1H), 8.46 (s, 1H), 8.05 (d, 1H), 7.86 (s, 1H), 7.65 (d, 1H), 3.73 (s, 3H), 3.45 (q, 2H), 1.28 (t, 3H).

Step 1-9

Synthesis of 5-(2-chloro-3,3,3-trifluoroprop-1-en-1-yl)-2-(2-(ethyl sulfonyl)-4-(trifluoromethyl)phenyl)-1-methyl-1H-imidazole

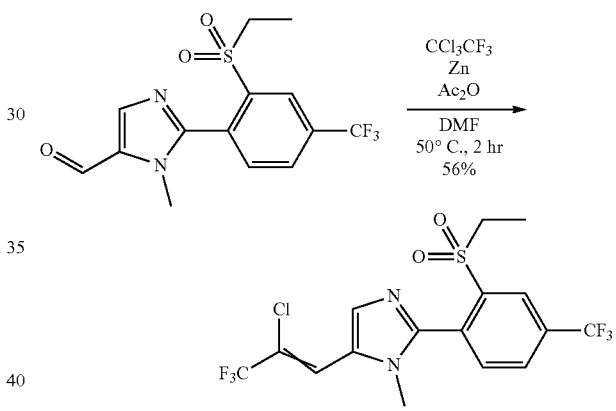

2-(2-(Ethylsulfonyl)-4-(trifluoromethyl)phenyl)-1-methyl-1H-imidazole-5-carbaldehyde (0.31 g) was dissolved in N,N-dimethylformamide (0.9 ml) and the mixture was stirred at room temperature. 1,1,1-trichloro-2,2,2-trifluoroethane (0.34 g), zinc powder (0.29 g) and acetic anhydride (0.14 g) were added thereto, and the inside of the reaction vessel was purged with argon, and the mixture was stirred at 50° C. for 2 hours. The reaction solution was poured into a saturated aqueous sodium hydrogen carbonate solution, and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.23 g of the objective product (E/Z=15:85, yield 56%).

$^1$H-NMR and $^{19}$F-NMR of the obtained target product are shown below.

$^1$H-NMR (400 MHz, CDCl$_3$) (an E/Z mixture): δ 8.45 (m, 1H), 8.06-7.44 (m, 3H), 7.14-6.92 (m, 1H), 3.45 (s, 3H) 3.42-3.44 (m, 2H), 1.28-1.24 (m, 3H).

$^{19}$F-NMR (376 MHz, CDCl$_3$—CFCl$_3$): δ −63.5 (s, 3F), −63.6 (s) for the (E)-isomer and −68.5 (s) for the (Z)-isomer.

Example 2

Synthesis of (E)-5-(2-(ethyl sulfonyl)-4-(trifluoromethyl)phenyl)-1-methyl-2-(3,3,3-trifluoroprop-1-en-1-yl)-1H-imidazole (Compound No. 2-1)

Step 2-1

Synthesis of 5-(2-fluoro-4-(trifluoromethyl)phenyl)-1-methyl-1H-imidazole

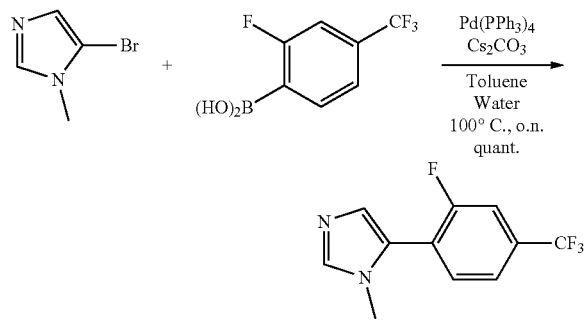

5-Bromo-1-methyl-1H-imidazole (5.0 g) was dissolved in toluene (50 ml) and stirred at room temperature. Water (5 ml), 2-fluoro-4-(trifluoromethyl) phenylboronic acid (9.6 g), tetrakis(triphenylphosphine)palladium(0) (1.8 g), and cesium carbonate (10 g) were added into the solution, the reaction vessel was purged with nitrogen, and the solution was stirred at 100° C. overnight. The reaction solution was poured into water and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 8.7 g (yield quant.) of the objective product.

$^1$H-NMR of the obtained target product is shown below.
$^1$H-NMR (400 MHz, CDCl$_3$): δ 7.60 (s, 1H), 7.52-7.45 (m, 3H), 7.18 (s, 1H), 3.64 (d, 3H).

Step 2-2

Synthesis of 5-(2-(ethylthio)-4-(trifluoromethyl)phenyl)-1-methyl-1H-imidazole

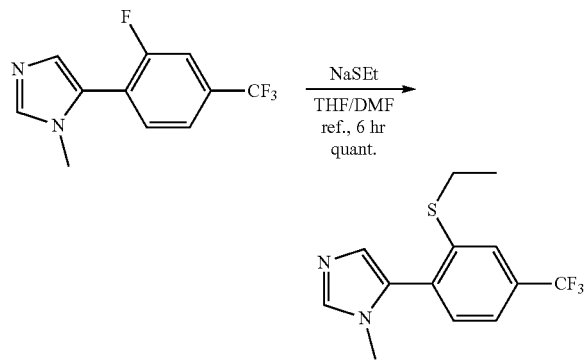

5-(2-Fluoro-4-(trifluoromethyl)phenyl)-1-methyl-1H-imidazole (7.7 g) was dissolved in a mixed solvent of tetrahydrofuran (90 ml) and N, N-dimethylformamide (20 ml) and the mixed solution was stirred at room temperature. Sodium ethyl mercaptan (80%, 9.8 g) was added thereto, and the mixture was stirred and heated under reflux for 6 hours. After the reaction solution was cooled to room temperature and poured into water, the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 8.6 g (yield quant.) of the objective product.

$^1$H-NMR of the obtained target product is shown below.
$^1$H-NMR (400 MHz, CDCl$_3$): δ 8.02 (s, 1H), 7.57 (s, 1H), 7.52 (s, 1H), 7.44 (d, 1H), 7.33 (d, 1H), 7.07 (d, 1H), 3.46 (s, 3H), 2.91 (q, 2H), 1.31 (t, 3H).

Step 2-3

Synthesis of 5-(2-(ethylthio)-4-(trifluoromethyl)phenyl)-1-methyl-1H-imidazole-2-carbaldehyde

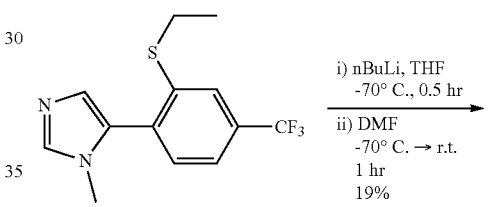

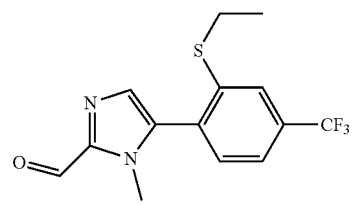

5-(2-(Ethylthio)-4-(trifluoromethyl)phenyl)-1-methyl-1H-imidazole (0.63 g) was dissolved in anhydrous tetrahydrofuran (15 ml) and stirred at −70° C. n-Butyllithium (1.4 ml, 1.6 M normal hexane solution) was added dropwise into solution, and the solution was stirred at −70° C. for 0.5 hours. Next, N,N-dimethylformamide (0.32 g) was added dropwise and the mixture was heated to room temperature and stirred for 1 hour. The reaction solution was poured into water and then the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.13 g (yield 19%) of the objective compound.

$^1$H-NMR of the obtained target product is shown below.
$^1$H-NMR (400 MHz, CDCl$_3$): δ 9.89 (s, 1H), 7.56 (s, 1H), 7.49 (d, 1H), 7.34 (d, 1H), 7.31 (s, 1H), 3.79 (s, 3H), 2.95 (q, 2H), 1.32 (t, 3H).

Step 2-4

Synthesis of (E)-5-(2-(ethylthio)-4-(trifluoromethyl)phenyl)-1-methyl-2-(3,3,3-trifluoroprop-1-en-1-yl)-imidazole

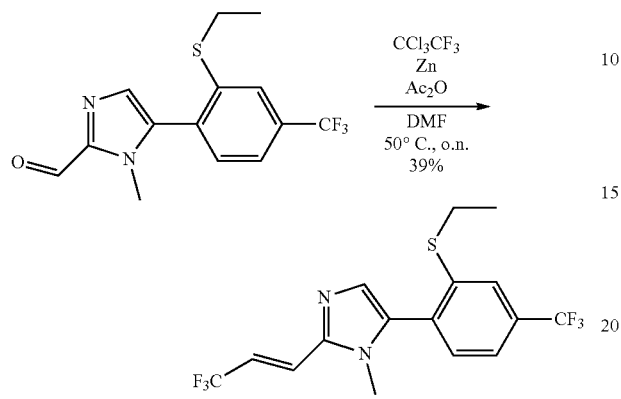

5-(2-(Ethylthio)-4-(trifluoromethyl)phenyl)-1-methyl-1H-imidazole-2-carbaldehyde (0.13 g) was dissolved in N,N-dimethylformamide (0.5 ml) and the mixture was stirred at room temperature. 1,1,1-Trichloro-2,2,2-trifluoroethane (0.15 g), zinc powder (0.13 g) and acetic anhydride (0.063 g) were added thereto, and the inside of the reaction vessel was purged with argon and stirred at 50° C. overnight. The reaction solution was poured into a saturated aqueous sodium hydrogen carbonate solution and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.061 g (yield 39%) of the objective compound.

$^1$H-NMR of the obtained target product is shown below.
$^1$H NMR (400 MHz, CDCl$_3$): δ 7.54 (s, 1H), 7.47 (d, 1H), 7.33 (d, 1H), 7.16 (s, 1H), 7.05 (dq, 1H), 6.76 (dq, 1H), 3.50 (s, 3H), 2.92 (q, 2H), 1.31 (t, 3H).

Step 2-5

Synthesis of (E)-5-(2-(ethylsulfonyl)-4-(trifluoromethyl)phenyl)-1-methyl-2-(3,3,3-trifluoroprop-1-en-1-yl)-1H-imidazole

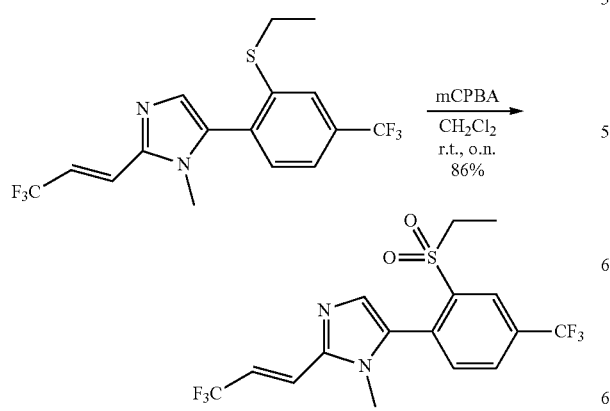

(E)-5-(2-(Ethylthio)-4-(trifluoromethyl)phenyl)-1-methyl-2-(3,3,3-trifluoroprop-1-en-1-yl)-1H-imidazole (0.061 g) was dissolved in dichloromethane (2 ml) and the solution was stirred at 0° C. Methachloroperbenzoic acid (70%, 0.087 g) was added thereto, and the mixture was stirred at room temperature overnight. The reaction solution was poured into a mixed solution of saturated sodium hydrogen carbonate aqueous solution and saturated sodium thiosulfate aqueous solution, and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.057 g (yield 86%) of the objective compound.

$^1$H-NMR of the obtained target product is shown below.
$^1$H-NMR (400 MHz, CDCl$_3$): δ 8.49 (d, 1H), 8.00 (dd, 1H), 7.58 (d, 1H), 7.14 (s, 3H), 7.04 (dq, 1H), 6.78 (dq, 1H), 3.46 (s, 3H), 3.02 (q, 2H), 1.20 (t, 3H).

Example 3

Synthesis of (Z)-5-(2-chloro-3,3,4,4,4-pentafluorobut-1-en-1-yl)-2-(2-(ethyl sulfonyl)-4-(trifluoromethyl)phenyl)-1-methyl-1H-imidazole (Compound No. 1-64)

Step 3-1

Synthesis of 2-(2-(ethylthio)-4-(trifluoromethyl)phenyl)-5-(2-iodovinyl)-1-methyl-1H-imidazole

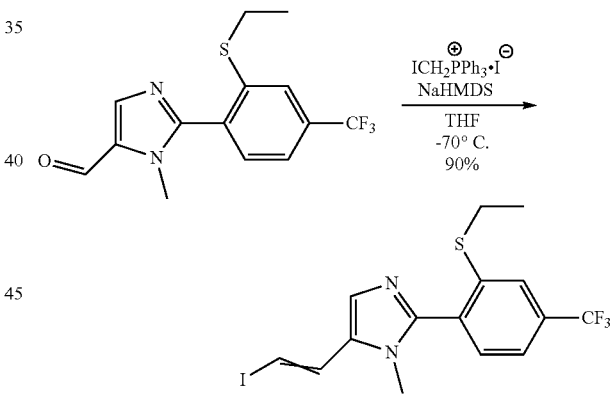

(Iodomethyl) triphenylphosphonium iodide (5.0 g) was dissolved in tetrahydrofuran (60 ml), and sodium bis(trimethylsilyl)amide (5.0 ml, 1.9 M tetrahydrofuran solution) was added dropwise thereto at room temperature and the mixture was stirred at room temperature for 2 hours. The reaction solution was cooled to −70° C. and a tetrahydrofuran solution (20 ml) of 2-(2-(ethylthio)-4-(trifluoromethyl)phenyl)-1-methyl-1H-imidazole-5-carbaldehyde (2.1 g) was added dropwise thereto, and the mixture was stirred at −70° C. for 1 hour and 30 minutes. The reaction solution was poured into water and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 2.6 g of the desired product (E/Z mixture, yield 90%).

¹-NMR of the obtained target product is shown below.
¹H-NMR (400 MHz, CDCl₃): δ 8.23 (s, 1H, Z isomer), 7.59-7.26 (m, 4H of Z isomer, 5H of E isomer), 6.76 (d, 1H, E isomer), 6.66 (d, 1H, Z isomer), 3.52 (d, 3H, E isomer), 3.44 (d, 1H, Z isomer), 2.93-2.86 (q, 2H), 1.31-1.24 (t, 3H).

Step 3-2

Synthesis of 2-(2-(ethylsulfonyl)-4-(trifluoromethyl)phenyl)-5-(2-iodovinyl)-1-methyl-1H-imidazole

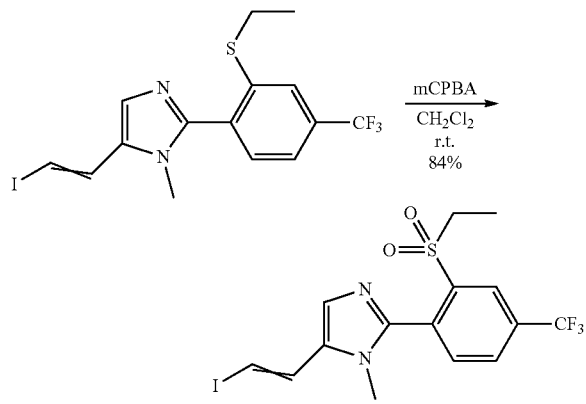

2-(2-(ethylthio)-4-(trifluoromethyl)phenyl)-5-(2-iodovinyl)-1-methyl-1H-imidazole (2.6 g) was dissolved in dichloromethane (40 ml) and stirred at 0° C. Methachloroperbenzoic acid (70%, 3.3 g) was added thereto, and the mixture was stirred at room temperature overnight. The reaction solution was poured into a mixed solution of saturated sodium hydrogen carbonate aqueous solution and saturated sodium thiosulfate aqueous solution and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 2.4 g of the objective product (E/Z mixture, yield 84%).

¹H-NMR of the obtained target product is shown below.
¹H-NMR (400 MHz, CDCl₃): δ 8.44 (m, 1H), 8.19 (s, 1H, Z isomer), 8.00 (m, 1H), 7.66-7.24 (m, 2H of Z isomer, 3H of E isomer), 6.81 (d, 1H, E isomer), 6.72 (d, 1H, Z isomer), 3.47-3.37 (m, 5H), 1.28-1.22 (t, 3H).

Step 3-3

Synthesis of (E)-2-(2-(ethylsulfonyl)-4-(trifluoromethyl)phenyl)-1-methyl-5-(3,3,4,4,4-pentafluorobut-1-en-1-yl)-1H-imidazole

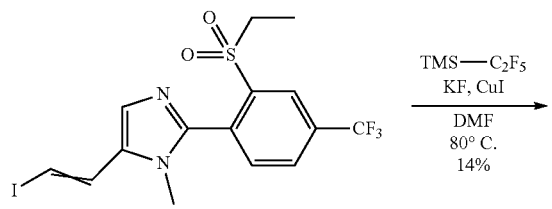

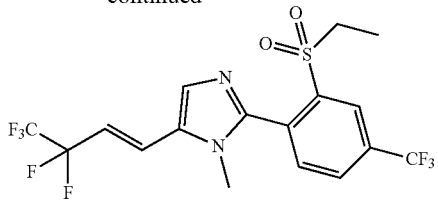

2-(2-(ethylsulfonyl)-4-(trifluoromethyl)phenyl)-5-(2-iodovinyl)-1-methyl-1H-imidazole (2.4 g) was dissolved in N,N-Dimethylformamide (25 ml). (Pentafluoroethyl)trimethylsilane (4.6 g), potassium fluoride (0.35 g), and copper (I) iodide (1.4 g) were added thereto, and the mixture was stirred at 80° C. overnight. The reaction solution was poured into dilute aqueous ammonia and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.32 g (yield 14%) of the objective compound.

¹H-NMR of the obtained target product is shown below.
¹H-NMR (400 MHz, CDCl₃): δ 8.43 (d, 1H), 8.00 (dd, 1H), 7.65 (d, 1H), 7.58 (s, 1H), 6.77 (dt, 1H), 5.73 (dd, 1H), 3.43 (d, 3H), 3.34 (q, 2H), 1.25 (t, 3H).

Step 3-4

Synthesis of (Z)-5-(2-chloro-3,3,4,4,4-pentafluorobut-1-en-1-yl)-2-(2-(ethyl sulfonyl)-4-(trifluoromethyl)phenyl)-1-methyl-1H-imidazole

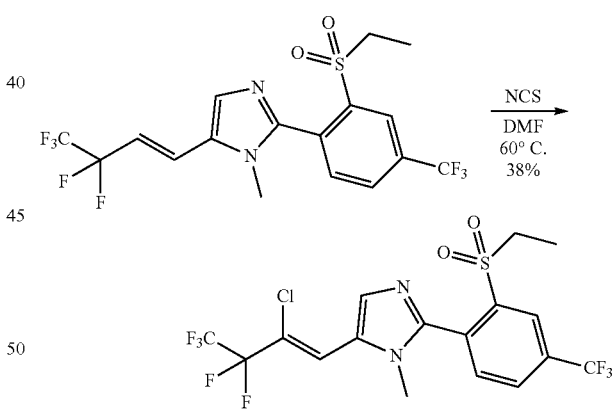

(E)-2-(2-(ethylsulfonyl)-4-(trifluoromethyl)phenyl)-5-(3,3,4,4,4-pentafluorobut-1-en-1-yl)-1-methyl-1H-imidazole (0.32 g) was dissolved in N,N-dimethylformamide (10 ml), and N-chlorosuccinimide (0.092 g) was added thereto, and the mixture was stirred at 60° C. overnight. The reaction solution was poured into a saturated aqueous sodium hydrogencarbonate solution, and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.13 g (yield 38%) of the objective compound.

¹H-NMR of the obtained target product is shown below.
¹H-NMR (400 MHz, CDCl₃): δ 8.45 (s, 1H), 8.09 (s, 1H), 8.03 (d, 1H), 7.63 (s, 1H), 7.11 (s, 1H), 3.45 (s, 3H), 3.41 (q, 2H), 1.26 (t, 3H).

Example 4

Synthesis of (Z)-4-(2-chloro-3,3,3-trifluoroprop-1-en-1-yl)-1-(2-(ethylsulfonyl)-4-(trifluoromethyl)phenyl)-5-methyl-1H-1,2,3-triazole (Compound No. 11-3)

Step 4-1

Synthesis of 1-azido-2-fluoro-4-(trifluoromethyl)benzene

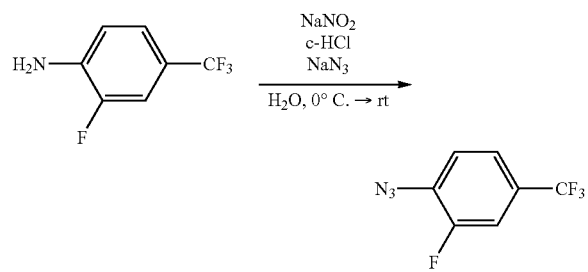

Water (2 ml) and hydrochloric acid (2 ml) were added to 2-fluoro-4-(trifluoromethyl) aniline (1.15 g), and the mixture was stirred at 0° C. Sodium nitrite (0.54 g) dissolved in water (2 ml) was added thereto, and the mixture was stirred at 0° C. for 10 minutes, then sodium azide (0.31 g) dissolved in water (2 ml) was added, and the mixture was stirred at room temperature for 30 minutes. The reaction solution was poured into water and then the organic phase was extracted with ethyl acetate. The obtained organic layer was washed with saturated brine, dried over anhydrous magnesium sulfate, and filtered. The filtrate was concentrated under reduced pressure, and the obtained residue was used in the next step without purification.

Step 4-2

Synthesis of Ethyl 1-(2-fluoro-4-(trifluoromethyl)phenyl)-5-methyl-1H-1,2,3-triazole-4-carboxylate

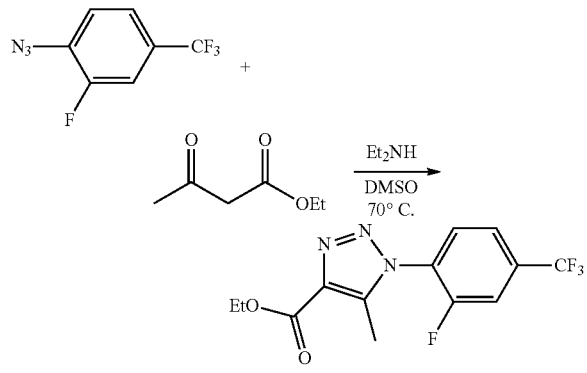

1-Azido-2-fluoro-4-(trifluoromethyl)benzene obtained in Step 4-1 was dissolved in dimethylsulfoxide (10 ml) and stirred at room temperature. Ethyl acetoacetate (1.8 ml) and diethylamine (3.4 ml) were added thereto, followed by stirring at 70° C. overnight. The reaction solution was poured into water and then the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.55 g (yield 27%) of the objective compound.
¹H-NMR of the obtained target product is shown below.
¹H-NMR (400 MHz, CDCl₃): δ 7.73-7.63 (m, 3H), 4.48 (q, 2H), 2.55 (d, 3H), 1.46 (t, 3H).

Step 4-3

Synthesis of Ethyl 1-(2-(ethylthio)-4(ethylthio)-4-(trifluoromethyl)phenyl)-5-methyl-1H-1,2,3-triazole-4-carboxylate

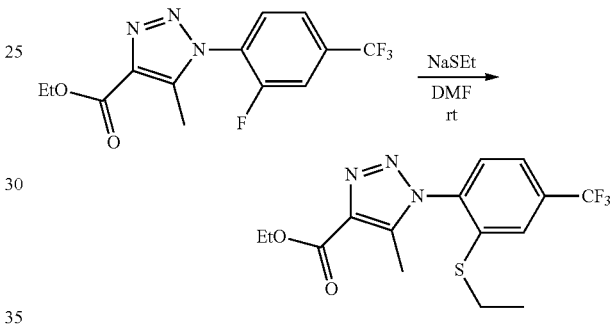

Ethyl 1-(2-fluoro-4-(trifluoromethyl)phenyl)-5-methyl-1H-1,2,3-triazole-4-carboxylate (0.55 g) was dissolved in N,N-dimethylformamide (6 ml) and stirred at room temperature. Ethyl mercaptan sodium (80%, 0.27 g) was added thereto, and the mixture was stirred at room temperature for 3 hours. The reaction solution was poured into water and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.41 g (yield 65%) of the objective compound.
¹H-NMR of the obtained target product is shown below.
¹H-NMR (400 MHz, CDCl₃): δ 7.66 (s, 1H), 7.61 (d, 1H), 7.43 (d, 1H), 4.48 (q, 2H), 2.91 (q, 2H), 2.46 (s, 3H), 1.47 (t, 3H), 1.28 (t, 3H).

Step 4-4

Synthesis of Ethyl 1-(2-(ethylsulfonyl)-4-(trifluoromethyl)phenyl)-5-methyl-1H-1,2,3-triazole-4-carboxylate

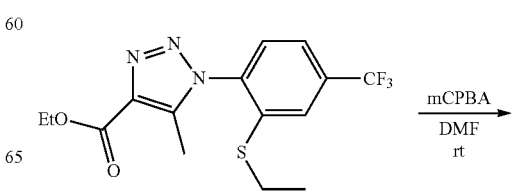

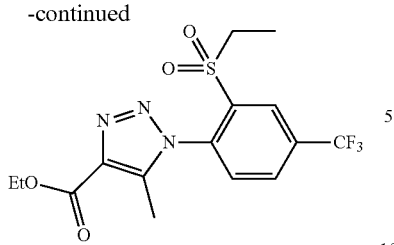

Ethyl 1-(2-(ethylthio)-4-(trifluoromethyl)phenyl)-5-methyl-1H-1,2,3-triazole-4-carboxylate (0.41 g) was dissolved in dichloromethane (10 ml) and the mixture was stirred at room temperature. Methachloroperbenzoic acid (70%, 0.59 g) was added thereto, and the mixture was stirred at room temperature for 3 hours. The reaction solution was poured into a mixed solution of saturated sodium hydrogen carbonate aqueous solution and saturated sodium thiosulfate aqueous solution, and the organic phase was extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.44 g (yield quant.) of the objective compound.

$^1$H-NMR of the obtained target product is shown below.

$^1$H-NMR (400 MHz, CDCl$_3$): δ 8.53 (d, 1H), 8.14 (dd, 1H), 7.58 (d, 1H), 4.48 (q, 2H), 3.30 (q, 2H), 2.48 (s, 3H), 1.46 (t, 3H), 1.29 (t, 3H).

Step 4-5

Synthesis of (1-(2-(ethyl sulfonyl)-4-(trifluoromethyl)phenyl)-5-methyl-1H-1,2,3-triazol-4-yl)methanol

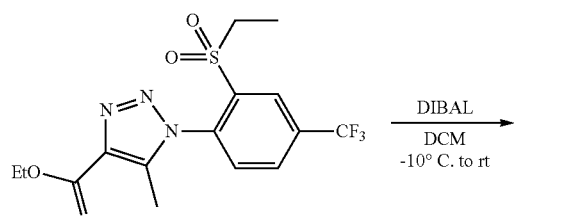

Ethyl 1-(2-(ethylsulfonyl)-4-(trifluoromethyl)phenyl)-5-methyl-1H-1,2,3-triazole-4-carboxylate (0.44 g) was dissolved in dichloromethane (20 ml) and the mixture was stirred at −10° C. Diisobutylaluminum hydride (1 M, 3.4 ml) was added thereto, and the mixture was stirred at 0° C. for 30 minutes and then stirred overnight at room temperature. A saturated Rochelle salt aqueous solution was added to the reaction solution, and the organic phase was extracted with dichloromethane. The obtained organic layer was washed with saturated brine, dried over anhydrous magnesium sulfate, and filtered. The filtrate was concentrated under reduced pressure, and the obtained residue was used in the next step without purification (yield quant.).

$^1$H-NMR of the obtained target product is shown below.

$^1$H-NMR (400 MHz, CDCl$_3$): δ 8.51 (s, 1H), 8.11 (d, 1H), 7.56 (d, 1H), 4.85 (d, 2H), 3.42 (t, 1H), 3.32 (q, 2H), 2.25 (s, 3H), 1.28 (t, 3H).

Step 4-6

Synthesis of 1-(2-(ethylsulfonyl)-4-(trifluoromethyl)phenyl)-5-methyl-1H-1,2,3-triazole-4-carbaldehyde

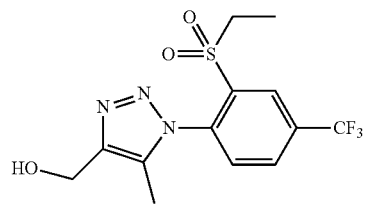

(1-(2-(ethylsulfonyl)-4-(trifluoromethyl)phenyl)-5-methyl-1H-1,2,3-triazol-4-yl) methanol obtained in Step 4-5 was dissolved in dichloromethane (60 ml), and manganese dioxide (0.96 g) was added thereto, and the mixture was stirred at room temperature for 2 hours. The reaction solution was filtered, the filtrate was concentrated under reduced pressure, and the obtained residue was used in the next step without purification (yield 96%).

$^1$H-NMR of the obtained target product is shown below.

$^1$H-NMR (400 MHz, CDCl$_3$): δ 10.29 (d, 1H), 8.54 (s, 1H), 8.16 (d, 1H), 7.59 (d, 1H), 3.32 (q, 2H), 2.49 (d, 3H), 1.31 (t, 3H).

Step 4-7

Synthesis of (Z)-4-(2-chloro-3,3,3-trifluoroprop-1-en-1-yl)-1-(2-(ethyl sulfonyl)-4-(trifluoromethyl)phenyl)-5-methyl-1H-1,2,3-triazole

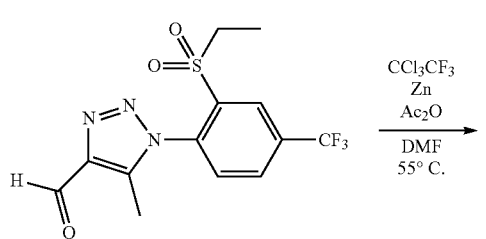

-continued

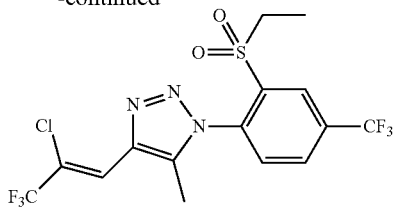

1-(2-(ethylsulfonyl)-4-(trifluoromethyl) phenyl)-5-methyl-1H-1,2,3-triazole-4-carbaldehyde (0.38 g) obtained in Step 4-6 was dissolved in N,N-dimethylformamide (10 ml) and the mixture was stirred at room temperature. Zinc powder (0.36 g), 1,1,1-trichloro-2,2,2-trifluoroethane (0.41 g) and acetic anhydride (0.17 g) were added and the inside of the reaction vessel was purged with argon and stirred at 55° C. overnight. The reaction solution was poured into a saturated aqueous sodium hydrogen carbonate solution and the organic phase was extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.08 g (yield 16%) of the objective compound.

$^1$H-NMR of the obtained target product is shown below.
$^1$H-NMR (400 MHz, CDCl$_3$): δ 8.53 (d, 1H), 8.14 (dd, 1H), 7.58 (d, 1H), 7.23 (s, 1H), 3.30 (q, 2H), 2.28 (d, 3H), 1.28 (t, 3H).

The compounds of the present invention produced by the same method as in the above Examples are shown in Tables 1 to 15. The material property data of the compound was entered in the column of "Material properties". As material property data, material state, melting point (m.p.), or refractive index ($n_D$) are described. When Q was Formula (II), the arrangement around the double bond was entered in the column of "configuration". "E" indicates E configuration, "Z" indicates Z configuration, and "E/Z" indicates that the compound is a mixture of compounds in both configurations. In the table, Me represents a methyl group, Et represents an ethyl group, $^c$Pr represents a cyclopropyl group, $^t$Bu represents a tertiary butyl group, and Ac represents an acetyl group.

It would be easily understood by those skilled in the art by the description of this specification that other compounds substituted with various groups, which are not be specifically shown in the present specification, can be produced and used by the above-mentioned method or the like without departing from the spirit and scope of the present invention.

Compound Nos. 1-108 to 1-117 in Table 1, compound Nos. 4-13 to 4-17 in Table 4, compound No. 7-7 in Table 7, compound Nos. 9-6 to 9-9 in Table 9, and compound Nos. 10-12 to 10-14 in Table 10 are Examples of production intermediates.

Table 1 shows the substituents of the compound represented by Formula (1).

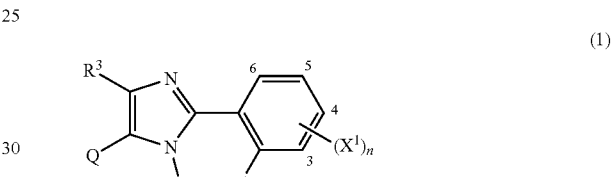

TABLE 1

| No. | (X$^1$)n | R$^1$ | R$^2$ | R$^3$ | Q | Configuration | Material properties |
|---|---|---|---|---|---|---|---|
| 1-1 | 4-CF$_3$ | SO$_2$Et | Me | H | CH=C(Cl)CF$_3$ | E/Z | m.p.: 100 to 102(° C.) |
| 1-2 | 4-CF$_3$ | SO$_2$Et | Me | H | CH=CCl$_2$ | — | m.p.: 194 to 196 (° C.) |
| 1-3 | 4-CF$_3$ | SO$_2$Et | Me | H | CH=CH$_2$ | — | m.p.: 168 to 170(° C.) |
| 1-4 | 4-CF$_3$ | SO$_2$Et | Me | H | CH=C(H)OCH$_3$ | Z | m.p.: 162 to 164(° C.) |
| 1-5 | 4-CF$_3$ | SO$_2$Et | Me | H | CH=C(H)OCH$_3$ | E | m.p.: 179 to 182(° C.) |
| 1-6 | 4-CF$_3$ | SEt | Me | H | CH=C(Cl)CF$_3$ | Z | m.p.: 94 to 96(° C.) |
| 1-7 | 4-CF$_3$ | SO$_2$Et | Me | H | CH=C(Cl)CF$_3$ | Z | m.p.: 123 to 124(° C.) |
| 1-8 | 4-CF$_3$ | SO$_2$Et | Me | H | CH=C(Cl)CF$_3$ | E | m.p.: 149 to 150(° C.) |
| 1-9 | 4-CF$_3$ | SEt | Me | H | CH=C(H)CF$_3$ | E | viscous oil |
| 1-10 | 4-CF$_3$ | SO$_2$Et | Me | H | CH=C(H)CF$_3$ | E | m.p.: 155 to 158(° C.) |
| 1-11 | 4-CF$_3$ | SO$_2$Et | Me | H | CH=CBr$_2$ | — | m.p.: 204 to 207(° C.) |
| 1-12 | 4-CF$_3$ | SO$_2$Et | Me | H | CH=C(H)OAc | E or Z | m.p.: 130 to 132(° C.) |
| 1-13 | 4-CF$_3$ | SO$_2$Et | Me | Br | CH=CBr$_2$ | — | m.p.: 163 to 170(° C.) |
| 1-14 | 4-CF$_3$ | SO$_2$Et | Me | Cl | CH=C(H)CF$_3$ | E | viscous oil |
| 1-15 | 4-CF$_3$ | SO$_2$Et | Me | H | CH$_2$CH$_2$CF$_3$ | — | viscous oil |
| 1-16 | 4-CF$_3$ | SEt | Me | H | CH(OH)CCl$_2$CF$_3$ | — | m.p.: 222 to 224(° C.) |
| 1-17 | 4-CF$_3$ | SEt | Me | H | CH(Cl)CCl$_2$CF$_3$ | — | m.p.: 99 to 100(° C.) |
| 1-18 | 4-CF$_3$ | SO$_2$Et | Me | H | CH(Cl)CCl$_2$CF$_3$ | — | viscous oil |
| 1-19 | 4-CF$_3$ | SO$_2$Et | Me | H | CH=NO—(4-CF$_3$O-phenyl) | E | m.p.: 155 to 158(° C.) |
| 1-20 | 4-CF$_3$ | SO$_2$Et | Me | H | CH=NO—(4-CF$_3$O-phenyl) | Z | viscous oil |
| 1-21 | 4-CF$_3$ | SO$_2$Et | Me | H | CH$_2$O—(3-Cl-5-CF$_3$-pyridine-2-yl) | — | m.p.: 114 to 118(° C.) |
| 1-22 | 4-CF$_3$ | SEt | Me | H | CH=NOCH$_2$CH$_3$ | E/Z | viscous oil |
| 1-23 | 4-CF$_3$ | SO$_2$Et | Me | H | CH=NOCH$_2$CH$_3$ | E/Z | m.p.: 138 to 141(° C.) |
| 1-24 | 4-CF$_3$ | SO$_2$Et | Me | H | CH=NOCH$_2$CF$_3$ | E or Z | viscous oil |
| 1-25 | 4-CF$_3$ | SO$_2$Et | Me | H | CN | — | m.p.: 120 to 123(° C.) |
| 1-26 | 4-CF$_3$ | SO$_2$Et | Me | H | CH(OCH$_3$)CH$_2$CF$_3$ | — | viscous oil |
| 1-27 | 4-CF$_3$ | SO$_2$Et | Me | H | CH$_2$CH=CBr$_2$ | — | viscous oil |
| 1-28 | 4-CF$_3$ | SO$_2$Et | Me | H | C≡C—Si(CH$_3$)$_3$ | — | m.p.: 167 to 169(° C.) |
| 1-29 | 4-CF$_3$ | SO$_2$Et | Me | H | C≡CH | — | m.p.: 156 to 158(° C.) |
| 1-30 | 4-CF$_3$ | SEt | Me | H | CH=C(CN)$_2$ | — | m.p.: 179 to 180(° C.) |
| 1-31 | 4-CF$_3$ | SO$_2$Et | Me | H | CH=C(CN)$_2$ | — | m.p.: 203 to 205(° C.) |
| 1-32 | 4-CF$_3$ | SO$_2$Et | Me | H | S(O)CF$_3$ | — | viscous oil |
| 1-33 | 4-CF$_3$ | SEt | Me | H | CH$_2$C(H)(OH)CCl$_2$CF$_3$ | — | m.p.: 193 to 196(° C.) |
| 1-34 | 4-CF$_3$ | SEt | Me | H | SCF$_3$ | — | viscous oil |
| 1-35 | 4-CF$_3$ | SOEt | Me | H | SCF$_3$ | — | m.p.: 92 to 94(° C.) |

TABLE 1-continued

| No. | (X¹)n | R¹ | R² | R³ | Q | Configuration | Material properties |
|---|---|---|---|---|---|---|---|
| 1-36 | 4-CF$_3$ | SO$_2$Et | Me | H | SCF$_3$ | — | viscous oil |
| 1-37 | 4-CF$_3$ | SO$_2$Et | Me | H | C≡C—CF$_3$ | — | m.p.: 155 to 159(° C.) |
| 1-38 | 4-CF$_3$ | SO$_2$Et | Me | H | CH=C(Cl)(4-OCF$_3$-phenyl) | E/Z | viscous oil |
| 1-39 | 4-CF$_3$ | SEt | Me | H | C(CH$_3$)=NOCH$_2$CF$_3$ | E or Z | m.p.: 94 to 96(° C.) |
| 1-40 | 4-CF$_3$ | SO$_2$Et | Me | H | C(CH$_3$)=NOCH$_2$CF$_3$ | E or Z | m.p.: 118 to 120(° C.) |
| 1-41 | 4-CF$_3$ | SO$_2$Et | Me | H | C(CH$_3$)=NOCH$_2$CF$_3$ | E or Z | m.p.: 85 to 87(° C.) |
| 1-42 | 4-CF$_3$ | SOEt | Me | H | CH=C(Cl)CF$_3$ | Z | m.p.: 147 to 149(° C.) |
| 1-43 | 4-CF$_3$ | SO$_2$Et | Me | H | CH=C(Br)CF$_3$ | Z | m.p.: 130 to 131(° C.) |
| 1-44 | 4-CF$_3$ | SO$_2$Et | Me | H | CCl=C(Cl)CF$_3$ | E | m.p.: 142 to 143(° C.) |
| 1-45 | 4-CF$_3$ | SO$_2$Et | Me | H | CH=C=C(Br)CF$_3$ | — | viscous oil |
| 1-46 | 4-CF$_3$ | SO$_2$Et | Me | H | C≡C—I | — | m.p.: 190 to 192(° C.) |
| 1-47 | 4-CF$_3$ | SO$_2$Et | Me | H | CH=C(H)I | Z | m.p.: 158 to 159(° C.) |
| 1-48 | 4-CF$_3$ | SO$_2$Et | Me | H | CH=C(H)I | E | m.p.: 207 to 210(° C.) |
| 1-49 | 4-CF$_3$ | SO$_2$Et | Me | H | CH=C(CN)CF$_3$ | E/Z | m.p.: 142 to 143(° C.) |
| 1-50 | 4-CF$_3$ | SO$_2$Et | Me | H | CH=C(CH$_3$)CF$_3$ | E/Z | m.p.: 119 to 120(° C.) |
| 1-51 | 4-CF$_3$ | SO$_2$Et | Me | H | CBr=C(Cl)CF$_3$ | E/Z | m.p.: 133 to 135(° C.) |
| 1-52 | 4-CF$_3$ | SO$_2$Et | Me | H | C(CH$_3$)=C(Cl)CF$_3$ | E/Z | m.p.: 136 to 137(° C.) |
| 1-53 | 4-CF$_3$ | SO$_2$Et | Me | H | C(CH$_3$)=C(CH$_3$)CF$_3$ | E/Z | m.p.: 121 to 123(° C.) |
| 1-54 | 4-CF$_3$ | SO$_2$Et | Me | H | CH=C(H)CF$_2$CF$_3$ | E | m.p.: 128 to 129(° C.) |
| 1-55 | 4-CF$_3$ | SO$_2$Et | Me | H | CH=C(Br)CF$_2$CF$_3$ | E or Z | m.p.: 152 to 154(° C.) |
| 1-56 | 4-CF$_3$ | SO$_2$Et | Me | Br | CH=C(H)CF$_2$CF$_3$ | E | m.p.: 124 to 125(° C.) |
| 1-57 | 4-CF$_3$ | SO$_2$Et | Me | H | CH=C($^c$Pr)CF$_3$ | E or Z | m.p.: 107 to 108(° C.) |
| 1-58 | 4-CF$_3$ | SO$_2$Et | Me | H | CH=C(4-CF$_3$-phenyl)CF$_3$ | E or Z | $n_D$(20.4° C.)1.5155 |
| 1-59 | 4-CF$_3$ | SEt | Me | H | CH=C(Br)CF$_3$ | Z | m.p.:106 to 108(° C.) |
| 1-60 | 4-CF$_3$ | SO$_2$Et | Me | H | CH=C(3-CF$_3$-phenyl)CF$_3$ | E or Z | $n_D$(20.4° C.)1.5140 |
| 1-61 | 4-CF$_3$ | SO$_2$Et | Me | H | CH=C(2-CF$_3$-phenyl)CF$_3$ | E or Z | amorphous |
| 1-62 | 4-CF$_3$ | SEt | Me | H | CH=O(CF$_3$)$_2$ | — | m.p.: 91 to 93(° C.) |
| 1-63 | 4-CF$_3$ | SO$_2$Et | Me | H | CH=C(CF$_3$)$_2$ | — | m.p.: 133 to 134(° C.) |
| 1-64 | 4-CF$_3$ | SO$_2$Et | Me | H | CH=C(Cl)CF$_2$CF$_3$ | Z | m.p.: 132 to 134(° C.) |
| 1-65 | 4-CF$_3$ | SO$_2$Et | Me | Cl | CH=C(H)CF$_2$CF$_3$ | E | m.p.: 124 to 126(° C.) |
| 1-66 | 4-CF$_3$ | SO$_2$Et | Me | Me | CH=C(Cl)CF$_3$ | E/Z | solid |
| 1-67 | 4-CF$_3$ | SEt | Me | H | N=C(Cl)CF$_3$ | E or Z | amorphous |
| 1-68 | 4-CF$_3$ | SO$_2$Et | Me | H | N=C(Cl)CF$_3$ | E or Z | m.p.: 101 to 104(° C.) |
| 1-69 | 4-CF$_3$ | SO$_2$Et | Me | H | N=C(NHCH$_3$)CF$_3$ | E/Z | amorphous |
| 1-70 | 4-CF$_3$ | SO$_2$Et | Me | H |  | trans isomer | $n_D$ (22.5° C.) 1.4951 |
| 1-71 | 4-CF$_3$ | SEt | Me | H | CH=C(F)SO$_2$Ph | E | m.p.: 140 to 141(° C.) |
| 1-72 | 4-CF$_3$ | SO$_2$Et | Me | H | CH=C(F)SO$_2$Ph | E | m.p.: 103 to 105(° C.) |
| 1-73 | 4-CF$_3$ | SO$_2$Et | Me | H | CH=C(F)I | E | m.p.: 202 to 204(° C.) |
| 1-74 | 4-CF$_3$ | SO$_2$Et | Me | H | CH=C(F)CF$_3$ | Z | m.p.: 177 to 178(° C.) |
| 1-75 | 4-CF$_3$ | SO$_2$Et | Me | H | CH=C(F)CF$_2$CF$_3$ | Z | amorphous |
| 1-76 | 4-CF$_3$ | SO$_2$Et | Me | H | CH=C(H)SCF$_3$ | Z | m.p.: 111 to 113(° C.) |
| 1-77 | 4-CF$_3$ | SO$_2$Et | Me | H | CH=C(H)SCF$_3$ | E | m.p.: 148 to 149(° C.) |
| 1-78 | 4-CF$_3$ | SO$_2$Et | Me | Cl | CH=C(H)SCF$_3$ | Z | m.p.: 145 to 146(° C.) |
| 1-79 | 4-CF$_3$ | SO$_2$Et | Me | H | CH=C(Cl)SCF$_3$ | E or Z | amorphous |
| 1-80 | 4-CF$_3$ | SEt | Me | H | CH=C(Cl)I | E/Z | m.p.: 140 to 141(° C.) |
| 1-81 | 4-CF$_3$ | SO$_2$Et | Me | H | CH=C(Cl)I | E or Z | m.p.: 204 to 205(° C.) |
| 1-82 | 4-CF$_3$ | SO$_2$Et | Me | H | CH=C(H)Cl | Z | m.p.: 162 to 164(° C.) |
| 1-83 | 4-CF$_3$ | SO$_2$Et | Me | H | CH=C(H)(1,3-dioxolan-2-yl) | E/Z | viscous oil |
| 1-84 | 4-CF$_3$ | SO$_2$Et | Me | H | CH=C(H)CHO | E/Z | m.p.: 202 to 203(° C.) |
| 1-85 | 4-CF$_3$ | SO$_2$Et | Me | H | CH=C(H)C(H)(OH)CCl$_2$CF$_3$ | E/Z | viscous oil |
| 1-86 | 4-CF$_3$ | SO$_2$Et | Me | H | CH=C(H)CHC(Cl)Cl$_3$ | E/Z, E/Z | m.p.: 119 to 121(° C.) |
| 1-87 | 5-F | SEt | Me | H | CH=C(Cl)CF$_3$ | E/Z | viscous oil |
| 1-88 | 5-F | SO$_2$Et | Me | H | CH=C(Cl)CF$_3$ | E/Z | m.p.: 166 to 167(° C.) |
| 1-89 | 5-(1 H-1,2,4-triazole-1-yl) | SO$_2$Et | Me | H | CH=C(Cl)CF$_3$ | E/Z | m.p.: 176 to 180(° C.) |
| 1-90 | 5-F | SO$_2$Et | Me | H | CH=C(1H-1,2,4-triazole-1-yl)CF$_3$ | E/Z | viscous oil |
| 1-91 | 4-CF$_3$ | SO$_2$Et | Me | H | CH=C(H)C(H)(OH)CF$_3$ | E | m.p.: 189 to 192(° C.) |
| 1-92 | 4-CF$_3$ | SO$_2$Et | Me | Cl | CH=C(H)C(H)(OH)CF$_3$ | E | $n_D$(20.0° C.)1.5117 |
| 1-93 | 4-CF$_3$ | SO$_2$Et | Me | H | CH=C(H)C(H)(OCH$_3$)CF$_3$ | E | $n_D$(22.6° C.)1.5113 |
| 1-94 | 4-CF$_3$ | SO$_2$Et | Me | H | CH=C(H)C(H)(OAc)CF$_3$ | E | $n_D$(22.7° C.)1.5077 |
| 1-95 | 4-CF$_3$ | SEt | Me | H | CH=C(Cl)I | E/Z | m.p.: 122 to 124(° C.) |
| 1-96 | 4-CF$_3$ | SO$_2$Et | Me | H | C≡C(4-CF$_3$-phenyl) | — | m.p.: 187 to 190(° C.) |
| 1-97 | 4-CF$_3$ | S(=O)(=NH)Et | Me | H | CH=C(CHCF$_3$) | Z | viscous oil |
| 1-98 | 4-CF$_3$ | SEt | Me | H | CO$_2$$^t$Bu | — | $n_D$(20.5° C.)1.5296 |
| 1-99 | 4-CF$_3$ | SO$_2$Et | Me | H | CO$_2$$^t$Bu | — | m.p.: 148 to 150(° C.) |
| 1-100 | 4-CF$_3$ | SEt | Me | H | CONH$^t$Bu | — | m.p.: 131 to 132(° C.) |
| 1-101 | 4-CF$_3$ | SO$_2$Et | Me | H | CONH$^t$Bu | — | m.p.: 145 to 147(° C.) |
| 1-102 | 4-CF$_3$ | SO$_2$Et | Me | H | CON(Me)$^t$Bu | — | $n_D$(17.9° C.)1.5135 |
| 1-103 | 4-CF$_3$ | SEt | Me | H | CONHCH$_2$CH$_3$ | — | m.p.: 61 to 63(° C.) |
| 1-104 | 4-CF$_3$ | SO$_2$Et | Me | H | CONHCH$_2$CH$_3$ | — | m.p.: 203 to 205(° C.) |
| 1-105 | 4-CF$_3$ | SO$_2$Et | Me | H | CON(Me)CH$_2$CF$_3$ | — | $n_D$(17.4° C.)1.5017 |
| 1-106 | 4-CF$_3$ | SO$_2$Et | Me | H | CON(Ac)CH$_2$CF$_3$ | — | m.p.: 163 to 165(° C.) |
| 1-107 | 4-CF$_3$ | SO$_2$Et | Me | H | CH$_2$OCH$_2$CF$_3$ | — | viscous oil |
| 1-108 | 4-CF$_3$ | SO$_2$Et | Me | H | Br | — | m.p.: 164 to 165(° C.) |
| 1-109 | 4-CF$_3$ | SO$_2$Et | Me | H | I | — | m.p.: 181 to 183(° C.) |

TABLE 1-continued

| No. | (X$^1$)n | R$^1$ | R$^2$ | R$^3$ | Q | Configuration | Material properties |
|---|---|---|---|---|---|---|---|
| 1-110 | 5-F | SO$_2$Et | Me | H | Br | — | m.p.: 198 to 202(° C.) |
| 1-111 | 5-(1H-1,2,4-triazole-1-yl) | SO$_2$Et | Me | H | Br | — | m.p.: 226 to 229(° C.) |
| 1-112 | 5-F | SEt | Me | H | Br | — | viscous oil |
| 1-113 | 5-CN | SEt | Me | H | Br | — | m.p.: 109 to 111(° C.) |
| 1-114 | 5-CN | SO$_2$Et | Me | H | Br | — | m.p.: 189 to 191(° C.) |
| 1-115 | 4-CF$_3$,5-F | SEt | Me | H | Br | — | m.p.: 98 to 100(° C.) |
| 1-116 | 4-CF$_3$,5-F | SO$_2$Et | Me | H | Br | — | m.p.: 193 to 195(° C.) |
| 1-117 | 4,5-F$_2$ | SO$_2$Et | Me | H | Br | — | m.p.: 160 to 162(° C.) |

Table 2 shows the substituents of the compound represented by Formula (2).

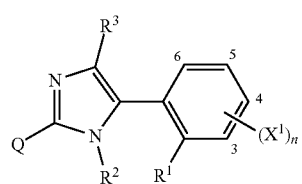

(2)

TABLE 2

| No. | (X$^1$)n | R$^1$ | R$^2$ | R$^3$ | Q | Configuration | Material properties |
|---|---|---|---|---|---|---|---|
| 2-1 | 4-CF$_3$ | SO$_2$Et | Me | H | CH=CHCF$_3$ | E | viscous oil |
| 2-2 | 4-CF$_3$ | SEt | Me | H | CH=CHCF$_3$ | E/Z | m.p.: 62 to 65(° C.) |
| 2-3 | 4-CF$_3$ | SEt | Me | H | CH(OH)CCl$_2$CF$_3$ | — | m.p.: 185 to 187(° C.) |
| 2-4 | 4-CF$_3$ | SEt | Me | H | CH(OAc)CCl$_2$CF$_3$ | — | viscous oil |
| 2-5 | 4-CF$_3$ | SO$_2$Et | Me | H | CH=C(Cl)CF$_3$ | Z | viscous oil |
| 2-6 | 4-CF$_3$ | SEt | Me | H | 1,3-dioxolan-2-yl | — | n$_D$(20.7° C.)1.5522 |
| 2-7 | 4-CF$_3$ | SO$_2$Et | Me | H | 1,3-dioxolan-2-yl | — | m.p.: 113 to 115(° C.) |

Table 3 shows the substituents of the compound represented by Formula (3).

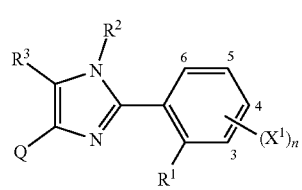

(3)

TABLE 3

| No. | (X$^1$)n | R$^1$ | R$^2$ | R$^3$ | Q | Configuration | Material properties |
|---|---|---|---|---|---|---|---|
| 3-1 | 4-CF$_3$ | SO$_2$Et | Me | H | CH=C(Cl)CF$_3$ | Z | m.p.: 155 to 158(° C.) |
| 3-2 | 4-CF$_3$ | SO$_2$Et | Me | H | CH=C(Cl)CF$_3$ | E/Z | m.p.: 145 to 146(° C.) |
| 3-3 | 4-CF$_3$ | SO$_2$Et | Me | H | CH$_2$O-(3-Cl-5-CF$_3$-pyridine-2-yl) | — | viscous oil |
| 3-4 | 4-CF$_3$ | SO$_2$Et | Me | H | CH=C(Cl)I | E/Z | amorphous |
| 3-5 | 4-CF$_3$ | SO$_2$Et | Me | H | CH=C(Cl)CF$_2$CF$_3$ | Z | m.p.: 115 to 116(° C.) |

Table 4 shows the substituents of the compound represented by Formula (4).

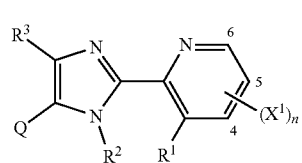

(4)

TABLE 4

| No. | (X¹)n | R¹ | R² | R³ | Q | Configuration | Material properties |
|---|---|---|---|---|---|---|---|
| 4-1 | 5-CF₃ | SO₂Et | Me | H | CH=CH₂ | — | m.p.: 163 to 165(° C.) |
| 4-2 | 5-CF₃ | SO₂Et | Me | H | CH=C(Cl)CF₃ | E/Z | m.p.: 180 to 183(° C.) |
| 4-3 | 5-CF₃ | SO₂Et | Me | H | CH=CHCF₃ | E/Z | amorphous |
| 4-4 | — | SO₂Et | Me | H | CH=C(Cl)CF₃ | E/Z | m.p.: 178 to 181(° C.) |
| 4-5 | 6-(1H-1,2,4-triazole-1-yl) | SO₂Et | Me | H | CH=C(Cl)CF₃ | E/Z | m.p.: 194 to 197(° C.) |
| 4-6 | 6-Cl | SO₂Et | Me | H | CH=C(Cl)CF₃ | E/Z | m.p.: 151 to 152(° C.) |
| 4-7 | 5-(1H-1,2,4-triazole-1-yl) | SO₂Et | Me | H | CH=C(Cl)CF₃ | E/Z | solid |
| 4-8 | 5-CF₃ | SO₂Et | Me | H | CH=C(Cl)CF₂CF₃ | Z | m.p.: 125 to 127(° C.) |
| 4-9 | 5-CF₃ | SO₂Et | Me | H | C≡C—CF₂CF₃ | — | m.p.: 130 to 132(° C.) |
| 4-10 | 6-(1H-1,2,4-triazole-1-yl) | SO₂Et | Me | H | CH=C(Cl)CF₂CF₃ | Z | m.p.: 160 to 162(° C.) |
| 4-11 | 6-Cl | SO₂Et | Me | H | CH=C(Cl)CF₂CF₃ | Z | viscous oil |
| 4-12 | 6-(1H-1,2,4-triazole-1-yl) | SO₂Et | Me | H | CH=C(H)CF₂CF₃ | E | m.p.: 146 to 147(° C.) |
| 4-13 | 5-CF₃ | SO₂Et | Me | H | Br | — | m.p.: 142 to 146(° C.) |
| 4-14 | 6-Cl | SEt | Me | H | Br | — | m.p.: 64 to 66(° C.) |
| 4-15 | 6-(1H-1,2,4-triazole-1-yl) | SO₂Et | Me | H | Cl | — | m.p.: 162 to 164(° C.) |
| 4-16 | 6-(1H-1,2,4-triazole-1-yl) | SO₂Et | Me | H | Br | — | m.p.: 208 to 212(° C.) |
| 4-17 | 6-(4-OCF₃-phenyl) | SO₂Et | Me | H | Br | — | m.p.: 155 to 158(° C.) |

Table 5 shows the substituents of the compounds represented by Formula (5).

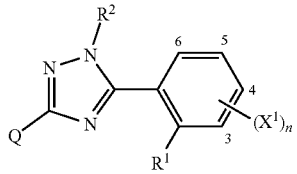

(5)

TABLE 5

| No. | (X¹)n | R¹ | R² | Q | Configuration | Material properties |
|---|---|---|---|---|---|---|
| 5-1 | 4-CF₃ | SO₂Et | Me | 1,3-dioxolan-2-yl | — | m.p.: 140 to 142(° C.) |
| 5-2 | 4-CF₃ | SO₂Et | Me | CH=C(Cl)CF₃ | E/Z | m.p.: 165 to 166(° C.) |

Table 6 shows the substituents of the compound represented by Formula (6).

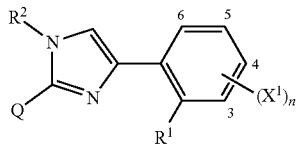

(6)

TABLE 6

| No. | (X¹)n | R¹ | R² | Q | Configuration | Material properties |
|---|---|---|---|---|---|---|
| 6-1 | 4-CF₃ | SO₂Et | Me | CH=C(Cl)CF₃ | Z | m.p.: 155 to 157(° C.) |

Table 7 shows the substituents of the compound represented by Formula (7).

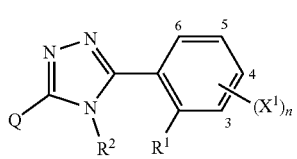

(7)

TABLE 7

| No. | (X¹)n | R¹ | R² | Q | Configuration | Material properties |
|---|---|---|---|---|---|---|
| 7-1 | 4-CF₃ | SO₂Et | Me | CH=C(Cl)CF₃ | Z | m.p.: 198 to 200(° C.) |
| 7-2 | 4-CF₃ | SEt | Me | SCH₂CF₃ | — | m.p.: 90 to 91(° C.) |
| 7-3 | 4-CF₃ | SOEt | Me | SCH₂CF₃ | — | m.p.: 156 to 157(° C.) |
| 7-4 | 4-CF₃ | SO₂Et | Me | SCH₂CF₃ | — | m.p.: 100 to 102(° C.) |
| 7-5 | 4-CF₃ | SO₂Et | Me | S(O)CH₂CF₃ | — | m.p.: 84 to 85(° C.) |
| 7-6 | 4-CF₃ | SO₂Et | Me | S(O)₂CH₂CF₃ | — | m.p.: 145 to 146(° C.) |
| 7-7 | 4-CF₃ | SO₂Et | Me | Br | — | m.p.: 150 to 151(° C.) |

Table 8 shows the substituents of the compound represented by Formula (8).

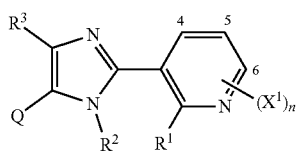

(8)

TABLE 8

| No. | (X¹)n | R¹ | R² | R³ | Q | Configuration | Material properties |
|---|---|---|---|---|---|---|---|
| 8-1 | 6-CF₃ | SEt | Me | H | CH=C(Cl)CF₃ | E/Z | m.p.: 99 to 101(° C.) |
| 8-2 | 6-CF₃ | SO₂Et | Me | H | CH=C(Cl)CF₃ | E/Z | m.p.: 150 to 152(° C.) |

Table 9 shows the substituents of the compound represented by Formula (9).

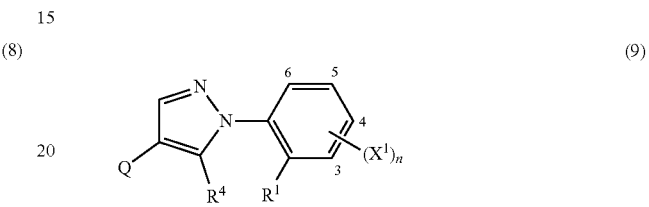

(9)

TABLE 9

| No. | (X¹)n | R¹ | R⁴ | Q | Configuration | Material properties |
|---|---|---|---|---|---|---|
| 9-1 | 4-CF₃ | SO₂Et | NH₂ | CO₂Et | — | m.p.: 173 to 175(° C.) |
| 9-2 | 4-CF₃ | SO₂Et | Me | CONH-(4-CF₃-phenyl) | — | m.p.: 252 to 256(° C.) |
| 9-3 | 4-CF₃ | SO₂Et | Me | CONH-(3-CF₃-phenyl) | — | m.p.: 175 to 177(° C.) |
| 9-4 | 4-CF₃ | SO₂Et | Me | CH=C(Cl)CF₃ | E/Z | m.p.: 166 to 168(° C.) |
| 9-5 | 4-CF₃, 6-SEt | SEt | NH₂ | CO₂Et | — | m.p.: 134 to 136(° C.) |
| 9-6 | 4-CF₃ | SO₂Et | H | Br | — | m.p.: 121 to 123(° C.) |
| 9-7 | 4-CF₃ | SO₂Et | NH₂ | Br | — | m.p.: 193 to 195(° C.) |
| 9-8 | 5-Cl | SO₂Et | Me | Br | — | m.p.: 118 to 120(° C.) |
| 9-9 | 4-CF₃, 6-SEt | SEt | NH₂ | Br | — | m.p.: 108 to 110(° C.) |

Table 10 shows the substituents of the compound represented by Formula (10).

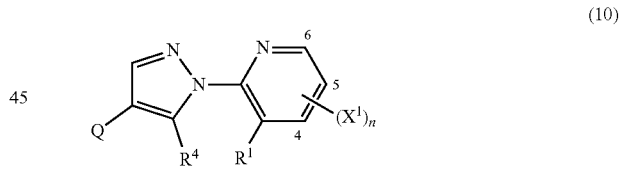

(10)

TABLE 10

| No. | (X¹)n | R¹ | R⁴ | Q | Configuration | Material properties |
|---|---|---|---|---|---|---|
| 10-1 | 5-CF₃ | SO₂Et | H | CH=C(Cl)CF₃ | E/Z | m.p.: 130 to 131(° C.) |
| 10-2 | 5-CF₃ | SO₂Et | Me | CH=C(Cl)CF₃ | E/Z | m.p.: 182 to 183(° C.) |
| 10-3 | — | SO₂Et | Me | CH=C(Cl)CF₃ | E/Z | m.p.: 156 to 158(° C.) |
| 10-4 | 6-(1H-1,2,4-triazole-1-yl) | SO₂Et | Me | CH=C(Cl)CF₃ | E/Z | m.p.: 175 to 177(° C.) |
| 10-5 | 6-(1H-1,2,4-triazole-1-yl) | SO₂Et | Me | CH=C(Cl)CF₂CF₃ | Z | m.p.: 150 to 152(° C.) |
| 10-6 | — | SEt | Me | CH=C(Cl)CF₂CF₃ | Z | viscous oil |
| 10-7 | — | SO₂Et | Me | CH=C(Cl)CF₂CF₃ | Z | m.p.: 143 to 145(° C.) |
| 10-9 | 6-Cl | SO₂Et | Me | CH=C(Cl)CF₂CF₃ | Z | viscous oil |
| 10-10 | 6-(3-NH₂-1H-1,2,4-triazole-1-yl) | SO₂Et | Me | CH=C(Cl)CF₂CF₃ | Z | m.p.: 188 to 190(° C.) |
| 10-11 | 6-(5-NH₂-1H-1,2,4-triazole-1-yl) | SO₂Et | Me | CH=C(Cl)CF₂CF₃ | Z | m.p.: 191 to 193(° C.) |
| 10-12 | 5-CF₃ | SEt | H | Br | — | m.p.: 100 to 102(° C.) |
| 10-13 | 5-CF₃ | SO₂Et | H | Br | — | m.p.: 192 to 194(° C.) |
| 10-14 | 5-CF₃ | SEt | NH₂ | Br | — | m.p.: 86 to 89(° C.) |

Table 11 shows the substituents of the compound represented by Formula (11).

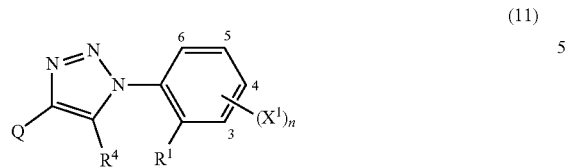

(11)

TABLE 11

| No. | $(X^1)n$ | $R^1$ | $R^4$ | Q | Configuration | Material properties |
|---|---|---|---|---|---|---|
| 11-1 | 4-$CF_3$ | SEt | H | CH=C(Cl)$CF_3$ | E/Z | m.p.: 78 to 79(° C.) |
| 11-2 | 4-$CF_3$ | $SO_2$Et | H | CH=C(Cl)$CF_3$ | E/Z | m.p.: 180 to 181(° C.) |
| 11-3 | 4-$CF_3$ | $SO_2$Et | Me | CH=C(Cl)$CF_3$ | Z | m.p.: 95 to 97(° C.) |

Table 12 shows the substituents of the compound represented by Formula (12).

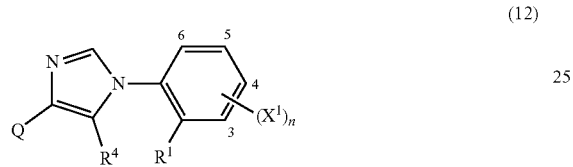

(12)

TABLE 12

| No. | $(X^1)n$ | $R^1$ | $R^4$ | Q | Configuration | Material properties |
|---|---|---|---|---|---|---|
| 12-1 | 4-$CF_3$ | SEt | Me | $CO_2$Et | — | m.p.: 143 to 145(° C.) |
| 12-2 | 4-$CF_3$ | SEt | Me | $CH_2$OH | — | m.p.: 135 to 136(° C.) |
| 12-3 | 4-$CF_3$ | SEt | Me | CH=C(Cl)$CF_3$ | E/Z | m.p.: 126 to 127(° C.) |
| 12-4 | 4-$CF_3$ | $SO_2$Et | Me | CH=C(Cl)$CF_3$ | E/Z | m.p.: 138 to 140(° C.) |

Table 13 shows the substituents of the compound represented by Formula (13).

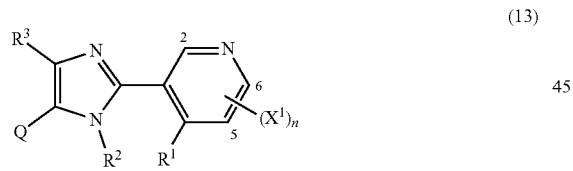

(13)

TABLE 13

| No. | $(X^1)n$ | $R^1$ | $R^2$ | $R^3$ | Q | Configuration | Material properties |
|---|---|---|---|---|---|---|---|
| 13-1 | 6-$CF_3$ | $SO_2$Et | Me | H | CH=C(Cl)$CF_3$ | E/Z | m.p.: 124 to 124(° C.) |

Table 14 shows the substituents of the compound represented by Formula (14).

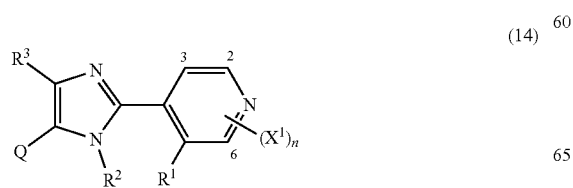

(14)

TABLE 14

| No. | $(X^1)n$ | $R^1$ | $R^2$ | $R^3$ | Q | Configuration | Material properties |
|---|---|---|---|---|---|---|---|
| 14-1 | — | SEt | Me | H | CH=C(Cl)CF$_3$ | E/Z | viscous oil |
| 14-2 | — | SO$_2$Et | Me | H | CH=C(Cl)CF$_3$ | E/Z | white solid |
| 14-3 | 2-(1H-1,2,4-triazole-1-yl) | SO$_2$Et | Me | H | CH=C(Cl)CF$_3$ | E/Z | white solid |

TABLE 15

| No. | Structure | Material Properties |
|---|---|---|
| 15-1 | (structure) | amorphous |
| 15-2 | (structure) | m.p.: 211 to 215(° C.) |
| 15-3 | (structure) | m.p.: 155 to 156(° C.) |
| 15-4 | (structure) | m.p.: 155 to 156(° C.) |
| 15-5 | (structure) | m.p.: 83 to 85(° C.) |
| 15-6 | (structure) | m.p.: 138 to 140(° C.) |
| 15-7 | (structure) | m.p.: 218 to 220(° C.) |

TABLE 15-continued

| No. | Structure | Material Properties |
|---|---|---|
| 15-8 | F$_5$C$_2$–C(Cl)=CH–(pyrazole with CH$_3$)–N–(pyridine N-oxide with SO$_2$Et) | m.p.: 200 (° C.) up |

Among the compounds shown in Tables 1 to 15, $^1$H-NMR data was measured for compound noted in the material properties column as viscous oil or amorphous. The measured values are shown in Table 16.

TABLE 16

| Compound No. | $^1$H-NMR(CDCl$_3$-d$_6$, δppm) |
|---|---|
| 1-9 | 7.60(s, 1H), 7.53(s, 1H), 7.51(d, 1H), 7.46(d, 1H), 7.02(dd, 1H), 6.19-6.10(m, 1H), 3.52(s, 3H), 2.90(q, 2H), 1.29(t, 3H). |
| 1-14 | 8.44(s, 1H), 8.03(dd, 1H), 7.64(d, 1H), 6.97(dq, 1H), 6.59-6.50(m, 1H), 3.45(s, 3H), 3.39(q, 2H), 1.26(t, 3H). |
| 1-15 | 8.43(s, 1H), 7.99(d, 1H), 7.62(d, 1H), 6.92(s, 1H), 3.40(q, 2H), 3.34(s, 3H), 3.91-3.87(m, 2H), 2.58-2.47(m, 2H), 1.23(t, 3H). |
| 1-18 | 8.44(s, 1H), 8, 01(dd, 1H), 7.67(d, 1H), 7.59(s, 1H), 5.49(s, 1H), 3.46(s, 3H), 3.30(q, 2H), 1.22(t, 3H). |
| 1-20 | 8.46(d, 1H), 8.45(s, 1H), 8.04(dd, 1H), 7.68(d, 1H), 7.48(s, 1H), 7.18(m, 4H), 3.73(s, 3H), 3.45(q, 2H), 1.27(t, 3H). |
| 1-22 | 8.11-8.09(m, 1H), 7.60(m, 1H), 7.52-7.46(m, 2H), 7.36(s, 1H), 4.35(q, 2H, Z isomer), 4.20(q, 2H, E isomer), 3.67(s, 3H, E isomer), 3.53(s, 3H, Z isomer), 2.93-2.86(m, 2H), 1.43-1.24(m, 6H). |
| 1-24 | 8.44(s, 1H), 8.20(s, 1H), 8.02(d, 1H), 7.65(d, 1H), 7.38(s, 1H), 4.48(q, 2H), 3.61(s, 3H), 3.49-3.42(m, 2H), 1 26(t, 3H). |
| 1-26 | 8.43(d, 1H), 8.01(dd, 1H), 7.65(d, 1H), 7.10(s, 1H), 4.78(m, 2H), 3.44(s, 3H), 3.40-3.32(m, 1H), 3.28(s, 3H), 2.91-2.55(m, 2H), 1.22(t, 3H). |
| 1-27 | 8.43(s, 1H), 8.00(d, 1H), 7.65(d, 1H), 6.95(s, 1H), 6.56(t, 1H), 3.46(d, 2H), 3.33(s, 3H), 1.23(t, 3H). |
| 1-32 | 8.45(d, 1H), 8.06(dd, 1H), 7.75(s, 1H), 7.67(d, 1H), 3.69(s, 3H), 3.35(q, 2H), 1.26(t, 3H). |
| 1-34 | 7.64(s, 1H), 7.62(m, 1H), 7.54-7.47(m, 2H), 3.55(s, 3H), 2.88(q, 2H), 1.27(t, 3H). |
| 1-36 | 8.45(d, 1H), 8.03(dd, 1H), 7.66(d, 1H), 7.59(s, 1H), 3.50(s, 3H), 3.39(q, 2H), 1.23(t, 3H). |
| 1-38 | 8.46-8.42(m, 1H), 8.03-8.97(m, 1H), 7.72-7.57(m, 1H), 7.53-7.50(m, 2H), 7.28-7.22(m, 3H), 6.72(d, 1H, E isomer), 6.51(d, 1H, Z isomer), 3.45-3.34(m, 5H), 1.28-1.18(m, 3H). |
| 1-45 | 8.45(s, 1H), 8.03(d, 1H), 7.66(d, 1H), 7.37(s, 1H), 6.83(q, 1H), 3.48-3.42(m, 5H), 1.27(t, 3H). |
| 1-61 | 8.42(s, 1H), 7.98(d, 1H), 7.83(d, 1H), 7.73(dd, 1H), 7.64(dd, 1H), 7.57(d, 1H), 7.47(d, 1H), 7.13(s, 1H), 5.97(s, 1H), 3.45(s, 3H), 3.35-3.14(m, 2H), 1.16(t, 3H). |
| 1-66 | 8.44(m, 1H), 8.01(m, 1H), 7.65(m, 1H), 7.20(s, 1H, Z isomer), 6.96(s, 1H, E isomer), 3.43(q, 2H), 3.33(s, 3H, Z isomer), 3.30(s, 3H, E isomer), 2.29(s, 3H, Z isomer), 2.21(s, 3H, E isomer), 1.27-1.22(m, 3H). |
| 1-67 | 7.93(s, 1H), 7.62(s, 1H), 7.53(d, 1H), 7.47(d, 1H), 3.53(s, 3H), 2.93(q, 2H), 1.30(t, 3H). |
| 1-69 | 8.43(s, 1H), 7.98(m, 1H), 7.63(m, 1H), 6.84-6.74(m, 1H), 5.55-5.41(m, 1H), 3.53-3.46(m, 2H), 3.32-3.29(m, 3H), 3.09-3.02(m, 3H), 1.28-1.24(m, 3H). |
| 1-75 | 6 8.45(s, 1H), 8.02(d, 1H), 7.68(s, 1H), 7.63(d, 1H), 6.36(d, 1H), 3.44(s, 3H), 3.40(q, 2H), 1.25(t, 3H). |
| 1-79 | 6 8.45(s, 1H), 8.06(d, 1H), 8.02(d, 1H), 7.63(d, 1H), 7.17(s, 1H), 3.43(s, 3H), 3.41(q, 2H), 1.26(t, 3H). |
| 1-83 | 8.44-8.42(m, 1H), 8.00-7.98(m, 1H), 7.64-7.62(m, 1H), 7.38(s, 1H, Z isomer), 7.34(s, 1H, E isomer), 6.64(d, 1H, E isomer), 6.52(d, 1H, Z isomer), 6.12(dd, 1H, E isomer), 5.88(dd, 1H, Z isomer), 5.62(d, 1H, Z isomer), 5.44(d, 1H, E isomer), 4.10-3.95(m, 2H), 3.43-3.37(m, 5H), 1.28-1.21(m, 3H). |
| 1-85 | 8.44(s, 1H), 8.01(d, 1H), 7.61(d, 1H), 7.39(s, 1H), 6.70(d, 1H), 6.20(dd, 1H), 6.03(d, 1H), 3.47-3.39(m, 5H), 1.26(t, 3H). |
| 1-87 | 8.08(s, 1H), 7.48-6.93(m, 5H), 3.50(s, 3H, Z isomer), 3.45(s, 3H, E isomer), 2.76-2.69(m, 2H), 1.19-1.15(m, 3H). |
| 1-90 | 8.38-8.15(m, 3H), 7.43-7.29(m, 2H), 7.24-7.12(m, 1H), 6.20(s, 1H, Z isomer), 6.07(q, 1H, E isomer), 3.50(s, 3H, E or Z isomer), 3.33-3.18(m, 2H), 2.95(s, 3H, E or Z isomer), 1.28-1.16(m, 3H). |
| 1-97 | 8.51(d, 1H), 8.06(s, 1H), 7.98(dd, 1H), 7.59(d, 1H), 7.13(s, 1H), 3.55-3.39(m, 5H), 2.65(br s, 1H), 1.27(t, 3H). |

TABLE 16-continued

| Compound No. | $^1$H-NMR(CDCl$_3$-d$_6$, δppm) |
|---|---|
| 1-107 | 8.43(s, 1H), 8.01(d, 1H), 7.65(d, 1H), 7.17(s, 1H), 4.73(s, 3H), 3.84(q, 2H), 3.49-3.39(m, 4H), 1.23(t, 3H). |
| 1-112 | 7.43(dd, 1H) 7.17-7.10(m, 3H), 3.45(s, 3H), 2.75(q, 2H), 1.18(t, 3H). |
| 2-1 | 8.49(d, 1H), 8.00(dd, 1H), 7.58(d, 1H), 7.14(s, 3H), 7.04(dq, 1H), 6.78(dq, 1H), 3.46(s, 3H), 3.02(q, 2H), 1.20(t, 3H). |
| 2-4 | 8.54(s, 1H), 7.46(d, 1H), 7.36(d, 1H), 7.14(s, 1H), 6.45(s, 1H), 3.56(s, 3H), 2.88(q, 2H), 2.21(s, 3H), 1.26(t, 3H). |
| 2-5 | 8.49(d, 1H), 8.00(dd, 2H), 7.59(d, 1H), 7.31(s, 1H), 7.20(s, 1H), 3.46(s, 3H), 3.02(q, 2H), 1.26(t, 3H). |
| 3-3 | 8.44(d, 1H), 8.39(d, 1H), 8.00(dd, 1H), 7.89(d, 1H), 7.69(d, 1H), 8.29(s, 1H), 5.57(s, 2H), 3.51(s, 3H), 3.42(q, 2H), 1.23(t, 3H). |
| 3-4 | 8.43(s, 1H, E or Z isomer), 8.28(s, 1H, E or Z isomer), 8.00(d, 1H, E or Z isomer), 7.88-7.37(m, 3H), 3.49(s, 3H, E or Z isomer), 3.48(s, 3H, E or Z isomer), 3.45-3.37(m, 2H), 1.28-1.22(m, 3H). |
| 4-3 | 9.14(m, 1.3H), 8.72(m, 1.3H), 7.61(s, 0.3H, Z isomer), 7.50(s, 1H, E isomer), 7.04(dq, 1H, E isomer), 6.68(d, 0.3H, Z isomer), 6.25-6.16(m, 1H, E isomer), 5.88-5.78(m, 0.3H, Z isomer), 4.00-3.94(m, 2.6H), 3.71(s, 3H, E isomer), 3.67(s, 0.9H, Z isomer), 1.40-1.35(m, 3.9H). |
| 4-7 | 9.37-9.35(m, 1H), 8.81-8.77(m, 2H), 8.24(s, 1H), 8.08(s, 1H, Z isomer), 8.02(s, 1H, E isomer), 7.18(s, 1H, Z isomer), 6.95(s, 1H, E isomer), 3.97-3.91(m, 2H), 3.68(s, 3H, Z isomer), 3.64(s, 3H, E isomer), 1.44-1.37(m, 3H). |
| 4-10 | 9.15(s, 1H), 8.67(d, 1H), 8.21(d, 1H), 8.18(s, 1H), 8.12(s, 1H), 7.17(s, 1H), 3.80(q, 2H), 3.68(s, 3H), 1.36(t, 3H). |
| 4-11 | 8.42(d, 1H), 8.07(s, 1H), 7.62(d, H), 7.12(s, 1H), 3.86(q, 2H), 3.67(s, 3H), 1.36(t, 3H). |
| 10-6 | 8.48(s, 1H), 8.36(dd, 1H), 7.78(dd, 1H), 7.39(dd, 1H), 7.11(s, 1H), 2.90(q, 2H), 2.34(s, 3H), 1.31(t, 3H). |
| 10-9 | 8.48(d, 1H), 8.46(d, 1H), 7.66(d, 1H), 7.10(s, 1H), 3.70(q, 2H), 2.42(s, 3H), 1.35(t, 3H). |
| 14-1 | 8.71(s, 1H, Z isomer), 8.57(d, 1H, Z isomer), 8.11(s, 1H, Z isomer), 7.31(d, 1H, Z isomer), 7.16(s, 1H, Z isomer), 3.53(s, 3H, Z isomer), 2.86(q, 2H, Z isomer), 1.25(t, 3H, Z isomer) |
| 14-2 | 9.34(s, 1H, Z isomer), 9.03(d, 1H, Z isomer), 8.06(s, 1H, Z isomer), 7.42(d, 1H, Z isomer), 7.14(s, 1H, Z isomer), 3.48(s, 3H, Z isomer), 3.40(q, 2H, Z isomer), 1.28(t, 3H, Z isomer). |
| 14-3 | 9.55(s, 1H, Z isomer), 9.55(s, 1H, E isomer), 9.17(s, 1H, Z isomer), 9.16(s, 1H, E isomer), 8.27(s, 1H), 8.20(s, 1H, Z isomer), 8.18(s, 1H, E isomer), 8.08(s, 1H, Z isomer), 7.47(s, 1H, Z isomer), 7.41(s, 1H, E isomer), 7.35(s, 1H, E isomer), 3.58(s, 3H, Z isomer), 3.52(s, 3H, E isomer), 3.44(q, 2H) 1.26(t, 3H); |
| 15-1 | 8.41(s, 1H), 8.12(d, 1H), 7.66(s, 1H), 7.60-7.53(m, 3H), 7.48-7.44(m, 2H), 2.99(q, 2H), 2.49(s, 3H), 1.35(t, 3H). |

NOTE)
Solvent for measuring Compound No. 14-3: MeOH-d$_4$

[Biological Test]

The following test examples show that the arylazole compound of the present invention (hereinafter referred to as the compound of the present invention) is useful as an active ingredient of a pest control agent, particularly an insecticide. "Part" is on a weight basis.

(Preparation of Test Emulsion)

5 parts of the compound of the present invention, 93.6 parts of dimethylformamide, and 1.4 parts of polyoxyethylene alkylaryl ether were mixed and dissolved to prepare an emulsion (I) with 5% the active ingredient.

The insecticidal rate and the control rate were calculated by the following Equation.

Insecticidal rate (%)=(number of dead insects/number of test insects)×100

Control rate={1−(Nt)/(Nc)}×100

Nt: Number of parasites in spray treatment group
Nc: Number of parasites in untreated group (Test Example 1) Efficacy Test on *Mythimna separata*

0.8 g of commercially available artificial diet (Insector LFS, manufactured by Nosan Corp.) and Emulsion (I) 1 µl were well mixed and 0.2 g per each treatment group was packed in a plastic test container (1.4 ml) to prepare test feed. Two *Mythimna separata* second instar larvae were inoculated into each treatment group and sealed with a plastic lid. The container was placed in a thermostatic chamber at 25° C., and the insecticidal rate and food intake were examined on the fifth day. The test was performed twice. Further, a test conducted under the same conditions except that the compound of the present invention was removed from the emulsion (I) was performed as a vehicle control group.

The compounds shown in Table 17 were used for an efficacy test against the *Mythimna separata*. It has been shown that all of the compounds were effective against the *Mythimna separata*, with the insecticidal rate being 100% and the feeding amount being 10% or less in comparison with the vehicle control group.

TABLE 17

| |
|---|
| 1-1 |
| 1-6 |
| 1-7 |
| 1-8 |
| 1-9 |
| 1-10 |
| 1-11 |
| 1-14 |

TABLE 17-continued 1-17
1-18
1-24
1-42
1-43
1-49
1-54
1-55
1-57
1-59
1-64
1-65
1-70
1-74
1-77
1-79
1-80
1-81
1-87
1-88
1-95
1-97
2-1
3-1
3-2
3-5
4-2
4-3
4-4
4-5
4-8
4-9
4-10
4-11
4-12
5-2
9-4
10-2
10-3
10-4
10-5
10-6
10-7
10-10
10-11
11-3
15-4
15-6
15-8

(Test Example 2) Efficacy Test on *Mythimna separata*

Emulsion (I) was diluted with water so that the concentration of the compound of the present invention was set to be 125 ppm. The corn leaves were immersed in the diluent for 30 seconds. This corn leaf was placed in a petri dish, and five *Mythimna separata* second-instar larvae were released. The petri dish was placed in a thermostatic chamber at a temperature of 25° C. and a humidity of 60%. Life and death determination was made when 6 days passed since the release of insects, and the insecticidal rate was calculated. The test was performed twice.

The compounds shown in Table 18 were used for an efficacy test against *Mythimna separata*. All of the compounds showed an insecticidal rate of 80% or more with respect to *Mythimna separata*.

TABLE 18

1-1
1-2
1-6

TABLE 18-continued 1-7
1-8
1-10
1-11
1-17
1-18
1-43
1-55
1-64
1-97
3-1
3-2
3-5
4-2
4-3
4-4
4-5
4-8
4-10
5-2
9-4
10-2
10-5
10-10
11-3

(Test Example 3) Efficacy Test Against *Spodoptera litura*

Emulsion (I) was diluted with water so that the concentration of the compound of the present invention was set to be 125 ppm. Cabbage leaves were immersed in the diluent for 30 seconds. This cabbage leaf was placed in a petri dish, and five *Spodoptera litura* second-instar larvae were released. The petri dish was placed in a thermostatic chamber at a temperature of 25° C. and a humidity of 60%. Life and death determination was made when 6 days passed since the release of insects, and the insecticidal rate was calculated. The test was performed twice.

The compounds shown in Table 19 were used for an efficacy test against *Spodoptera litura*. All of the compounds showed an insecticidal rate of 80% or more against *Spodoptera litura*.

TABLE 19

1-1
1-2
1-6
1-7
1-18
1-42
1-43
1-49
1-54
1-55
1-57
1-59
1-63
1-64
1-75
3-1
4-2
4-5
4-8
4-9
4-10
9-4
10-5
10-10

(Test Example 4) Efficacy Test on *Plutella xylostella*

Emulsion (I) was diluted with water so that the concentration of the compound of the present invention was 125 ppm. Cabbage leaves were immersed in the diluent for 30 seconds. This cabbage leaf was put in a petri dish, and five *Plutella xylostella* second-instar larvae were released. The petri dish was placed in a thermostatic chamber at a temperature of 25° C. and a humidity of 60%. Life and death determination was made when 3 days passed since the release of insects, and the insecticidal rate was calculated. The test was performed twice.

The compounds shown in Table 20 were used for an efficacy test against *Plutella xylostella*. All of the compounds showed an insecticidal rate of 80% or more.

TABLE 20

| |
| --- |
| 1-1 |
| 1-7 |
| 1-43 |
| 1-55 |
| 1-64 |
| 4-5 |
| 4-7 |
| 4-8 |
| 4-10 |
| 4-12 |
| 9-4 |
| 10-2 |
| 10-4 |
| 10-5 |
| 10-10 |
| 11-3 |

(Test Example 5) Efficacy Test on *Aphis gossypii*

Emulsion (I) was diluted with water so that the concentration of the compound of the present invention was set to be 125 ppm. Cucumber was planted in a small pot and inoculated with *Aphis gossypii* nymphs on the first main leaf. The diluted solution was sprayed on cucumber seedlings. The cucumbers were placed in a thermostatic chamber having a temperature of 25° C. and a humidity of 60%. When 4 days passed after spraying, life and death of *Aphis gossypii* was determined, and the insecticidal rate was calculated. The test was performed twice.

The compounds shown in Table 21 were used for an efficacy test against *Aphis gossypii*. All of the compounds showed an insecticidal rate of 80% or more.

TABLE 21

| |
| --- |
| 1-1 |
| 1-7 |
| 1-8 |
| 1-10 |
| 1-43 |
| 1-55 |
| 1-64 |
| 1-104 |
| 1-105 |
| 1-106 |
| 4-3 |
| 4-4 |
| 4-5 |
| 4-8 |
| 4-10 |
| 4-12 |
| 10-5 |
| 15-4 |

(Test Example 6) Efficacy Test on *Aphis craccivora*

Cowpea was raised in a small pot and inoculated with *Aphis craccivora* nymphs on primary leaves. The emulsion (I) was diluted with water so that the compound of the present invention was set to be 125 ppm, and the diluted solution was sprayed on the cowpea infested with *Aphis craccivora*. The cowpea was placed in a thermostatic chamber at a temperature of 25° C. and a humidity of 60%. When 4 days passed after spraying, the life and death determination of *Aphis craccivora* was conducted, and the insecticidal rate was calculated. The test was performed twice.

The compounds shown in Table 22 were used for an efficacy test against *Aphis craccivora*. All of the compounds showed an insecticidal rate of 80% or more against *Aphis craccivora*.

TABLE 22

| |
| --- |
| 1-1 |
| 1-6 |
| 1-7 |
| 1-8 |
| 1-9 |
| 1-10 |
| 1-12 |
| 1-15 |
| 1-18 |
| 1-24 |
| 1-26 |
| 1-40 |
| 1-43 |
| 1-49 |
| 1-50 |
| 1-52 |
| 1-53 |
| 1-54 |
| 1-55 |
| 1-57 |
| 1-59 |
| 1-63 |
| 1-64 |
| 1-70 |
| 1-74 |
| 1-76 |
| 1-77 |
| 1-79 |
| 1-86 |
| 1-87 |
| 1-93 |
| 1-97 |
| 1-99 |
| 1-105 |
| 1-106 |
| 2-1 |
| 3-5 |
| 4-3 |
| 4-4 |
| 4-5 |
| 4-8 |
| 4-9 |
| 4-10 |
| 4-12 |
| 5-2 |
| 8-2 |
| 9-4 |
| 10-4 |
| 10-5 |
| 10-6 |
| 10-7 |
| 10-9 |

TABLE 22-continued 10-10
11-3
15-4
15-5
15-6

(Test Example 7) Efficacy Test Against *Bemisia tabaci*

Emulsion (I) was diluted with water so that the concentration of the compound of the present invention was set to be 125 ppm. The diluted solution was sprayed on tomato seedlings and air-dried. On the day of spraying, adults of the *Bemisia tabaci* were released and allowed to lay eggs. The number of parasitic larvae was counted 12 days after spraying, and then the control rate was calculated. The test was performed twice.

The compounds shown in Table 23 were used for an efficacy test against *Bemisia tabaci*. All of the compounds had a next generation control rate of 80% or more.

TABLE 23

1-1
1-2
1-7
1-8
1-43
1-54
1-55
1-57
1-59
1-63
1-64
1-79
3-1
3-2
4-4
4-5
4-8
4-9
4-10
4-12
10-5

(Test Example 8) Efficacy Test on *Phyllotreta striolata*

Emulsion (I) was diluted with water so that the compound of the present invention was set to be 125 ppm to prepare a test solution. The above diluted solution was sprayed on chingensai seedlings (seventh true leaf development stage) planted in a small pot. After air-drying, the chingensai seedlings were placed in a plastic cup and 10 adults of *Phyllotreta striolata* were released. The temperature was kept in a thermostatic chamber at 25° C. and humidity was 65%, the life and death determination was performed 7 days after the release of insects, and the insecticidal rate was calculated. The test was performed twice.

The compounds shown in Table 24 were tested for potency against adults of *Phyllotreta striolata*. The insecticidal rate was 80% or more.

TABLE 24

1-1
1-7

TABLE 24-continued 1-43
1-54
1-55
1-57
1-63
1-64
1-74
1-89
4-5
4-7
4-8
4-9
4-10
4-12
10-5
10-6
10-7
10-10

(Test Example 9) Efficacy Test on *Culex pipiens molestus*

Emulsion (I) was diluted with water so that the compound of the present invention was set to be 10 ppm to prepare a test solution. Twenty first instar larvae of *Culex pipiens molestus* were released into 100 mL of this solution, the number of dead insects was counted one day later and the insecticidal rate was calculated. The test was performed twice.

The compounds shown in Table 25 were used for an efficacy test against first instar larvae of *Culex pipiens molestus*. As a result, all of the compounds showed an insecticidal rate of 100% against the first instar larva of *Culex pipiens* molestus.

TABLE 25

1-1
1-7
1-64
1-107
3-4
3-5
4-5
4-8
4-9
4-10
4-12
8-1
10-3
10-4
10-5
10-6
10-7
10-9
10-10
10-11
15-5
15-6
15-7
15-8

(Test Example 10) Efficacy Test on *Nilaparvata lugens*

Emulsion (I) was diluted with water so that the concentration of the compound of the present invention was set to be 125 ppm. Rice young seedlings were immersed in the diluted solution for 30 seconds and allowed to air dry, then placed in a plastic case, and five second instar larvae of *Nilaparvata lugens* were released. The temperature was kept in a thermostatic chamber at 25° C. and humidity was 65%, the life and death determination was performed 7 days after the inoculation, and the insecticidal rate was calculated. The test was performed twice.

The compounds shown in Table 26 were used for an efficacy test against *Nilaparvata lugens*. All of the compounds showed an insecticidal rate of 80% or more.

TABLE 26

| |
|---|
| 1-64 |
| 4-5 |
| 4-7 |
| 4-8 |
| 4-9 |
| 4-10 |
| 4-12 |
| 10-5 |
| 10-7 |
| 10-10 |

(Test Example 11) Efficacy Test on *Aphis gossypii* (Rooting Treatment Test)

The cucumber seedlings raised in a small pot were drawn out from the small pot, the soil adhering to the root portion was washed off with tap water, and the root portion was dipped in tap water and hydroponically cultivated. Cucumber seedlings were inoculated with *Aphis gossypii* nematodes. Emulsion (I) was diluted with water to obtain a diluted solution having a concentration of the compound of the present invention of 8 ppm. The tap water was replaced with the diluent and the hydroponic culture with the diluent was continued in a thermostatic chamber at a temperature of 25° C. and a humidity of 60%. When 6 days passed from the start of hydroponic culture with the diluent, life and death determination on *Aphis gossypii* was performed and the insecticidal rate was calculated. The test was performed twice.

The compound of Compound No. 1-1 was used for an efficacy test against *Aphis gossypii*. The insecticidal rate was 80% or more.

(Test Example 12) Efficacy Test on Housefly

The compound of the present invention was diluted with acetone and added dropwise to 1 g of cubic sugar such that the concentration was set to be 100 ppm. The cubic sugar was placed in a plastic cup, and ten housefly female adults were released and capped. After storage at 25° C. and 24 hours passing from releasing, life and death determination was performed and the insecticidal rate was calculated. The test was performed twice.

The compound of Compound No. 1-1 was used for an efficacy test against housefly female adults. The insecticidal rate was 80% or more.

(Test Example 13) Efficacy Test on *Plutella xylostella* (Soil Immersion Test)

Emulsion (I) was diluted with water such that the concentration of the compound of the present invention was set to be 500 ppm to obtain a test solution. 10 ml of the test solution was irrigated to the stocker at chingengsai seedlings (seventh true leaf development stage) planted in a small pot and placed in a greenhouse at 25° C. for 7 days. Chingengsai seedlings were transferred into glass greenhouse and 300 adults of *Plutella xylostella* per 50 chingengsai were released in glass greenhouse. When 7 days passed after release, the number of surviving *Plutella xylostella* infested in Chingengsai seedlings was counted and the control rate was calculated. The test was performed twice.

The compound of Compound No. 1-1 was used for an efficacy test against *Plutella xylostella*. The control rate was 80% or more.

(Experimental Example 14) Efficacy Test on *Mythimna separata* (Seed Treatment Test)

0.1 g of the compound of the present invention was diluted with 2 mL of acetone to prepare a test solution. 10 g of wheat seeds were added to the test solution, subjected to air dry, and 100 seeds were planted in a planter. The planters were placed in a greenhouse at 25° C. for 7 days. Thereafter, 100 of first instar larvae of *Mythimna separata* were released in the planter. After placing in a greenhouse at 25° C. for 3 days, the number of surviving *Mythimna separata* was counted and the control rate was calculated. The test was performed twice.

The compounds shown in Table 27 were used for an efficacy test against first instar larvae of *Mythimna separata*. The control rate was 80% or more.

TABLE 27

| |
|---|
| 1-1 |
| 1-7 |
| 1-64 |
| 4-5 |
| 4-8 |
| 4-10 |
| 4-12 |
| 10-4 |
| 15-7 |

(Test Example 15) Efficacy Test on *Rhopalosiphum padi* (Seed Treatment Test)

0.1 g of the compound of the present invention was diluted with 2 mL of acetone to prepare a test solution. 10 grams of wheat seeds were added to the test solution, subjected to air dry, and 100 seeds were planted in a planter. After placing in a greenhouse at 25° C. for 7 days, the planter was inoculated with 50 adult *Rhopalosiphum padi*. The number of surviving *Rhopalosiphum padi* infested 6 days after the inoculation was counted and the control rate was calculated. The test was performed twice.

The compounds shown in Table 28 were used for an efficacy test against *Rhopalosiphum padi*. The control rate was 80% or more.

TABLE 28

| |
|---|
| 1-1 |
| 1-7 |
| 1-64 |
| 4-5 |
| 4-8 |
| 4-10 |
| 4-12 |

(Test Example 16) Feeding Effect Test on *Ornithodoros moubata*

A DMSO solution of the compound of the present invention was mixed with the defibrin blood of sheep to obtain a mixed solution of 10 ppm. 2 ml of this mixed solution was placed in a container and capped with a parafilm membrane. In addition, 20 tritonymphs of *Ornithodoros moubata* were released and allowed to suck the blood through a parafilm membrane for about 30 minutes. The nymphs were transferred to a storage container and incubated in a thermostatic chamber at a temperature of 28° C. and a humidity of 80%, and the life and death and developmental stage were observed 14 days after blood sucking. The test was performed twice.

For the compound of Compound No. 1-1, a feeding effect test on *Ornithodoros moubata* was conducted, and the test showed an insecticidal rate of 90% or more.

(Test Example 17) Contact Effect Test on *Rhipicephalus microplus*

A DMSO solution of the compound of the present invention was diluted with water to obtain a test solution at 100 ppm. This drug solution was dropped into a container containing 20 larvae of *Rhipicephalus microplus* and incubated in a thermostatic chamber at a temperature of 28° C. and a humidity of 80%. The larvae's life and death were determined 24 hours after the drug treatment. The test was performed twice.

With respect to the compound of Compound No. 1-1, a contact effect test on *Rhipicephalus microplus* was conducted, and the test showed an insecticidal rate of 90% or more.

(Test Example 18) Contact/Feeding Effect Test on *Lucilia cuprina* Larvae

A DMSO solution of the compound of the present invention was mixed with horse meat to obtain a mixture of 1000 ppm. 20 *Lucilia cuprina* larvae were introduced into the test tube with the mixture. The mixture was incubated in a thermostatic chamber at a temperature of 28° C. and a humidity of 80%, and the larvae's life and death were determined 48 hours after the start of the test. The test was performed twice.

When the compound of Compound No. 1-1 was used in a contact/feeding effect test against larvae of *Lucilia cuprina*, the test showed an insecticidal rate of 90% or more.

(Test Example 19) Contact/Feeding Effect Test on *Aedes aegypti* Larvae

A DMSO solution of the compound of the present invention was diluted with water to obtain a diluted solution of 100 ppm. 10 *Aedes aegypti* first instar larvae were placed in each well of a 96-well microtiter plate together with breeding water, 1/10 of 100 ppm diluted solution were added and tested at a final concentration of 10 ppm. The mixture was incubated in a thermostatic chamber at a temperature of 28° C. and a humidity of 80%, and the larvae's life and death were determined for 48 hours after the drug treatment. The test was performed twice.

When the compound of Compound No. 1-1 was used for a contact/feeding effect test against *Aedes aegypti* larvae, the test showed an insecticidal rate of 90% or more.

Any of the compounds randomly selected from the compounds of the present invention exerted the above-mentioned effects. It has been implicated that the compounds of the present invention including compounds which are not exemplified is effective for pest control, in particular, exhibiting miticidal and insecticidal activity, or the like. It has also been implicated that the compound of the present invention is effective on ectoparasites which harm humans and livestock.

INDUSTRIAL APPLICABILITY

The arylazole compound of the present invention can control pests which are problematic in terms of agricultural crops and hygiene. In particular, various agricultural pests and mites can be effectively controlled at relatively low concentrations. In addition, it is possible to effectively control ectoparasites and endoparasites which harm humans and livestock. Therefore, the present invention is industrially useful.

The invention claimed is:

1. A compound represented by Formula (I), or a salt or N-oxide compound thereof:

wherein, in Formula (I), $A^1$, $A^2$ and $A^4$ independently represents a carbon atom, a —CH group, or a nitrogen atom, and $A^3$ represents a carbon atom or a —CH group, provided that two or more of $A^1$, $A^2$ and $A^4$ not nitrogen atoms at the same time, $X^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, an unsubstituted or substituted C1-6 alkylaminocarbonyl group, a mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C3-8 cycloalkyl group, an unsubstituted or substituted C6-10 aryl group, an unsubstituted or substituted 3- to 6-membered heterocyclyl group, an unsubstituted or substituted amino group, a halogeno group, a cyano group, or a nitro group, n represents the number of chemically acceptable $X^1$ and is any integer of 0 to 4, when n is 2 or more, $X^1$ may be the same as or different from each other, and also two $X^1$ may be bound together to form a ring, $R^1$ represents a C1-6 alkylthio group, a C1-6 alkylsulfinyl group, or a C1-6 alkylsulfonyl group, and D is a group represented by Formulas (r') to (t'),

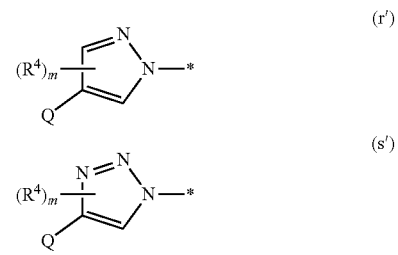

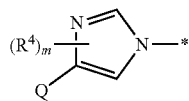

(t')

wherein * represents a binding position,
Q represents a group represented by Formula (IV),

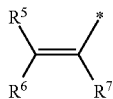

(IV)

wherein * represents a binding position,
$R^5$ to $R^7$ each independently represents a hydrogen atom, an unsubstituted or substituted C1-6 alkyl group, an unsubstituted or substituted C2-6 alkenyl group, an unsubstituted or substituted C2-6 alkynyl group, a C1-6 alkoxy group, a C1-6 alkylcarbonyloxy group, a halogeno group, or a cyano group,
$R^4$ represents an unsubstituted or substituted C1-6 alkyl group, an unsubstituted or substituted C2-6 alkenyl group, an unsubstituted or substituted C2-6 alkynyl group, an unsubstituted or substituted C3-8 cycloalkyl group, an unsubstituted or substituted amino group, a halogeno group, a cyano group, or a nitro group, and
m represents the number of chemically acceptable $R^4$ and is any integer of 0 to 2, and when m is 2 or more, $R^4$ may be the same as or different from each other,
wherein substituents which form the substituted groups mentioned above are selected from the group consisting of: a C1-6 alkyl group, a C2-6 alkenyl group, a C2-6 alkynyl group, a C3-8 cycloalkyl group, a hydroxyl group, a C1-6 alkoxy group, a C2-6 alkenyloxy group, a C2-6 alkynyloxy group, a C6-10 aryloxy group, a C6-10 aryl C1-6 alkoxy group, a 5- to 6-membered heteroaryloxy group, a 5- to 6-membered heteroaryl C1-6 alkyloxy group, a formyl group, a C1-6 alkylcarbonyl group, a formyloxy group, a C1-6 alkylcarbonyloxy group, a C6-10 arylcarbonyl group, a C1-6 alkoxycarbonyl group, a C1-6 alkoxycarbonyloxy group, a carboxyl group, a halogeno group, a C1-6 haloalkyl group, a C2-6 haloalkenyl group, a C2-6 haloalkynyl group, a C1-6 haloalkoxy group, a C2-6 haloalkenyloxy group, a C1-6 haloalkylcarbonyl group, an amino group, a C1-6 alkyl-substituted amino group, a C6-10 arylamino group, a C6-10 aryl C1-6 alkylamino group, a formylamino group, a C1-6 alkylcarbonylamino group, a C1-6 alkoxycarbonylamino group, a dimethylaminocarbonyl group, a phenylaminocarbonyl group, an N-phenyl-N-methylaminocarbonyl group, an N-butyl-N-methylaminocarbonyl group, an imino C1-6 alkyl group, an N-hydroxy-iminomethyl group, a (1-(N-hydroxy)-imino) ethyl group, a (1-(N-hydroxy)-imino) propyl group, an N-methoxy-iminomethyl group, a (1-(N-methoxy)-imino) ethyl group, an aminocarbonyloxy group, a C1-6 alkyl-substituted aminocarbonyloxy group, a mercapto group, a C1-6 alkylthio group, a C1-6 haloalkylthio group, a C6-10 arylthio group, a 5- to 6-membered heteroarylthio group, a C1-6 alkylsulfinyl group, a C1-6 haloalkylsulfinyl group, a C6-10 arylsulfinyl group, a 5-to 6-membered heteroarylsulfinyl group, a C1-6 alkylsulfonyl group, a C1-6 haloalkylsulfonyl group, a C6-10 arylsulfonyl group, a 5- to 6-membered heteroarylsulfonyl group, a C1-6 alkylsulfonyloxy group, a C1-6 haloalkylsulfonyloxy group, a tri-C1-6 alkyl-substituted silyl group, a tri-C6-10 aryl-substituted silyl group, a cyano group, and a nitro group.

2. The compound according to claim 1, which is represented by Formula (b), or a salt or N-oxide compound thereof:

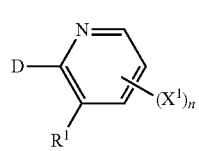

(b)

wherein, in Formula (b), $X^1$, $R^1$, n and D have the same meanings as those in Formula (I).

3. A pest control agent comprising at least one compound according to claim 1, a salt thereof, or an N-oxide compound thereof as an active ingredient and a carrier.

4. A method for controlling a pest or mite on or in a subject comprising the step of administrating to the subject an effective amount of at least one compound according to claim 1, a salt thereof, or an N-oxide compound thereof, wherein the pest or mite is one or more selected from the group consisting of:
butterflies and moths of the order Lepidoptera; pests of the order Thysanoptera; pests of the order Hemiptera; pests of the order Polyphaga; pests of the order Diptera; pests of the order Orthoptera; and mites of the subclass Acari.

5. A method for controlling an insect or acarus on or in a subject comprising the step of administrating to the subject an effective amount of at least one compound according to claim 1, a salt thereof, or an N-oxide compound thereof.

6. A method for controlling an ectoparasite on or in a subject comprising the step of administrating to the subject an effective amount of at least one compound according to claim 1, a salt thereof, or an N-oxide compound thereof.

7. A method for controlling or expelling an endoparasite in a subject comprising the step of administrating to the subject an effective amount of at least one compound according to claim 1, a salt thereof, or an N-oxide compound thereof.

* * * * *